US005641777A

United States Patent [19]

Emonds-Alt et al.

[11] Patent Number: 5,641,777

[45] Date of Patent: Jun. 24, 1997

[54] SUBSTITUTED HETEROCYCLIC COMPOUNDS AND PHARMACEUTICAL COMPOSITIONS IN WHICH THEY ARE PRESENT

[75] Inventors: Xavier Emonds-Alt, Combaillaux; Isabelle Grossriether, Paris; Patrick Gueule, Teyran; Vincenzo Proietto, Saint Georges d'Orques; Didier Van Broeck, Murviel les Montpellier, all of France

[73] Assignee: Sanofi, Paris, France

[21] Appl. No.: 593,938

[22] Filed: Jan. 30, 1996

[30] Foreign Application Priority Data

| | | | |
|---|---|---|---|
| Jan. 30, 1995 | [FR] | France | 95 01016 |
| Jul. 4, 1995 | [FR] | France | 95 08046 |
| Nov. 3, 1995 | [FR] | France | 95 13005 |

[51] Int. Cl.$^6$ ...................... A61K 31/445; A61K 31/535; C07D 413/06; C07D 471/08

[52] U.S. Cl. .................................... 514/235.5; 514/230.8; 514/228.8; 514/305; 544/82; 544/96; 544/127; 544/129; 544/130; 544/141; 544/360; 544/362; 546/133; 546/209; 546/210

[58] Field of Search .................... 544/130, 96; 546/133; 514/235.5

[56] References Cited

U.S. PATENT DOCUMENTS

| | | |
|---|---|---|
| 5,236,921 | 8/1993 | Emonds-Alt et al. . |
| 5,317,020 | 5/1994 | Emonds-Alt et al. . |
| 5,332,817 | 7/1994 | Desai et al. . |
| 5,340,822 | 8/1994 | Emonds-Alt et al. . |
| 5,350,852 | 9/1994 | Emonds-Alt et al. . |
| 5,411,971 | 5/1995 | Emonds-Alt et al. . |

*Primary Examiner*—Robert W. Ramsuer
*Attorney, Agent, or Firm*—Bacon & Thomas

[57] ABSTRACT

The invention relates to neurokinin receptor antagonist compounds of the formula

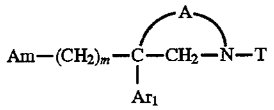

(I)

in which:

A is a divalent radical selected from:

$A_1$) —O—CO—
$A_2$) —$CH_2$—O—CO—
$A_3$) —O—$CH_2$—CO—
$A_4$) —O—$CH_2$—$CH_2$—
$A_5$) —N($R_1$)—CO—
$A_6$) —N($R_1$)—CO—CO—
$A_7$) —N($R_1$)—$CH_2$—$CH_2$—
$A_8$) —O—$CH_2$— in which:

$R_1$ is a hydrogen or a ($C_1$–$C_4$)-alkyl; and

Am is a nitrogen-containing heterocycle

APPLICATION: Neurokinin receptor antagonists.

15 Claims, No Drawings

SUBSTITUTED HETEROCYCLIC COMPOUNDS AND PHARMACEUTICAL COMPOSITIONS IN WHICH THEY ARE PRESENT

The present invention relates to novel substituted heterocyclic compounds, to a method of preparing them and to the pharmaceutical compositions in which they are present as the active principle.

More particularly, the present invention relates to a novel class of substituted heterocyclic compounds for therapeutic use in pathological phenomena involving the tachykinin system, such as: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, I. S. and Pernow ed., 287–293, Raven Press, New York), gastrointestinal disorders (D. Regoli et al., Trends Pharmacol. Sci., 1985, 6, 481–484), respiratory disorders (J. Mizrahi et al., Pharmacology, 1982, 25, 39–50), neurological disorders and neuropsychiatric disorders (C. A. Maggi et al., J. Autonomic Pharmacol., 1993, 13, 23–93), these examples being neither limiting nor exclusive.

In recent years, numerous research studies have been carried out on tachykinins and their receptors. Tachykinins are distributed throughout both the central nervous system and the peripheral nervous system. The tachykinin receptors have been recognized and are classified into three types: $NK_1$, $NK_2$, $NK_3$. Substance P (SP) is the endogenous ligand of the $NK_1$ receptors, neurokinin A ($NK_A$) that of the $NK_2$ receptors and neurokinin B ($NK_B$) that of the $NK_3$ receptors.

The $NK_1$, $NK_2$ and $NK_3$ receptors have been identified in different species. A review by C. A. Maggi et al. looks at the tachykinin receptors and their antagonists and gives an account of the pharmacological studies and the applications in human therapeutics (J. Autonomic Pharmacol., 1993, 13, 23–93).

The following non-peptide compounds may be mentioned among the antagonists specific for the $NK_1$ receptor: CP-96345 (J. Med. Chem., 1992, 35, 2591–2600), RP-68651 (Proc. Natl. Acad. Sci. USA, 1991, 88, 10208–10212), SR 140333 (Curr. J. Pharmacol., 1993, 250, 403–413).

For the $NK_2$ receptor, a non-peptide selective antagonist, SR 48968, has been described in detail (Life Sci., 1992, 50, PL101–PL106).

As far as the $NK_3$ receptor is concerned, some non-peptide compounds have been described as having an affinity for the $NK_3$ receptor of the rat and guinea-pig brain (FASEB J., 1993, 7 (4), A710–4104); a peptide antagonist, $[Trp^7, \beta\text{-}Ala^8]NK_A$, which has a weak specificity for the $NK_3$ receptor of the rat, has also been described (J. Autonomic Pharmacol., 1993, 13, 23–93).

Patent application EP-A-336230 describes peptide derivatives which are substance P and neurokinin A antagonists useful for the treatment and prevention of asthma.

International patent applications WO 90/05525, WO 90/05729, WO 91/09844 and WO 91/18899 and European patent applications EP-A-0436334, EP-A-0429466 and EP-A-0430771 describe substance P antagonists.

European patent applications EP-A-0474561, EP-A-512901, EP-A-515240, EP-A-559538 and EP-A-591040 also relate to neurokinin receptor antagonists.

Novel substituted heterocyclic compounds have now been found which are neurokinin receptor antagonists.

Thus, according to one of its features, the present invention relates to compounds of the formula

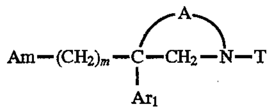

(I)

in which:

A is a divalent radical selected from:

$A_1$) —O—CO—

$A_2$) —$CH_2$—O—CO—

$A_3$) —O—$CH_2$—CO—

$A_4$) —O—$CH_2$—$CH_2$—

$A_5$) —N($R_1$)—CO—

$A_6$) —N($R_1$)—CO—CO—

$A_7$) —N($R_1$)—$CH_2$—$CH_2$—

$A_8$) —O—$CH_2$— in which $R_1$ is a hydrogen or a ($C_1$–$C_4$)-alkyl;

m is 2 or 3;

$Ar_1$ is a phenyl which is unsubstituted or monosubstituted or polysubstituted by a substituent selected from a halogen atom, a hydroxyl, a ($C_1$–$C_4$)-alkoxy, a ($C_1$–$C_4$)-alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a ($C_1$–$C_4$)-alkyl or a benzyl; an imidazolyl which is unsubstituted or substituted by a halogen atom; a pyridyl which is unsubstituted or substituted by a halogen atom; or a biphenyl;

T is a group selected from $CH_2$—Z, —CH($C_6H_5$)$_2$ and —C($C_6H_5$)$_3$; T can also be the group —CO—B—Z if A is a divalent radical selected from —O—$CH_2$—$CH_2$—, —N($R_1$)—$CH_2$—$CH_2$— and —O—$CH_2$—;

B is a direct bond or a methylene;

Z is an optionally substituted mono-, di- or tri- cyclic aromatic or heteroaromatic group; and Am is:

i—either a group $Am_1$ of the formula

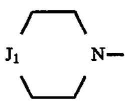

in which $J_1$ is:

$i_1$—either a group

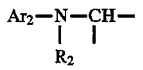

in which:

$Ar_2$ is a pyridyl; a phenyl which is unsubstituted or monosubstituted or polysubstituted by a substituent selected from a halogen atom, a hydroxyl, a ($C_1$–$C_4$)-alkoxy, a ($C_1$–$C_4$)-alkyl, a trifluoromethyl, a nitro and a methylenedioxy, said substituents being identical or different; a thienyl; a pyrimidyl; or an imidazolyl which is unsubstituted or substituted by a ($C_1$–$C_4$)-alkyl; and $R_2$ is a hydrogen; a ($C_1$–$C_7$)-alkyl; a benzyl; a formyl; or a ($C_1$–$C_7$)-alkylcarbonyl;

$i_2$—or a group

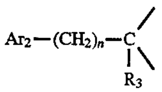

in which:

$Ar_2$ is as defined above;

n is 0 or 1; and $R_3$ is a group selected from:

(1) hydrogen;
(2) $(C_1-C_7)$-alkyl;
(3) formyl;
(4) $(C_1-C_7)$-alkylcarbonyl;
(5) cyano;
(6) $-(CH_2)_q-OH$;
(7) $-(CH_2)_q-O-(C_1-C_7)$-alkyl;
(8) $-(CH_2)_q-OCHO$;
(9) $-(CH_2)_q-OCOR_{17}$;
(10) $-(CH_2)_q-OCONH-(C_1-C_7)$-alkyl;
(11) $-NR_4R_5$;
(12) $-(CH_2)_q-NR_6C(=W_1)R_7$;
(13) $-(CH_2)_q-NR_6COOR_8$;
(14) $-(CH_2)_q-NR_6SO_2R_9$;
(15) $-(CH_2)_q-NR_6C(=W_1)NR_{10}R_{11}$;
(16) $-CH_2-NR_{12}R_{13}$;
(17) $-CH_2-CH_2-NR_{12}R_{13}$;
(18) $-COOH$;
(19) $(C_1-C_7)$-alkoxycarbonyl;
(20) $-C(=W_1)NR_{10}R_{11}$;
(21) $-CH_2-COOH$;
(22) $(C_1-C_7)$-alkoxycarbonylmethyl;
(23) $-CH_2-C(=W_1)NR_{10}R_{11}$;
(24) $-O-CH_2CH_2-OR_{18}$;
(25) $-NR_6COCOR_{19}$;
(26) $-CO-NR_{20}-NR_{21}R_{22}$;
(27)

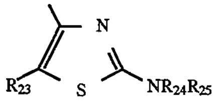
;

(28)

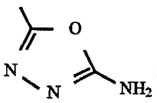
;

or $R_3$ constitutes a double bond between the carbon atom to which it is bonded and the adjacent carbon atom of the piperidine ring;

q is 0, 1 or 2;

$W_1$ is an oxygen atom or a sulfur atom;

$R_4$ and $R_5$ are each independently a hydrogen or a $(C_1-C_7)$-alkyl; $R_5$ can also be a $(C_3-C_7)$-cycloalkylmethyl, a benzyl or a phenyl; or $R_4$ and $R_5$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_6$ is a hydrogen or a $(C_1-C_7)$-alkyl;

$R_7$ is a hydrogen; a $(C_1-C_7)$-alkyl; a vinyl; a phenyl; a benzyl; a pyridyl; a $(C_3-C_7)$-cycloalkyl which is unsubstituted or substituted by one or more methyls; a furyl; a thienyl; a pyrrolyl; or an imidazolyl;

or $R_6$ and $R_7$ together are a group $-(CH_2)_p-$;

p is 3 or 4;

$R_8$ is a $(C_1-C_7)$-alkyl or a phenyl;

$R_9$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

$R_{10}$ and $R_{11}$ are each independently a hydrogen or a $(C_1-C_7)$-alkyl; $R_{11}$ can also be a $(C_3-C_7)$-cycloalkyl, a $(C_3-C_7)$-cycloalkylmethyl, a hydroxyl, a $(C_1-C_4)$-alkoxy, a benzyl or a phenyl; or $R_{10}$ and $R_{11}$, together with the nitrogen atom to which they are bonded, form a heterocycle selected from azetidine, pyrrolidine, piperidine, morpholine, thiomorpholine and perhydroazepine;

$R_{12}$ and $R_{13}$ are each independently a hydrogen or a $(C_1-C_7)$-alkyl; $R_{13}$ can also be a $(C_3-C_7)$-cycloalkylmethyl or a benzyl;

$R_{17}$ is a $(C_1-C_7)$-alkyl; a $(C_3-C_7)$-cycloalkyl which is unsubstituted or substituted by one or more methyls; a phenyl; or a pyridyl;

$R_{18}$ is a hydrogen; a $(C_1-C_7)$-alkyl; a formyl; or a $(C_1-C_7)$-alkylcarbonyl;

$R_{19}$ is a $(C_1-C_4)$-alkoxy;

$R_{20}$ is a hydrogen or a $(C_1-C_7)$-alkyl;

$R_{21}$ and $R_{22}$ are each independently a hydrogen or a $(C_1-C_7)$-alkyl;

or alternatively $R_{21}$ and $R_{22}$, together with the nitrogen atom to which they are bonded, form a heterocycle selected from pyrrolidine, piperidine and morpholine;

$R_{23}$ is a hydrogen or a $(C_1-C_7)$-alkyl; and $R_{24}$ and $R_{25}$ are each independently a hydrogen or a $(C_1-C_7)$-alkyl; $R_{25}$ can also be a formyl or a $(C_1-C_7)$-alkylcarbonyl;

$i_3$—or a group

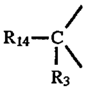

in which:

$R_3$ is as defined above;

$R_{14}$ is a $(C_1-C_7)$-alkyl or a $(C_3-C_7)$-cycloalkyl; $R_{14}$ can also be either a group $-CONR_{15}R_{16}$ if $R_3$ is hydrogen, or a group $-NR_{15}R_{16}$ if $R_3$ is hydrogen, a cyano, a carboxyl, a $(C_1-C_7)$-alkoxycarbonyl or a group $-C(=W_1)NR_{10}R_{11}$; and $R_{15}$ and $R_{16}$ are each independently a $(C_1-C_7)$-alkyl; or $R_{15}$ and $R_{16}$, together with the nitrogen atom to which they are bonded, form a heterocycle selected from azetidine, pyrrolidine, piperidine, morpholine, thiomorpholine and perhydroazepine;

ii—or a group $Am_2$ of the formula

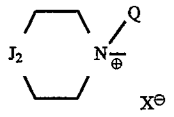

in which $J_2$ is:

$ii_1$—either a group

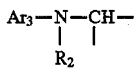

in which:

$Ar_3$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and $R_2$ is as defined above for $J_1$;

$ii_2$—or a group

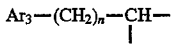

in which:

$Ar_3$ is as defined above;

n is 0 or 1;

Q is a $(C_1-C_6)$-alkyl or a benzyl, said substituent being either in the axial position or in the equtorial position; and $X^{\ominus}$ is an anion;

iii—or a group $Am_3$ of the formula

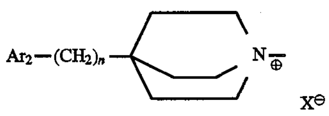

in which:

$Ar_2$ is as defined above;

n is 0 or 1; and $X^{\ominus}$ is an anion;

iv—or a group $Am_4$ of the formula

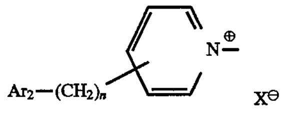

in which:

$Ar_2$ is as defined above;

n is 0 or 1; and $X^{\ominus}$ is an anion;

and the salts thereof, where appropriate, with mineral or organic acids.

The compounds of formula (I) according to the invention also include the racemates, the optically pure isomers and the axial and equatorial isomers if Am is $Am_2$ in the compound of formula (I).

More particularly, the radical Z can be a phenyl group which can be unsubstituted or may contain one or more substituents.

If Z is a phenyl group, it can be monosubstituted or disubstituted, especially in the 2,4-position but also, for example, in the 2,3-, 4,5-, 3,4- or 3,5-position; it can also be trisubstituted, especially in the 2,4,6-position but also, for example, in the 2,3,4-, 2,3,5-, 2,4,5- or 3,4,5-position, tetrasubstituted, for example in the 2,3,4,5-position, or pentasubstituted.

The radical Z can also be a bicyclic aromatic group such as 1- or 2-naphthyl; or 1-, 2-, 3-, 4-, 5-, 6- or 7-indenyl in which one or more bonds can be hydrogenated, it being possible for said groups to be unsubstituted or optionally to contain one or more substituents such as the alkyl, phenyl, cyano, hydroxyalkyl, hydroxyl, oxo, alkylcarbonylamino, alkoxycarbonyl, thioalkyl, halogen, alkoxy or trifluoromethyl group, in which the alkyls are $C_1-C_4$.

The radical Z can also be a pyridyl, thiadiazolyl, indolyl, indazolyl, imidazolyl, benzimidazolyl, benzotriazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl or chromanyl group, in which one or more double bonds can be hydrogenated, it being possible for said groups to be unsubstituted or optionally to contain one or more substituents such as the alkyl, phenyl, cyano, hydroxyalkyl, hydroxyl, alkylcarbonylamino, alkoxycarbonyl or thioalkyl group, in which the alkyls are $C_1-C_4$.

In particular, the invention relates to compounds of formula (I) in which:

Z is Z' and is:

a phenyl which is unsubstituted or monosubstituted or polysubstituted by a substituent selected from a halogen atom; a trifluoromethyl; a cyano; a hydroxyl; a nitro; a phenyl which is unsubstituted or monosubstituted or polysubstituted by a halogen, a trifluoromethyl, a $(C_1-C_4)$-alkyl, a hydroxyl or a $(C_1-C_4)$-alkoxy, said substituents being identical or different; an amino which is unsubstituted or monosubstituted or polysubstituted by a $(C_1-C_4)$-alkyl; a benzylamino; a carboxyl; a $(C_1-C_{10})$-alkyl; a $(C_3-C_8)$-cycloalkyl which is unsubstituted or monosubstituted or polysubstituted by a methyl; a $(C_1-C_{10})$-alkoxy; a $(C_3-C_8)$-cycloalkoxy which is unsubstituted or mono-substituted or polysubstituted by a methyl; a mercapto; a $(C_1-C_{10})$-alkylthio; a formyloxy; a $(C_1-C_6)$-alkylcarbonyloxy; a formylamino; a $(C_1-C_6)$-alkylcarbonylamino; a benzoylamino; a $(C_1-C_6)$-alkoxycarbonyl; a $(C_3-C_7)$-cycloalkoxycarbonyl; a $(C_3-C_7)$-cycloalkylcarbonyl; a carbamoyl which is unsubstituted or mono-substituted or disubstituted by a $(C_1-C_4)$-alkyl; a ureido which is unsubstituted or monosubstituted or disubstituted in the 3-position by a $(C_1-C_4)$-alkyl or a $(C_3-C_7)$-cycloalkyl; and a (pyrrolidin-1-yl)-carbonylamino, said substituents being identical or different;

a naphthyl which is unsubstituted or monosubstituted or polysubstituted by a halogen, a trifluoro-methyl, a $(C_1-C_4)$-alkyl, a hydroxyl or a $(C_1-C_4)$-alkoxy; or a pyridyl, a thienyl, an indolyl, a quinolyl, a benzothienyl or an imidazolyl.

It is possible to form salts of the compounds of formula (I) other than the quaternary ammonium salts. These salts include those with mineral and organic acids which permit a suitable separation or crystallization of the compounds of formula (I), such as picric acid, oxalic acid or an optically active acid, for example a mandelic or camphosulfonic acid, and mineral and organic acids which form pharmaceutically acceptable salts such as the hydrochloride, hydrobromide, sulfate, hydrogensulfate, dihydrogenphosphate, methanesulfonate, methylsulfate, maleate, fumarate, naphthalene-2-sulfonate, benzenesulfonate, gluconate, citrate, isethionate, or p-toluenesulfonate.

The anions $X^{\ominus}$ are those normally used to salify quaternary ammonium ions and are preferably chloride, bromide, iodide, acetate, hydrogensulfate, methanesulfonate, paratoluenesulfonate and benzenesulfonate ions.

It is preferable to use the pharmaceutically acceptable anions, for example chloride, methanesulfonate or benzenesulfonate.

In the present description, the alkyl groups or alkoxy groups are linear or branched; halogen atom is understood as meaning a chlorine, bromine, fluorine or iodine atom.

In the substituents of the group Z=phenyl, $(C_1-C_{10})$-alkyl is understood as meaning for example a methyl, an ethyl, an n-propyl, an isopropyl, an n-butyl, an isobutyl, a sec-butyl, a tert-butyl, a pentyl or n-pentyl, a hexyl or n-hexyl, a heptyl or n-heptyl, an octyl or n-octyl, a nonyl or n-nonyl or a decyl or n-decyl; $(C_3-C_8)$-cycloalkyl optionally substituted by a methyl is understood as meaning for example a cyclopropyl, a cyclobutyl, a cyclopentyl, a 1-, 2- or 3-methylcyclopentyl, a cyclohexyl, a 1-, 2-, 3- or 4-methylcyclohexyl, a cycloheptyl or a cyclooctyl; $(C_1-C_{10})$-alkoxy is understood as meaning for example a methoxy, an ethoxy, an n-propoxy, an isopropoxy, an n-butoxy, an isobutoxy, a sec-butoxy, a tert-butoxy, a pentoxy, a hexyloxy, a heptyloxy, a nonyloxy or a decyloxy; $(C_3-C_8)$-cycloalkoxy optionally substituted by a methyl is understood as meaning for example a cyclopropoxy, a cyclohexyloxy, a 1-, 2-, 3- or 4-methylcyclohexyloxy, a cycloheptyloxy or a cyclooctyloxy; $(C_1-C_{10})$-alkylthio is understood as meaning for example a methylthio, an ethylthio, an n-propylthio, an isopropylthio, an n-butylthio, an isobutylthio, a secbutylthio, a tert-butylthio, a pentylthio, a hexylthio, a heptylthio, an octylthio, a nonylthio or a decylthio; $(C_1-C_6)$-alkylcarbonyloxy is understood as meaning for example an acetoxy, a propionyloxy, a butyryloxy, a valeryloxy, a caproyloxy or a heptanoyloxy; $(C_1-C_6)$-alkylcarbonylamino is understood as meaning for example an acetylamino, a propionylamino, a butyrylamino, an isobutyrylamino, a valerylamino, a caproylamino or a heptanoylamino; $(C_1-C_4)$-alkoxycarbonyl is understood as meaning for example a methoxycarbonyl, an ethoxycarbonyl, an n-propoxycarbonyl, an isopropoxycarbonyl, an n-butoxycarbonyl, an isobutoxycarbonyl, a sec-butoxycarbonyl or a tert-butoxycarbonyl; and $(C_3-C_7)$-cycloalkoxycarbonyl is understood as meaning for example a cyclopropoxycarbonyl, a cyclobutoxycarbonyl, a cyclopentoxycarbonyl, a cyclohexyloxycarbonyl or a cycloheptyloxycarbonyl.

Advantageously, the radical Z is a phenyl which is unsubstituted or monosubstituted or polysubstituted by a halogen atom, more particularly a chlorine, fluorine or iodine atom, a trifluoromethyl, a $(C_1-C_4)$-alkyl, a hydroxyl or a $(C_1-C_4)$-alkoxy; a naphthyl which is unsubstituted or monosubstituted or polysubstituted by a halogen, a trifluoromethyl, a $(C_1-C_4)$-alkyl, a hydroxyl or a $(C_1-C_4)$-alkoxy; a pyridyl; a thienyl; an indolyl; a quinolyl; a benzothienyl; or an imidazolyl.

According to the present invention, the preferred compounds are those of formula (I) in which:

A is a divalent radical selected from:

$A_1$) —O—CO—

$A_2$) —$CH_2$—O—CO—

$A_3$) —O—$CH_2$—CO—

$A_4$) —O—$CH_2$—$CH_2$—

$A_5$) —N($R_1$)—CO—

$A_6$) —N($R_1$)—CO—CO—

$A_7$) —N($R_1$)—$CH_2$—$CH_2$— in which:

$R_1$ is a hydrogen or a $(C_1-C_4)$-alkyl; and

Am is:

i—either a group $Am_1$ of the formula

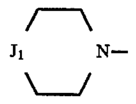

in which $J_1$ is:

$i_1$—either a group

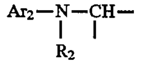

in which:

$Ar_2$ is a pyridyl; or a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and $R_2$ is a hydrogen; a $(C_1-C_7)$-alkyl; a benzyl; a formyl; or a $(C_1-C_7)$-alkylcarbonyl;

$i_2$—or a group

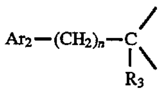

in which:

$Ar_2$ is as defined above;

n is 0 or 1;

$R_3$ is a hydrogen; a $(C_1-C_7)$-alkyl; a formyl; a $(C_1-C_7)$-alkylcarbonyl; a cyano; a group —$(CH_2)_q$—OH; a group $(C_1-C_7)$-alkyl-O—$(CH_2)_q$—; a group HCOO—$(CH_2)_q$—; a group $(C_1-C_7)$-alkyl-COO—$(CH_2)_q$—; a group $(C_1-C_7)$-alkyl-NHCOO—$(CH_2)_q$—; a group —$NR_4R_5$; a group —$(CH_2)_q$—$NR_6COR_7$; a group —$(CH_2)_q$—$NR_6COOR_8$; a group —$(CH_2)_q$—$NR_6SO_2R_9$; a group -($CH_2$)—$NR_6CONR_{10}R_{11}$; a group —$CH_2$—$NR_{12}R_{13}$; a group —$CH_2$—$CH_2$—$NR_{12}R_{13}$; a carboxyl; a $(C_1-C_7)$-alkoxycarbonyl; a group —$CONR_{10}R_{11}$; a carboxymethyl; a $(C_1-C_7)$-alkoxycarbonylmethyl; a group —$CH_2$—$CONR_{10}R_{11}$; or a 2-aminothiazol-4-yl in which the amino is free or substituted by one or two $(C_1-C_7)$-alkyls;

or $R_3$ constitutes a double bond between the carbon atom to which it is bonded and the adjacent carbon atom of the piperidine ring;

q is 0, 1 or 2;

$R_4$ and $R_5$ are each independently a hydrogen or a $(C_1-C_7)$-alkyl; $R_5$ can also be a $(C_3-C_7)$-cycloalkylmethyl, a benzyl or a phenyl; or $R_4$ and $R_5$, together with the nitrogen atom to which they are bonded, form a heterocycle selected from azetidine, pyrrolidine, piperidine, morpholine, thiomorpholine and perhydroazepine;

$R_6$ is a hydrogen or a $(C_1$–$C_4)$-alkyl;

$R_7$ is a hydrogen; a $(C_1$–$C_7)$-alkyl; a vinyl; a phenyl; a benzyl; a pyridyl; or a $(C_3$—$C_7)$-cycloalkyl which is unsubstituted or substituted by one or more methyls;

or $R_6$ and $R_7$ together are a group $—(CH_2)_p—$;

p is 3 or 4;

$R_8$ is a $(C_1$–$C_7)$-alkyl or a phenyl;

$R_9$ is a $(C_1$–$C_7)$-alkyl; an amino which is free or substituted by one or two $(C_1$–$C_7)$-alkyls; or a phenyl which is unsubstituted or monosubstituted or polysubstituted by a substituent selected from a halogen atom, a $(C_1$–$C_7)$-alkyl, a trifluoromethyl, a hydroxyl, a $(C_1$–$C_7)$-alkoxy, a carboxyl, a $(C_1$–$C_7)$-alkoxycarbonyl, a $(C_1$–$C_7)$-alkylcarbonyloxy, a cyano, a nitro and an amino which is free or substituted by one or two $(C_1$–$C_7)$-alkyls, said substituents being identical or different;

$R_{10}$ and $R_{11}$ are each independently a hydrogen or a $(C_1$–$C_7)$-alkyl; $R_{11}$ can also be a $(C_3$–$C_7)$-cycloalkyl, a $(C_3$–$C_7)$-cycloalkylmethyl, a hydroxyl, a $(C_1$–$C_4)$-alkoxy, a benzyl or a phenyl; or $R_{10}$ and $R_{11}$, together with the nitrogen atom to which they are bonded, form a heterocycle selected from azetidine, pyrrolidine, piperidine, morpholine, thiomorpholine and perhydroazepine; and $R_{12}$ and $R_{13}$ are each independently a hydrogen or a $(C_1$–$C_7)$-alkyl; $R_{13}$ can also be a $(C_3$–$C_7)$-cycloalkylmethyl or a benzyl;

$i_3$—or a group

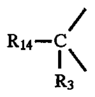

in which:

$R_3$ is as defined above;

$R_{14}$ is a $(C_1$–$C_7)$-alkyl or a $(C_3$—$C_7)$-cycloalkyl; $R_{14}$ can also be either a group $—CONR_{15}R_{16}$ if $R_3$ is hydrogen, or a group $—NR_{15}R_{16}$ if $R_3$ is a cyano, a carboxyl, a $(C_1$–$C_7)$-alkoxycarbonyl or a group $—CONR_{10}R_{11}$; and $R_{15}$ and $R_{16}$ are each independently a $(C_1$–$C_7)$-alkyl; or $R_{15}$ and $R_{16}$, together with the nitrogen atom to which they are bonded, form a heterocycle selected from azetidine, pyrrolidine, piperidine, morpholine, thiomorpholine and perhydroazepine;

ii—or a group $Am_2$ of the formula

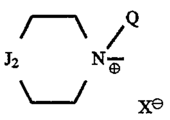

in which $J_2$ is:

$ii_1$—either a group

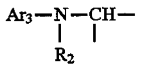

in which:

$Ar_3$ is a phenyl which is unsubstituted or monosubstituted or polysubstituted by a substituent selected from a halogen atom, a hydroxyl, a $(C_1$–$C_4)$-alkoxy, a $(C_1$–$C_4)$-alkyl and a trifluoromethyl, said substituents being identical or different; and $R_2$ is as defined above for $J_1$;

$ii_2$—or a group

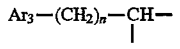

in which:

$Ar_3$ is as defined above;

n is 0 or 1;

Q is a $(C_1$–$C_6)$-alkyl or a benzyl, said substituent being either in the axial position or in the equatorial position; and $X^{\ominus}$ is an anion;

iii—or a group $Am_3$ of the formula

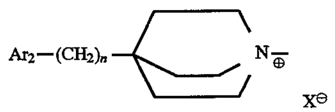

in which:

$Ar_2$ is as defined above;

n is 0 or 1; and $X^{\ominus}$ is an anion;

iv—or a group $Am_4$ of the formula

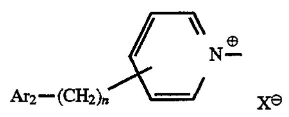

in which:

$Ar_2$ is as defined above;

n is 0 or 1;

$X^{\ominus}$ is an anion;

m is 2 or 3;

$Ar_1$ is a phenyl which is unsubstituted or monosubstituted or polysubstituted by a substituent selected from a halogen atom, a hydroxyl, a $(C_1$–$C_4)$-alkoxy, a $(C_1$–$C_4)$-alkyl and a trifluoromethyl, said substituents being identical or different; a thienyl; a benzothienyl; a naphthyl; or an indolyl which is unsubstituted or N-substituted by a $(C_1$–$C_4)$-alkyl or a benzyl;

T is a group selected from $—CH_2—Z$, $—CH(C_6H_5)_2$ and $—C(C_6H_5)_3$; T can also be the group —CO—B—Z if A is a divalent radical selected from $—O—CH_2CH_2—$ and $—N(R_1)—CH_2—CH_2—$;

B is a direct bond or a methylene; and

Z is:

a phenyl which is unsubstituted or monosubstituted or polysubstituted by a substituent selected from a halogen atom; a trifluoromethyl; a cyano; a hydroxyl; a nitro; a phenyl which is unsubstituted or monosubstituted or polysubstituted by a halogen, a trifluoromethyl, a $(C_1$–$C_4)$-alkyl, a hydroxyl or a $(C_1$–$C_4)$-alkoxy, said substituents being identical or different; an amino which is unsubstituted or monosubstituted or disubstituted by a $(C_1$–$C_4)$-alkyl; a benzylamino; a carboxyl; a $(C_1$–$C_{10})$-alkyl; a $(C_3$–$C_7)$-cycloalkyl which is unsubstituted or monosubstituted or polysubstituted by a methyl; a $(C_1$–$C_{10})$-alkoxy; a $(C_3$–$C_7)$-cycloalkoxy which is unsubstituted or mono-substituted or polysubstituted by a methyl; a mercapto; a $(C_1-C_{10})$-alkylthio; a $(C_1-C_6)$-alkylcarbonyloxy; a $(C_1-C_6)$-alkylcarbonylamino; a benzoylamino; a $(C_1-C_4)$-alkoxycarbonyl; a $(C_3-C_7)$-cycloalkylcarbonyl; a carbamoyl which is unsubstituted or monosubstituted or disubstituted by a $(C_1-C_4)$-alkyl; a ureido which is unsubstituted or monosubstituted or disubstituted in the 3-position by a $(C_1-C_4)$-alkyl or a $(C_3-C_7)$-cycloalkyl; and a (pyrrolidin-1-yl)carbonylamino, said substituents being identical or different;

a naphthyl which is unsubstituted or monosubstituted or polysubstituted by a halogen, a trifluoromethyl, a $(C_1-C_4)$-alkyl, a hydroxyl or a $(C_1-C_4)$-alkoxy; or a pyridyl, a thienyl, an indolyl, a quinolyl, a benzothienyl or an imidazolyl;

and the salts thereof, where appropriate, with mineral or organic acids.

The compounds also preferred are those of formula (I) in which:

A is a divalent radical selected from:

$A_1$) —O—CO—

$A_2$) —$CH_2$—O—CO—

$A_3$) —O—$CH_2$—CO—

$A_4$) —O—$CH_2$—$CH_2$—

$A_5$) —N($R_1$)—CO—

$A_6$) —N($R_1$)—CO—CO—

$A_7$) —N($R_1$)—$CH_2$—$CH_2$— in which $R_1$ is a hydrogen or a $(C_1-C_4)$-alkyl;

m is 2 or 3;

$Ar_1$ is a phenyl which is unsubstituted or monosubstituted or polysubstituted by a substituent selected from a halogen atom, a hydroxyl, a $(C_1-C_4)$-alkoxy, a $(C_1-C_4)$-alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a $(C_1-C_4)$-alkyl or a benzyl; an imidazolyl which is unsubstituted or substituted by a halogen atom; a pyridyl which is unsubstituted or substituted by a halogen atom; or a biphenyl;

T is a group selected from $CH_2$—Z, —CH$(C_6H_5)_2$ and —C$(C_6H_5)_3$; T can also be the group —CO—B—Z if A is a divalent radical selected from —O—$CH_2$—$CH_2$— and —N($R_1$)—$CH_2$—$CH_2$—;

B is a direct bond or a methylene;

Z is an optionally substituted mono-, di- or tricyclic aromatic or heteroaromatic group; and Am is:

i—either a group $Am_1$ of the formula

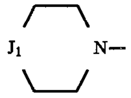

in which $J_1$ is:

$i_1$—either a group

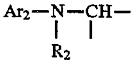

in which:

$Ar_2$ is a pyridyl; a phenyl which is unsubstituted or monosubstituted or polysubstituted by a substituent selected from a halogen atom, a hydroxyl, a $(C_1-C_4)$-alkoxy, a $(C_1-C_4)$-alkyl, a trifluoromethyl, a nitro and a methylenedioxy, said substituents being identical or different; a thienyl; a pyrimidyl; or an imidazolyl which is unsubstituted or substituted by a $(C_1-C_4)$-alkyl; and $R_2$ is a hydrogen; a $(C_1-C_7)$-alkyl; a benzyl; a formyl; or a $(C_1-C_7)$-alkylcarbonyl;

$i_2$—or a group

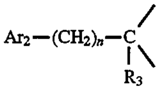

in which:

$Ar_2$ is as defined above;

n is 0 or 1; and $R_3$ is a group selected from:

(1) hydrogen;

(2) $(C_1-C_7)$-alkyl;

(3) formyl;

(4) $(C_1-C_7)$-alkylcarbonyl;

(5) cyano;

(6) —$(CH_2)_q$—OH;

(7) —$(CH_2)_q$—O—$(C_1-C_7)$-alkyl;

(8) —$(CH_2)_q$—OCHO;

(9) —$(CH_2)_q$—$OCOR_{17}$;

(10) —$(CH_2)_q$—OCONH—$(C_1-C_7)$-alkyl;

(11) —$NR_4R_5$;

(12) —$(CH_2)_q$—$NR_6C(=W_1)R_7$;

(13) —$(CH_2)_q$—$NR_6COOR_8$;

(14) —$(CH_2)_q$—$NR_6SO_2R_9$;

(15) —$(CH_2)_q$—$NR_6C(=W_1)NR_{10}R_{11}$;

(16) —$CH_2$—$NR_{12}R_{13}$;

(17) —$CH_2$—$CH_2$—$NR_{12}R_{13}$;

(18) —COOH;

(19) $(C_1-C_7)$-alkoxycarbonyl;

(20) —$C(=W_1)NR_{10}R_{11}$;

(21) —$CH_2$—COOH;

(22) $(C_1-C_7)$-alkoxycarbonylmethyl;

(23) —$CH_2$—$C(=W_1)NR_{10}R_{11}$;

(24) —O—$CH_2CH_2$—$OR_{18}$;

(25) —$NR_6COCOR_{19}$;

(26) —CO—$NR_{20}$—$NR_{21}R_{22}$;

(27)

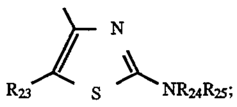

(28)

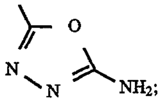

or $R_3$ constitutes a double bond between the carbon atom to which it is bonded and the adjacent carbon atom of the piperidine ring;

q is 0, 1 or 2;

$W_1$ is an oxygen atom or a sulfur atom;

$R_4$ and $R_5$ are each independently a hydrogen or a $(C_1-C_7)$-alkyl; $R_5$ can also be a $(C_3-C_7)$- cycloalkylmethyl, a benzyl or a phenyl; or $R_4$ and $R_5$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_6$ is a hydrogen or a $(C_1-C_4)$-alkyl;

$R_7$ is a hydrogen; a $(C_1-C_7)$-alkyl; a vinyl; a phenyl; a benzyl; a pyridyl; a $(C_3-C_7)$-cycloalkyl which is unsubstituted or substituted by one or more methyls; a furyl; a thienyl; a pyrrolyl; or an imidazolyl;

or $R_6$ and $R_7$ together are a group $-(CH_2)_p-$;

p is 3 or 4;

$R_8$ is a $(C_1-C_7)$-alkyl or a phenyl;

$R_9$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

$R_{10}$ and $R_{11}$ are each independently a hydrogen or a $(C_1-C_7)$-alkyl; $R_{11}$ can also be a $(C_3-C_7)$-cycloalkyl, a $(C_3-C_7)$-cycloalkylmethyl, a hydroxyl, a $(C_1-C_4)$-alkoxy, a benzyl or a phenyl; or $R_{10}$ and $R_{11}$, together with the nitrogen atom to which they are bonded, form a heterocycle selected from azetidine, pyrrolidine, piperidine, morpholine, thiomorpholine and perhydroazepine;

$R_{12}$ and $R_{13}$ are each independently a hydrogen or a $(C_1-C_7)$-alkyl; $R_{13}$ can also be a $(C_3-C_7)$-cycloalkylmethyl or a benzyl;

$R_{17}$ is a $(C_1-C_7)$-alkyl; a $(C_3-C_7)$-cycloalkyl which is unsubstituted or substituted by one or more methyls; a phenyl; or a pyridyl;

$R_{18}$ is a hydrogen; a $(C_1-C_7)$-alkyl; a formyl; or a $(C_1-C_7)$-alkylcarbonyl;

$R_{19}$ is a $(C_1-C_4)$-alkoxy;

$R_{20}$ is a hydrogen or a $(C_1-C_7)$-alkyl;

$R_{21}$ and $R_{22}$ are each independently a hydrogen or a $(C_1-C_7)$-alkyl;

or alternatively $R_{21}$ and $R_{22}$, together with the nitrogen atom to which they are bonded, form a heterocycle selected from pyrrolidine, piperidine and morpholine;

$R_{23}$ is a hydrogen or a $(C_1-C_7)$-alkyl; and $R_{24}$ and $R_{25}$ are each independently a hydrogen or a $(C_1-C_7)$-alkyl; $R_{25}$ can also be a formyl or a $(C_1-C_7)$-alkylcarbonyl;

$i_3$—or a group

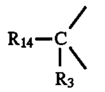

in which:

$R_3$ is as defined above;

$R_{14}$ is a $(C_1-C_7)$-alkyl or a $(C_3-C_7)$-cycloalkyl; can also be either a group $-CONR_{15}R_{16}$ if $R_3$ is hydrogen, or a group $-NR_{15}R_{16}$ if $R_3$ is a cyano, a carboxyl, a $(C_1-C_7)$-alkoxycarbonyl or a group $-C(=W_1NR_{10}R_{11}$; and $R_{15}$ and $R_{16}$ are each independently a $(C_1-C_7)$-alkyl; or $R_{15}$ and $R_{16}$, together with the nitrogen atom to which they are bonded, form a heterocycle selected from azetidine, pyrrolidine, piperidine, morpholine, thiomorpholine and perhydroazepine;

ii—or a group $Am_2$ of the formula

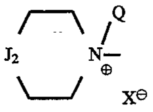

in which $J_2$ is:

$ii_1$—either a group

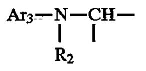

in which:

$Ar_3$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and $R_2$ is as defined above for $J_1$;

$ii_2$—or a group

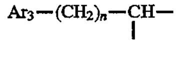

in which:

$Ar_3$ is as defined above;

n is 0 or 1;

Q is a $(C_1-C_6)$-alkyl or a benzyl, said substituent being either in the axial position or in the equatorial position; and $X^\ominus$ is an anion;

iii—or a group $Am_3$ of the formula

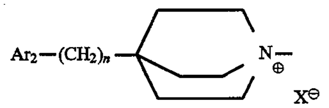

in which:

$Ar_2$ is as defined above;

n is 0 or 1; and $X^\ominus$ is an anion;

iv—or a group $Am_4$ of the formula

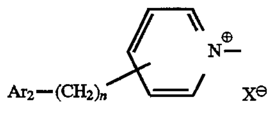

in which:

$Ar_2$ is as defined above;

n is 0 or 1; and $X^\ominus$ is an anion; and the salts thereof, where appropriate, with mineral or organic acids.

Another group of preferred compounds according to the present invention consists of those of the formula

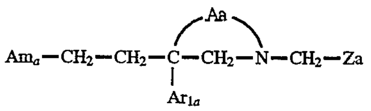

(Ia)

in which:

Aa is a divalent radical selected from —O—CO—; —$CH_2$—O—CO—; —O—$CH_2$—CO—; —N($R_1$)—CO— and —N($R_1$)—CO—CO—, in which $R_1$ is a hydrogen or a ($C_1$–$C_4$)-alkyl;

$Am_a$ is:

either a group $Am_{2a}$ of the formula

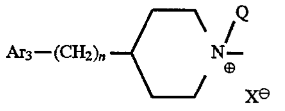

or a group $Am_3$ of the formula

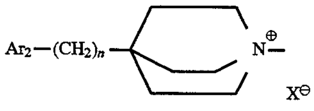

n is 0 or 1;

Q is as defined above for a compound of formula (I) and is in the axial position;

$X^{\ominus}$ is a pharmaceutically acceptable anion;

$Ar_2$ and $Ar_3$ are as defined above for a compound of formula (I);

$Ar_{1a}$ is a phenyl which is unsubstituted or monosubstituted or polysubstituted by a substituent selected from a halogen atom, a hydroxyl, a ($C_1$–$C_4$)-alkoxy, a ($C_1$–$C_4$)-alkyl and a trifluoromethyl, said substituents being identical or different; and Za is a phenyl which is unsubstituted or monosubstituted or polysubstituted by a substituent selected from a halogen atom, a trifluoromethyl, a ($C_1$–$C_{10}$)-alkyl, a ($C_1$–$C_{10}$)-alkoxy and a hydroxyl, said substituents being identical or different.

Among these compounds, those of the formula

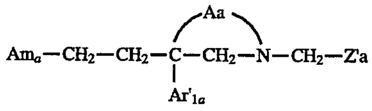

(I'a)

in which:

Aa and $Am_a$ are as defined above for a compound of formula (Ia);

$Ar'_{1a}$ is a 3,4-dichlorophenyl or a 3,4-difluorophenyl; and

Z'a is a 3,5-bis(trifluoromethyl)phenyl, a 3,5-dimethylphenyl or a 2,4-bis(trifluoromethyl)phenyl, are particularly preferred.

Another group of preferred compounds according to the invention consists of those of the formula

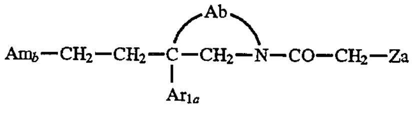

(Ib)

in which:

Ab is the divalent radical —O—$CH_2$—$CH_2$—, —N($R_1$)—$CH_2$—$CH_2$— or —O—$CH_2$—, in which $R_1$ is a hydrogen or a ($C_1$–$C_4$)-alkyl;

$Am_b$ is:

either a group $Am_{2a}$ of the formula

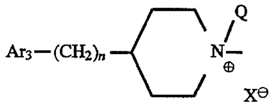

or a group $Am_3$ of the formula

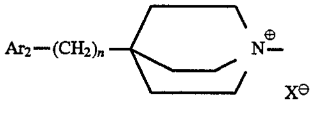

or a group $Am_{1a}$ of the formula

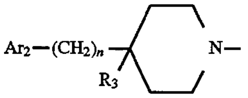

n is 0 or 1;

Q is as defined above for a compound of formula (I) and is in the axial position;

$X^{\ominus}$ is a pharmaceutically acceptable anion;

$Ar_2$, $Ar_3$ and $R_3$ are as defined above for a compound of formula (I); and $Ar_{1a}$ and Za are as defined above;

and the salts thereof with mineral or organic acids.

Among these compounds, those of the formula

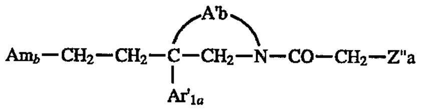

(I'b)

in which:

$Am_b$ is as defined above for a compound of formula (Ib);

A'b is the divalent radical —O—$CH_2$—$CH_2$— or —N($R_1$)—$CH_2$—$CH_2$—;

$Ar'_{1a}$ is as defined above for a compound of formula (I'a); and

Z"a is a phenyl substituted in the 3-position by a halogen or a ($C_1$–$C_{10}$)-alkoxy group, and the salts thereof with mineral or organic acids, are particularly preferred.

Another group of preferred compounds according to the invention consists of those of the formula

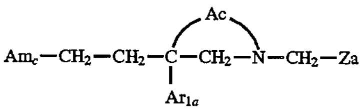

(Ic)

in which:

Ac is a divalent radical selected from —O—$CH_2$—CO—; —$CH_2$—O—CO— and —O—CO—;

$Am_c$ is a group $Am_{1a}$ of the formula

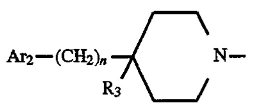

n is 0 or 1;

$Ar_2$ and $R_3$ are as defined above for a compound of formula (I); and $Ar_{1a}$ and Za are as defined above; and the salts thereof with mineral or organic acids.

Among these compounds, those of the formula

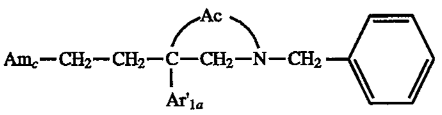

(I'c)

in which:

Ac, $Am_c$ and $Ar'_{1a}$ are as defined above, and the salts thereof with mineral or organic acids, are particularly preferred.

Another group of preferred compounds according to the invention consists of those of the formula

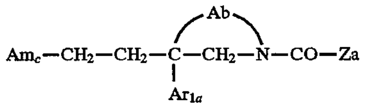

(Id)

in which:

Ab, $Am_c$, $Ar_{1a}$ and Za are as defined above; and the salts thereof with mineral or organic acids.

Among these compounds, those of the formula

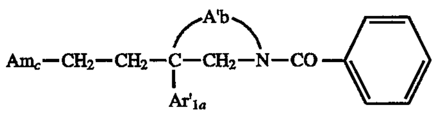

(I'd)

in which:

A'b, $Am_c$ and $Ar'_{1a}$ are as defined above, and the salts thereof with mineral or organic acids, are particularly preferred.

Among the compounds of formulae (Ia) and (I'a) above, those in which:

$Ar_2$ is a pyridyl; or a phenyl which is unsubstituted or monosubstituted or polysubsitiuted by a substituent selected from a halogen atom, a hydroxyl, a $(C_1$–$C_4)$-alkoxy, a $(C_1$–$C_4)$-alkyl and a trifluoromethyl, said substituents being identical or different; and the salts thereof with mineral or organic acids are particularly preferred.

Among the compounds of formulae (I'b), (Ic), (I'c) and (I'd) above, those in which:

$Ar_2$ is a pyridyl; or a phenyl which is unsubstituted or monosubstituted or polysubstituted by a substituent selected from a halogen atom, a hydroxyl, a $(C_1$–$C_4)$-alkoxy, a $(C_1$–$C_4)$-alkyl and a trifluoromethyl, said substituents being identical or different, and $R_3$ is a hydrogen; a $(C_1$–$C_7)$-alkyl; a formyl; a $(C_1$–$C_7)$-alkylcarbonyl; a cyano; a group $-(CH_2)_q-OH$; a group $(C_1$–$C_7)$-alkyl-O—$(CH_2)_q$—; a group HCOO—$(CH_2)_q$—; a group $(C_1$–$C_7)$-alkyl—COO—$(CH_2)_q$—; a group $(C_1$–$C_7)$-alkyl-NHCOO—$(C_2)_q$—; a group —$NR_4R_5$; a group —$(CH_2)_q$—$NR_6COR_7$; a group —$(CH_2)_q$—$NR_6COOR_8$; a group —$(CH_2)_q$—$NR_6SO_2R_9$; a group —$(CH_2)_q$—$NR_6CONR_{10}R_{11}$; a group —$CH_2$—$NR_{12}R_{13}$; a group —$CH_2$—$CH_2$—$NR_{12}R_{13}$; a carboxyl; a $(C_1$–$C_7)$-alkoxycarbonyl; a group —$CONR_{10}R_{11}$; a carboxymethyl; a $(C_1$–$C_7)$-alkoxycarbonylmethyl; a group —$CH_2$-$CONR_{10}R_{11}$; or a 2-aminothiazol-4-yl in which the amino is free or substituted by one or two $(C_1$–$C_7)$-alkyls;

or $R_3$ constitutes a double bond between the carbon atom to which it is bonded and the adjacent carbon atom of the piperidine ring;

q is 0, 1 or 2;

and the salts thereof, with mineral or organic acids, are particularly preferred.

Among the compounds of formulae (Ib) and (Id), those in which:

Ab is the divalent radical —O—$CH_2$—$CH_2$— or —$N(R_1)$—$CH_2$—$CH_2$—, $Ar_2$ is a pyridyl; or a phenyl which is unsubstituted or monosubstituted or polysubstituted by a substituent selected from a halogen atom, a hydroxyl, a $(C_1$–$C_4)$-alkoxy, a $(C_1$–$C_4)$-alkyl and a trifluoromethyl, said substituents being identical or different, and $R_2$ is a hydrogen; a $(C_1$–$C_7)$-alkyl; a formyl; a $(C_1$–$C_7)$-alkylcarbonyl; a cyano; a group $-(CH_2)_q-OH$; a group $(C_1$–$C_7)$-alkyl-O—$(CH_2)_q$—; a group HCOO—$(CH_2)_q$—; a group $(C_1$–$C_7)$-alkyl-COO—$(CH_2)_q$—; a group $(CH_1$–$C_7)$-alkyl-NHCOO—$(CH_2)_q$—; a group -$NR_4R_5$; a group —$(CH_2)_q$—$NR_4COR_7$; a group —$(CH_2)_q$—$NR_6COOR_8$; a group —$(CH_2)_q$—$NR_6SO_2R_9$; a group —$(CH_2)_q$—$NR_6CONR_{10}R_{11}$; a group —$CH_2$—$NR_{12}R_{13}$; a group —$CH_2$—$CH_2$—$NR_{12}R_{13}$; a carboxyl; a $(C_1$–$C_7)$-alkoxycarbonyl; a group —$CONR_{10}R_{11}$; a carboxymethyl; a $(C_1$–$C_7)$-alkoxycarbonylmethyl; a group —$CH_2$—$CONR_{10}R_{11}$; or a 2-aminothiazol-4-yl in which the amino is free or substituted by one or two $(C_1$–$C_7)$-alkyls;

or $R_3$ constitutes a double bond between the carbon atom to which it is bonded and the adjacent carbon atom of the piperidine ring;

q is 0, 1 or 2;

and the salts thereof, with mineral or organic acids, are particularly preferred.

Another group of preferred compounds according to the invention consists of those of the formula

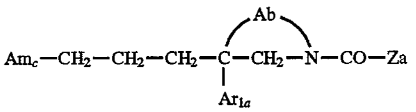

(Ie)

in which

Ab, $Am_C$, $Ar_{1a}$ and Za are as defined above; and the salts thereof with mineral or organic acids.

Another group of preferred compounds according to the invention consists of those of the formula:

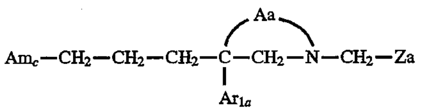

(If)

in which:

Aa, $Am_c$, $Ar_{1a}$ and Za are as defined above; and the salts thereof with mineral or organic acids.

4-Benzoyl-2-(3,4-difluorophenyl)-2-[2-[4-(N',N'-dimethylureido)-4-phenylpiperid-1-yl]ethyl]morpholine, in optically pure form, preferably in the form of the (+) isomer, and the salts thereof with mineral or organic acids, are very particularly preferred.

5-(3,4-Difluorophenyl)-5-[2-[4-phenyl-1-azoniabicyclo[2.2.2]oct-1-yl]ethyl]-3-[3,5-bis(trifluoromethyl)benzyl]oxazolidin-2-one with a pharmaceutically acceptable anion, in optically pure form, preferably in the form of the (+) isomer, is very particularly preferred.

According to another of its features, the present invention relates to a method of preparing the compounds of formula (I) and the salts thereof, which comprises:

1) treating a compound of the formula

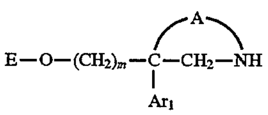

(II)

in which m, $Ar_1$ and A are as defined above for a compound of formula (I) and E is hydrogen or an O-protecting group, either with a functional derivative of an acid of the formula

HOCO—B—Z (III)

in which B and Z are as defined above for (I), if it is intended to prepare a compound of formula (I) in which T is —CO—B—Z, or with a halogenated derivative of the formula $Hal—CH_2—Z$ (IV)

in which Z is as defined above and Hal is a halogen, preferably bromine or chlorine, if it is intended to prepare a compound of formula (I) in which T is $—CH_2—Z$, or with a halogenated derivative of the formula $Hal—CH(C_6H_5)_2$ (V)

if it is intended to prepare a compound of formula (I) in which T is a group $—CH(C_6H_5)_2$, or with a halogenated derivative of the formula $Hal—C—(C_6H_5)_3$ (VI)

if it is intended to prepare a compound of formula (I) in which T is a group $—C(C_6H_5)_3$, to give a compound of the formula

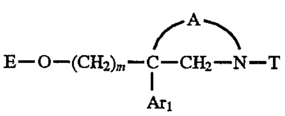

(VII)

2) optionally removing the O-protecting group by reaction with an acid or a base to give the alcohol of the formula

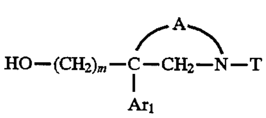

(VIII)

3) treating the alcohol (VIII) with a compound of the formula $Y—SO_2—Cl$ (IX)

in which Y is a methyl, phenyl, tolyl or trifluoromethyl group, to give a compound of the formula

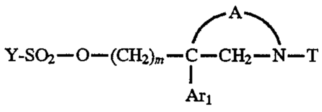

(X)

4) reacting the compound (X):

either with a cyclic secondary amine of the formula

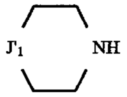

(XI)

in which $J'_1$ is:

either a group

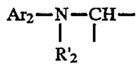

in which:

$Ar_2$ is as defined for (I) and $R'_2$ is either $R_2$ as defined for (I) or a precursor of $R_2$;

or a group

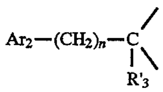

in which $Ar_2$ and n are as defined for (I) and $R'_3$ is either $R_3$ as defined for (I) or a precursor of $R_3$, it being understood that if $R'_3$ is a hydroxyl or an amino, these groups can be protected;

or a group

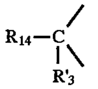

in which $R_{14}$ is as defined for (I) and $R'_3$ is as defined above;

or with a tertiary amine of the formula

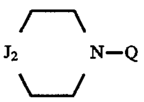

(XII)

in which $J_2$ and Q are as defined for (I);

or with a cyclic tertiary amine of the formula

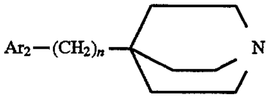

(XIII)

in which $Ar_2$ and n are as defined for (I);

or with a compound of the formula

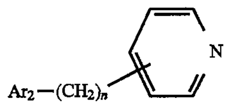

(XIV)

in which $Ar_2$ and n are as defined for (I); and 5) either, in the case where a cyclic secondary amine of formula (XI) is used, and after deprotection of the hydroxyl group or the amino group represented by $R'_3$, if appropriate, or optional conversion of $R'_2$ to $R_2$ or $R'_3$ to $R_3$, optionally converting the resulting product to a salt thereof;

or, in the case where a tertiary amine of formula (XII), a cyclic tertiary amine of formula (XIII) or a compound of formula (XIV) is used, isolating the resulting product in the form of a sulfonate and, if appropriate, a sulfonic acid salt, or optionally exchanging the resulting anion and, if appropriate, acid salt with another pharmaceutically acceptable anion and, if appropriate, another salt with a pharmaceutically acceptable mineral or organic acid.

In one variant of the method, if Am is a group $Am_1$,

1') a compound of formula (VIII) as defined above is oxidized to give a compound of the formula

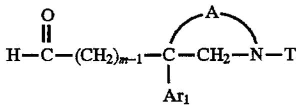

(XXXVIII)

in which m, $Ar_1$, A and T are as defined for a compound of formula (I);

2') the compound of formula (XXXVIII) is reacted with a compound of formula (XI) as defined above, in the presence of an acid, and the iminium salt formed as an intermediate is then reduced by means of a reducing agent; and 3') after deprotection of the hydroxyl groups or amino groups, if appropriate, or optional conversion of $R'_2$ to $R_2$ or $R'_3$ to $R_3$, the resulting product is optionally converted to a salt thereof.

The compounds of the formula

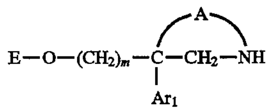

(II)

in enantiomerically pure form or in racemic form are novel and form part of the invention.

The compounds of the formula

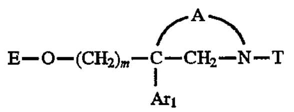

(VII)

in enantiomerically pure form or in racemic form are novel and form part of the invention.

The compounds of formulae (II) and (VII) in which E is hydrogen are particularly preferred.

The compounds of the formula

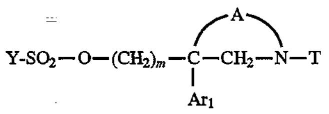

(X)

in enantiomerically pure form or in racemic form are novel and form part of the invention.

The compounds of the formula

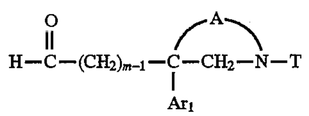

(XXXVIII)

in enantiomerically pure form or in racemic form are novel and form part of the invention.

In formulae (II), (VII), (X) and (XXXVIII), m and the groups E, A, $Ar_1$, T and Y are as defined above.

Thus, according to another of its features, the present invention relates to compounds of the formula

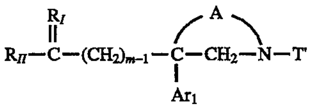

(XXXIX)

in which:

m, $Ar_1$ and A are as defined for a compound of formula (I);

$R_I$ is two hydrogen atoms and $R_{II}$ is:

either a group —O—E, in which E is a hydrogen atom or an O-protecting group, or a group —O—$SO_2$—Y, in which Y is a methyl, phenyl, tolyl or trifluoromethyl group;

or alternatively $R_I$ is an oxygen atom and $R_{II}$ is a hydrogen atom; and

T' is T as defined for a compound of formula (I); T' can also be hydrogen if $R_I$ is 2 hydrogen atoms and $R_{II}$ is simultaneously a group —O—E—, in enantiomerically pure form or in racemic form.

Thus, if E is an O-protecting group, this is selected from the conventional O-protecting groups well known to those skilled in the art, such as, for example, tetrahydropyran-2-yl, benzoyl or a ($C_1$–$C_4$)-alkylcarbonyl.

The O-protecting groups which may be used to obtain a compound of formula (I) in which $R_3$ is a hydroxyl are the conventional O-protecting groups well known to those skilled in the art, as defined above for E.

The N-protecting groups which may be used to obtain a compound of formula (I) in which $R_3$ is an amino are the conventional N-protecting groups well known to those skilled in the art, such as, for example, the trityl, methoxytrityl, tert-butoxycarbonyl or benzyloxycarbonyl group.

In particular, if the O-protecting group used is an acetyl group, the compound of formula (I) obtained represents the final product in which $R_3$ is an acetoxy, or if the N-protecting group used is a tertbutoxycarbonyl group, the compound of formula (I) obtained represents the final product in which $R_3$ is a tert-butoxycarbonylamino.

In step 1), the functional derivative of the acid (III) used is the acid itself or alternatively one of the functional derivatives which react with amines, for example an anhydride, a mixed anhydride, the acid chloride or an activated ester such as the paranitrophenyl ester.

If the acid of formula (III) itself is used, the reaction is carried out in the presence of a coupling agent used in peptide chemistry, such as 1,3-dicyclohexylcarbodiimide or benzotriazol-1-yloxytris(dimethylamino)phosphonium hexafluorophosphate, in the presence of a base such as triethylamine or N,N-diisopropylethylamine, in an inert solvent such as dichloromethane or N,N-dimethylformamide, at a temperature between 0° C. and room temperature.

If an acid chloride is used, the reaction is carried out in an inert solvent such as dichloromethane or benzene, in the presence of a base such as triethylamine or N-methylmorpholine, and at a temperature between −60° C. and room temperature.

If a halogenated derivative of formula (IV), (V) or (VI) is used, the reaction is carried out in an inert solvent such as tetrahydrofuran, N,N-dimethylformamide or dimethyl sulfoxide, in the presence of a base such as potassium tert-butylate, sodium hydride or lithium diisopropylamide, and at a temperature between 0° C. and 80° C.

The resulting compound of formula (VII) is deprotected in step 2), if appropriate, by the methods known to those skilled in the art. For example, if E is a tetrahydropyran-2-yl group, the deprotection is effected by acid hydrolysis using hydrochloric acid in a solvent such as ether or methanol or a mixture of these solvents, or using pyridinium p-toluenesulfonate in a solvent such as methanol, or else using an Amberlyst® resin in a solvent such as methanol. The reaction is carried out at a temperature between room temperature and the reflux temperature of the solvent. If E is a benzoyl group or a $(C_1-C_4)$-alkylcarbonyl group, the deprotection is effected by hydrolysis in an alkaline medium using for example an alkali metal hydroxide such as sodium hydroxide, potassium hydroxide or lithium hydroxide, in an inert solvent such as water, methanol, ethanol or dioxane or a mixture of these solvents, at a temperature between 0° C. and the reflux temperature of the solvent.

In step 3), the reaction of the alcohol of formula (VIII) with a sulfonyl chloride of formula (IX) is carried out in the presence of a base such as triethylamine, pyridine, N,N-diisopropylethylamine or N-methylmorpholine, in an inert solvent such as dichloromethane, benzene or toluene, at a temperature between −20° C. and the reflux temperature of the solvent.

The resulting compound of formula (X) is reacted in step 4) with a compound of formula (XI), (XII), (XIII) or (XIV) by different procedures.

If a compound of formula (X) is reacted with a compound of formula (XI), the reaction is carried out in an inert solvent such as N,N-dimethylformamide, acetonitrile, methylene chloride, toluene or isopropanol, and in the presence or absence of a base. If a base is used, this is selected from organic bases such as triethylamine, N,N-diisopropylethylamine and N-methylmorpholine, or from alkali metal carbonates or bicarbonates such as potassium carbonate, sodium carbonate and sodium bicarbonate. In the absence of a base, the reaction is carried out using an excess of the compound of formula (XI) and in the presence of an alkali metal iodide such as potassium iodide or sodium iodide. If —A— in the compound of formula (X) is the divalent radical —O—CO— or $—CH_2—O—CO—$, the reaction is carried out at a temperature between room temperature and 80° C. If —A— in the compound of formula (X) is the divalent radical $—O—CH_2—CO—$, $—O—CH_2—CH_2—$, $—N(R_1)—CO—CO—$, $—N(R_1)—CH_2—CH_2—$, $—N(R_1)—CO—$ or $—O—CH_2—$, the reaction is carried out at a temperature between room temperature and 100° C.

If a compound of formula (X) is reacted with a compound of formula (XII) or (XIII), the reaction is carried out in a polar aprotic solvent such as acetonitrile, N,N-dimethylformamide or N,N-dimethylphenylacetamide, in an ether such as tetrahydrofuran, dioxane or methyl tert-butyl ether, or in a ketone such as methyl ethyl ketone. If —A— in the compound of formula (X) is the divalent radical —O—CO— or $—CH_2—O—CO—$, the reaction is carried out at a temperature between room temperature and 60° C. If —A— in the compound of formula (X) is the divalent radical $—O—CH_2—CO—$, $—O—CH_2—CH_2—$, $—N(R_1)—CO—CO—$, $—N(R_1)—CH_2—CH_2—$, $—N(R_1)—CO—$ or $—O—CH_2—$, the reaction is carried out at a temperature between room temperature and 100° C.

If a compound of formula (X) is reacted with a compound of formula (XIV), the reaction is carried out in a polar aprotic solvent such as acetonitrile, N,N-dimethylformamide or N,N-dimethylphenylacetamide, in an ether such as tetrahydrofuran, dioxane or methyl tertbutyl ether, or in a ketone such as methyl ethyl ketone. The reaction is carried out at a temperature between room temperature and 100° C.

In step 1') of the variant of the method, an alcohol of formula (VIII) is oxidized to an aldehyde of formula (XXXVIII). The oxidation reaction is carried out using for example oxalyl chloride, dimethyl sulfoxide and triethylamine in a solvent such as dichloromethane and at a temperature between −78° C. and room temperature.

Then, in step 2'), the compound of formula (XI) is reacted with an aldehyde of formula (XXXVIII) in the presence of an acid such as acetic acid, in an alcoholic solvent such as methanol, to form in situ an intermediate imine, which is reduced chemically using for example sodium cyanoborohydride, or catalytically using hydrogen and a catalyst such as palladium-on-charcoal or Raney® nickel.

The compounds of formula (I) according to the invention are finally obtained after deprotection of the hydroxyl groups or amino groups, if appropriate, or optional conversion of $R'_2$ to $R_2$ and $R'_3$ to $R_3$.

The resulting products of formula (I) are:

either isolated in the form of the free base or a salt, by the conventional techniques, if Am is $Am_1$, or, if Am is $Am_2$, $Am_3$ or $Am_4$, isolated in the form of sulfonate anion ($YSO_3^{\ominus}$) or alternatively the sulfonate anion of the resulting quaternary salt is optionally exchanged with another pharmaceutically acceptable anion.

If the compound of formula (I) in which Am is $Am_1$ is obtained in the form of the free base, salification is effected by treatment with the chosen acid in an organic solvent. Treatment of the free base, dissolved for example in an ether such as diethyl ether, in an alcohol such as propan-2-ol, in acetone or in dichloromethane, with a solution of the chosen acid in the same solvent gives the corresponding salt, which is isolated by the conventional techniques.

The hydrochloride, hydrobromide, sulfate, hydrogensulfate, dihydrogenphosphate, methanesulfonate, oxalate, maleate, fumarate, naphthalene-2-sulfonate and benzenesulfonate, for example, are prepared in this way.

When the reaction is complete, the compounds of formula (I) in which Am is $Am_1$ can be isolated in the form of a salt thereof, for example the hydrochloride or the oxalate; in this case, if necessary, the free base can be prepared by the neutralization of said salt with a mineral or organic base such as sodium hydroxide or triethylamine, or with an alkali metal carbonate or bicarbonate such as sodium or potassium carbonate or bicarbonate.

The sulfonate anion $YSO_3^{\ominus}$ originating from the reaction between the compound of formula (XII), (XIII) or (XIV) and the compound of formula (X) can be exchanged, in situ or after isolation of the compound of formula (I) in which Am is a group $Am_2$, $Am_3$ or $Am_4$ in which $X^{\ominus}$ is the ion $YSO_3^{\ominus}$, with another anion X® by the conventional methods, for example by exchange in solution with saturated sodium chloride solution or with hydrochloric acid solution if $X^{\ominus}$ is a chloride anion, or by exchange of the anion via elution of the compound (I) on an ion exchange resin, for example Amberlite IRA68® or Duolite A375®.

When the reaction is complete, the compounds of formula (I) in which Am is $Am_2$ are obtained in the form of a mixture of the axial and equatorial isomers. The isomers are separated by the usual methods, for example by chromatography or recrystallization.

The compounds of formula (II) are prepared by different procedures.

The compounds of formula (II) in which —A— is the divalent radical $—CH_2—O—CO—$ and E is hydrogen or an O-protecting group are prepared according to SCHEME 1 below, in which m and $Ar_1$ are as defined for a compound of formula (I) and Pr is an O-protecting group as defined above for E.

In step a1 of SCHEME 1, a compound of formula (XV) is reacted with a compound of formula (XVI) by the method described in patent applications EP-A-0428434 and EP-A-0474561.

The resulting compound (XVII) is reacted in step b1 with aqueous formaldehyde solution in the presence of a base such as 1,8-diazabicyclo[5.4.0]-undec-7-ene, in a solvent such as 1,2-dimethoxyethane and at a temperature between room temperature and the reflux temperature of the solvent.

The nitrile derivative of formula (XVIII) is reduced in step c1 to give the primary amine of formula (XIX). This reduction can be effected by means of hydrogen in the presence of a catalyst such as Raney® nickel, platinum oxide or palladium-on-charcoal, in an inert solvent such as an alcohol, for example ethanol, by itself or mixed with aqueous ammonia, or by means of a reducing agent such as lithium aluminum hydride, diisobutylaluminum hydride or borane in THF, in a solvent such as toluene, hexane, petroleum ether, xylene or tetrahydrofuran. The reaction is carried out at a temperature between 0° C. and 70° C.

In step d1, the compound (XIX) is reacted with a reactive derivative of carbonic acid, such as phosgene, in solution in

SCHEME 1

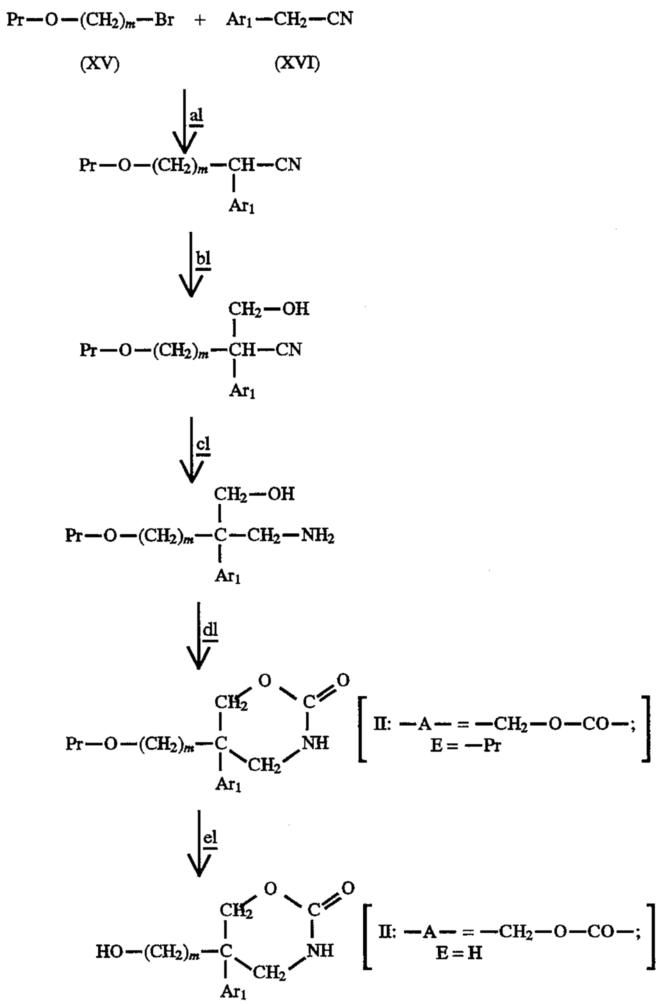

(XV) (XVI)

(XVII)

(XVIII)

(XIX)

toluene, or 1,1'-carbonyldiimidazole, in the presence of a base such as triethylamine, N,N-diisopropylethylamine or N-methylmorpholine, in a chlorinated solvent such as dichloromethane or 1,2-dichloroethane, or an ether such as tetrahydrofuran, and at a temperature between −70° C. and room temperature, to give a compound of the expected formula (II) in which E is an O-protecting group.

Using the methods described above, the O-protecting group is removed by hydrolysis (step e1) to give the compound of formula (II) in which E is hydrogen.

The compounds of formula (II) in which —A— is the divalent radical —O—$CH_2$—CO— and E is hydrogen or an O-protecting group are prepared according to SCHEME 2 below, in which m and $Ar_1$ are as defined for a compound of formula (I). $Pr_1$ and $Pr_2$ are the O-protecting group Pr as defined above for E; more particularly, $Pr_1$ is an O-protecting group hydrolyzable in an acid medium and $Pr_2$ is an O-protecting group hydrolyzable in a basic medium.

SCHEME 2

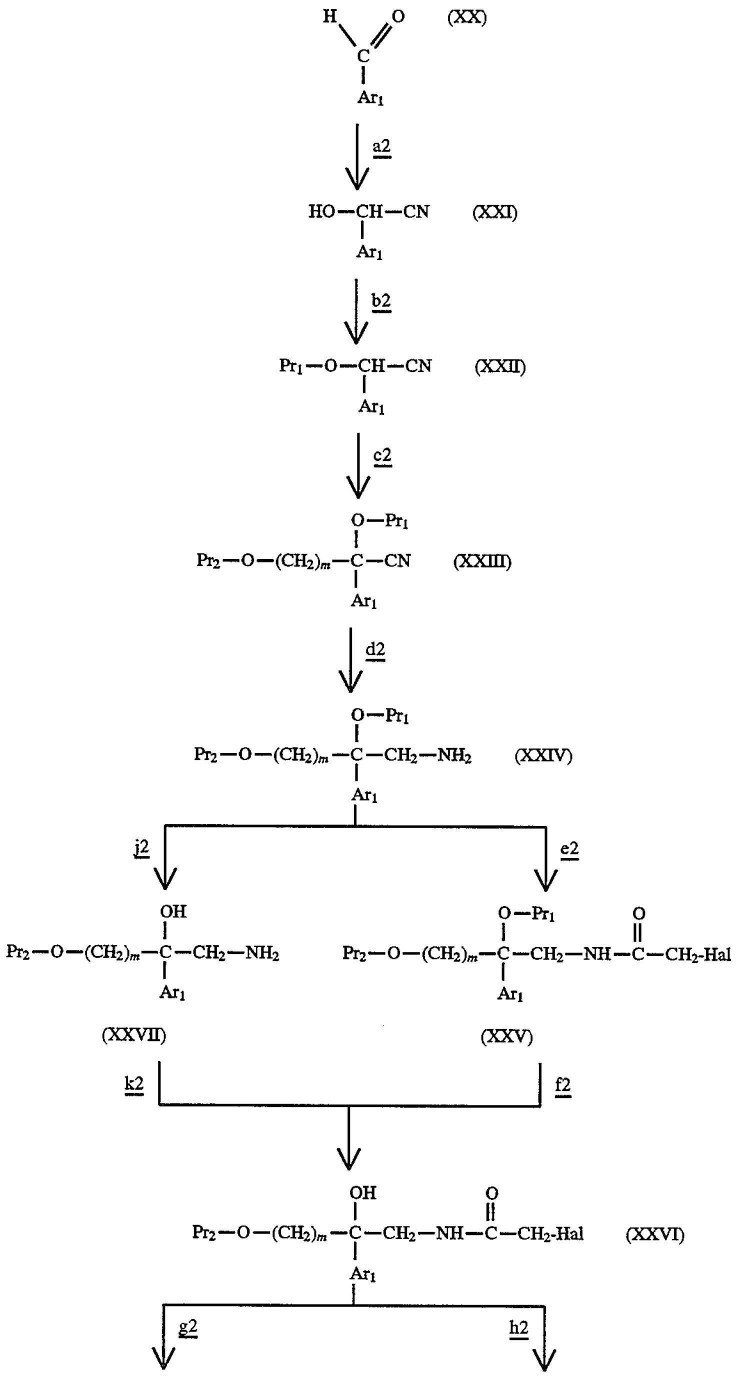

-continued

SCHEME 2

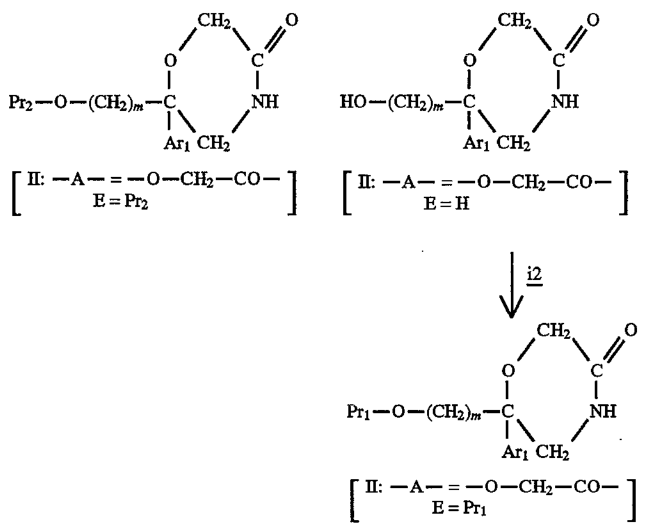

In step a2 of SCHEME 2, the synthesis of a cyanohydrin of formula (XXI) from an aldehyde of formula (XX) is effected by the methods well known to those skilled in the art, such as, for example, the one described in Organic Syntheses; Wiley, New York, 1932; Collect. vol. 1, p. 336, or by an adaptation of this method utilizing the action of sodium metabisulfite and potassium cyanide in aqueous solution.

In step b2, the hydroxyl group of the compound of formula (XXI) is protected by the methods known to those skilled in the art.

The resulting compound of formula (XXII) is treated in step c2 with a strong base such as lithium diisopropylamide, potassium tert-butylate or sodium hydride, to give a carbanion, which is reacted with a compound of the formula Hal—$(CH_2)_m$—O—$Pr_2$, in which Hal is a halogen, preferably bromine or chlorine, to give the compound of formula (XXIII). The reaction is carried out in an inert solvent such as an ether (for example tetrahydrofuran, diethyl ether or 1,2-dimethoxyethane), an amide (for example N,N-dimethylformamide) or an aromatic hydrocarbon (for example toluene or xylene), at a temperature between −70° C. and +60° C.

The nitrile derivative of formula (XXIII) is reduced in step d2 by the methods described above to give the primary amine of formula (XXIV).

In step e2, the compound of formula (XXIV) is reacted with a compound of the formula Hal—CO—$CH_2$—Hal, in which Hal is a halogen, preferably chlorine or bromine, in the presence of a base such as a tertiary amine (for example triethylamine, N-methylmorpholine or pyridine), to give a compound of formula (XXV). The reaction is carried out in an inert solvent such as a chlorinated solvent (for example dichloromethane, dichloroethane or chloroform), an ether (for example tetrahydrofuran or dioxane) or an amide (for example N,N-dimethylformamide), at a temperature between −70° C. and room temperature.

In step f2, the O-protecting group $Pr_1$ is removed from the compound of formula (XXV) by acid hydrolysis using the methods described above.

Alternatively, the O-protecting group $Pr_1$ is removed from the compound of formula (XXIV) by acid hydrolysis in step j2, after which the resulting compound (XXVII) is reacted in step k2 with a compound of the formula Hal—CO—$CH_2$—Hal by the methods described above in step e2.

The resulting compound of formula (XXVI) is cyclized in the presence of a base to give the compound of the expected formula (II). If it is desired to obtain a compound of formula (II) in which E is a protecting group $Pr_2$, a base such as an alkali metal carbonate (for example potassium carbonate), an alkali metal hydride (for example sodium hydride) or potassium tert-butylate is used in an inert solvent such as an aromatic hydrocarbon (for example xylene or toluene), an amide (for example N,N-dimethylformamide) or an ether (for example tetrahydrofuran), at a temperature between −30° C. and the reflux temperature of the solvent (step g2). If it is desired to obtain a compound of formula (II) in which E is hydrogen, a base such as an alkali metal hydroxide (for example sodium hydroxide or potassium hydroxide) in concentrated aqueous solution is used in a solvent such as an alkanol (for example propan-2-ol) or an amide (for example N,N-dimethylformamide) or a mixture of these solvents, at a temperature between room temperature and the reflux temperature of the solvent (step h2).

If appropriate, a compound of formula (II) in which E is an O-protecting group $Pr_1$ is prepared in step i2 by the methods known to those skilled in the art.

The compounds of formula (II) in which —A— is the divalent radical —O—$CH_2$—$CH_2$— and E is hydrogen or an O-protecting group are prepared according to SCHEME 3 below, in which m and $Ar_1$ are as defined for a compound of formula (I) and $Pr_1$ and $Pr_2$ are as defined in SCHEME 2 above.

SCHEME 3

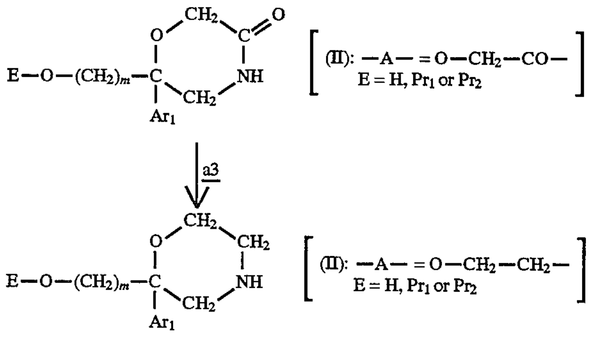

In step a3 of SCHEME 3, a compound of formula (II) in which —A— is the divalent radical —O—$CH_2$—CO— and E is hydrogen or an O-protecting group, obtained according to SCHEME 2, is reduced. The reduction is effected by means of a reducing agent such as lithium aluminum hydride, diisobutylaluminum hydride, sodium borohydride or borane in THF, in an inert solvent such as tetrahydrofuran, diethyl ether, 1,2-dimethoxyethane or toluene, at a temperature between room temperature and the reflux temperature of the solvent.

The compounds of formula (I) in which —A— is the divalent radical —O—CO— and E is hydrogen or an O-protecting group are prepared according to SCHEME 4 below, in which m and $Ar_1$ are as defined for a compound of formula (I) and $Pr_1$ and $Pr_2$ are as defined in SCHEME 2 above.

SCHEME 4

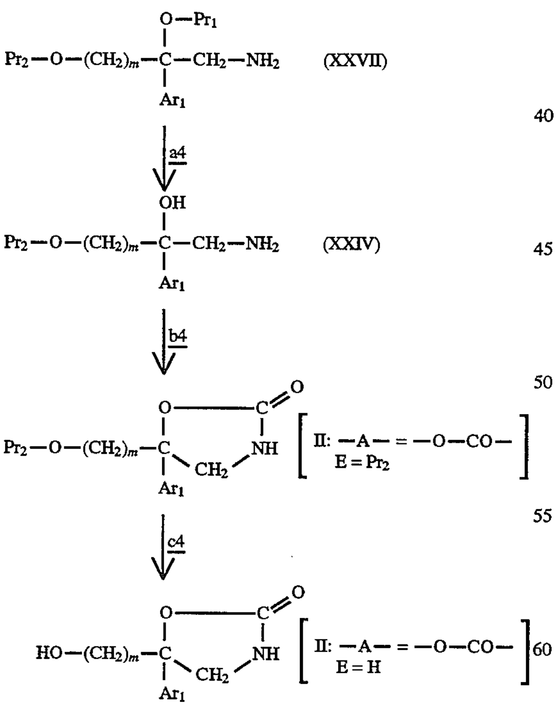

(XXVII)

(XXIV)

In step a4 of SCHEME 4, the O-protecting group $Pr_1$ of the compound of formula (XXIV), obtained in step d2 of SCHEME 2, is removed by acid hydrolysis using the methods described above.

The resulting compound of formula (XXVII) is reacted in step b4 with a reactive derivative of carbonic acid, such as 1,1'-carbonyldiimidazole, phosgene in toluene, or p-nitrophenyl chloroformate, in the presence of a base such as triethylamine, N,N-diisopropylethylamine or N-methylmorpholine, to give a compound of the expected formula (II) in which E is an O-protecting group. The reaction is carried out in an inert solvent such as a chlorinated solvent (for example 1,2-dichloroethane or dichloromethane), an ether such as tetrahydrofuran, an amide such as N,N-dimethylformamide or an aromatic solvent such as toluene, at a temperature between −60° C. and room temperature.

Using the methods described above, the O-protecting group $Pr_2$ is removed by basic hydrolysis (step c4) to give the compound of formula (II) in which E is hydrogen.

The compounds of formula (II) in which —A— is the divalent radical —N($R_1$)—CO—CO— and E is hydrogen or an O-protecting group are prepared according to SCHEME 5 below, in which m, $Ar_1$ and $R_1$ are as defined for a compound of formula (I) and $Pr_1$ is as defined above.

SCHEME 5

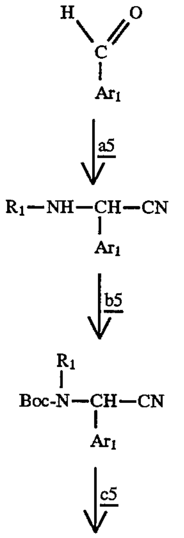

(XX)

(XXVIII)

(XXIX)

-continued

SCHEME 5

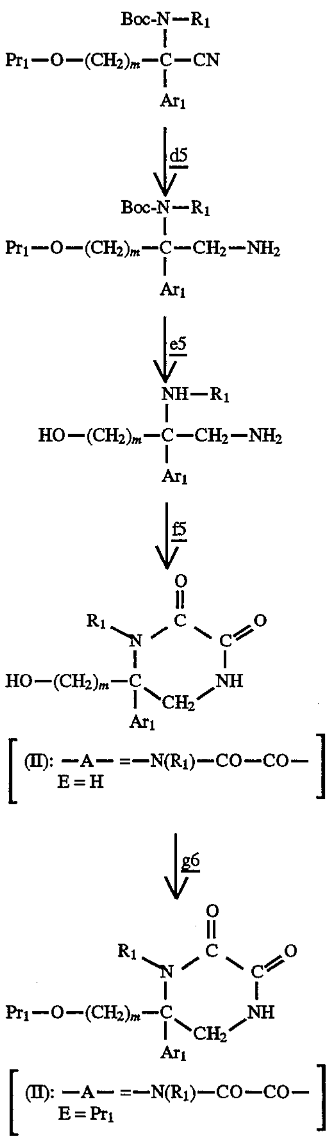

(XXX)

(XXXI)

(XXXII)

In step a5 of SCHEME 5, an α-amino nitrile compound of formula (XXVIII) is prepared from an aldehyde of formula (XX) by the method described in Tetrahedron Letters, 1984, 25 (41), 4583–4586, using an amine of the formula $H_2N—R_1$.

The amino group of the compound of formula (XXVIII) is protected in step b5 by an N-protecting group such as tert-butoxycarbonyl (Boc) or benzyloxycarbonyl, for example, using the methods known to those skilled in the art. The tert-butoxycarbonyl group is illustrated in SCHEME 5 above.

The resulting compound of formula (XXIX) is treated in step c5 with a strong base to form a carbanion, which is reacted with a compound of the formula Hal—$(CH_2)_m$—O—$Pr_1$ to give a compound of formula (XXX). The reaction is carried out by the method described in step c2 of SCHEME 2.

The nitrile derivative of formula (XXX) is reduced in step d5 by the methods described above to give the primary amine of formula (XXXI).

In step e5, the O-protecting group and the N-protecting group are removed from the compound of formula (XXXI) by acid hydrolysis with hydrochloric acid or trifluoroacetic acid, for example, in a solvent such as an alcohol (for example methanol), an ether (for example diethyl ether, dioxane or tetrahydrofuran) or a chlorinated solvent (for example dichloromethane), at a temperature between 0° C. and the reflux temperature of the reaction mixture.

In step f5, the compound of the expected formula (II) is prepared by application or adaptation of the method described by R. Granger, H. Orzalesi and Y. Robbe in Trav. Soc. Pharm. Montpellier, 1965, 25, Fasc. 4, 313–317, using the reaction of a compound of formula (XXXII) with diethyl oxalate in an alcoholic solvent such as ethanol, or an aromatic solvent such as toluene, or a mixture of these solvents, at a temperature between room temperature and the reflux temperature of the reaction mixture.

If appropriate, a compound of formula (II) in which E is an O-protecting group $Pr_1$ is prepared in step g5 by the methods known to those skilled in the art.

The compounds of formula (II) in which —A— is the divalent radical —$N(R_1)$—$CH_2$—$CH_2$— and E is hydrogen or an O-protecting group are prepared according to SCHEME 6 below, in which m, $R_1$ and $Ar_1$ are as defined for a compound of formula (I) and $Pr_1$ is an O-protecting group as defined above for E.

SCHEME 6

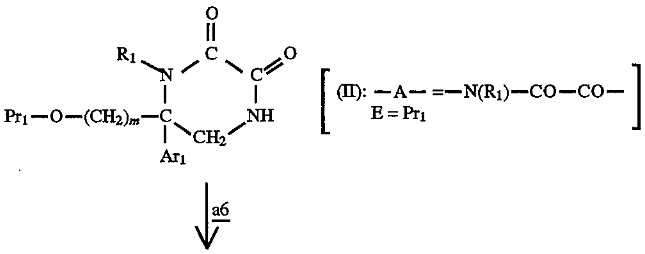

-continued

SCHEME 6

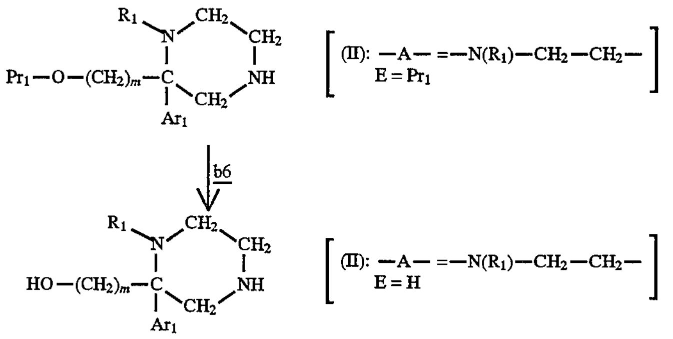

In step a6 of SCHEME 6, a compound of formula (II) in which —A— is the divalent radical —N($R_1$)—CO—CO— and E is an O-protecting group, obtained in step g5 of SCHEME 5, is reduced. The reduction is effected by means of a reducing agent such as lithium aluminum hydride, in an inert solvent such as an ether (for example tetrahydrofuran, 1,2-dimethoxyethane or diethyl ether) or an aromatic solvent such as toluene, at a temperature between room temperature and the reflux temperature of the solvent.

If appropriate, the O-protecting group is removed in step b6 by acid hydrolysis using the methods described above to give the compound of formula (II) in which E is hydrogen.

The compounds of formula (II) in which —A— is the divalent radical —N($R_1$)—CO— and E is hydrogen or an O-protecting group are prepared according to SCHEME 7 below, in which m, $R_1$ and $Ar_1$ are as defined for a compound of formula (I) and $Pr_1$ is as defined in SCHEME 2 above.

In step a7, the hydroxyl of the compound of formula (XXXII), obtained in step e5 of SCHEME 5, is protected by the methods known to those skilled in the art.

In step b7, the resulting compound of formula (XXXIII) is reacted with a reactive derivative of carbonic acid, such as 1,1'-carbonyldiimidazole, phosgene in toluene, or p-nitrophenyl chloroformate, in the presence of a base such as triethylamine, N,N-diisopropylethylamine or N-methylmorpholine, to give an expected compound of formula (II) in which E is an O-protecting group. The reaction is carried out in an inert solvent such as a chlorinated solvent (for example 1,2-dichloroethane or dichloromethane), an ether (for example tetrahydrofuran), an amide (for example N,N-dimethylformamide) or an aromatic solvent (for example toluene), at a temperature between −60° C. and 60° C.

SCHEME 7

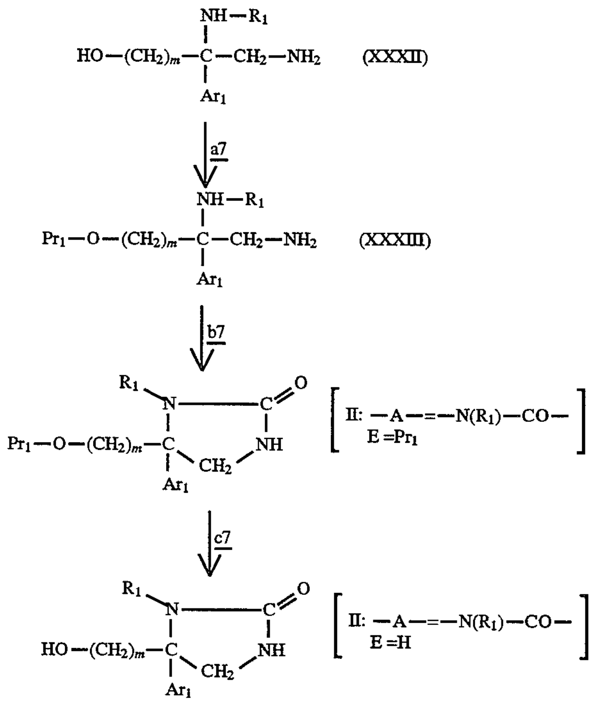

(XXXII)

(XXXIII)

If appropriate, a compound of formula (II) in which E is hydrogen is prepared in step c7 by the methods known to those skilled in the art.

The compounds of formula (II) in which —A— is the divalent radical —O—$CH_2$— and E is hydrogen or an O-protecting group are prepared according to SCHEME 8 below, in which m and $Ar_1$ are as defined for a compound of formula (I) and $Pr_2$ is as defined in SCHEME 2 above.

SCHEME 8

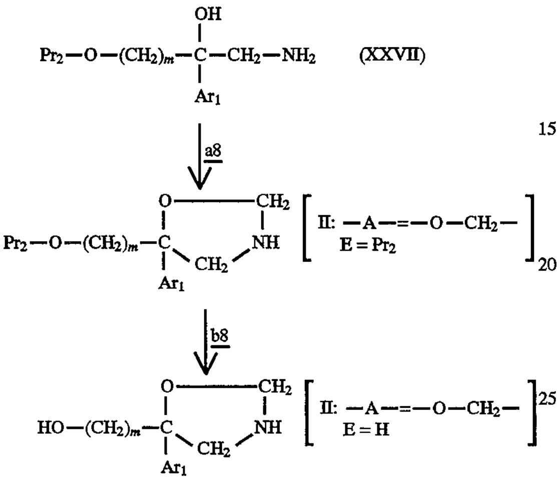

(XXVII)

In step a8 of SCHEME 8, a compound of formula (XXVII) is reacted with aqueous formaldehyde solution in an inert solvent such as tetrahydrofuran, at a temperature between room temperature and the reflux temperature of the solvent, to give a compound of the expected formula (II) in which E is an O-protecting group.

Using the methods described above, the O-protecting group $Pr_2$ is removed by basic hydrolysis (step b8) to give the compound of formula (II) in which E is hydrogen.

The compounds of formulae (XVIII), (XIX), (XXIII), (XXIV), (XXVII), (XXXI), (XXX), (XXXII) and (XXXIII) and the compounds of formula (XXXIV), defined below, are novel products which constitute the key intermediates for the preparation of the compounds of formula (I).

Thus the compounds of the formula

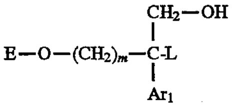

(XXXV)

in which:

m and $Ar_1$ are as defined for a compound of formula (I);

E is as defined for a compound of formula (II); and

L is a cyano group or an aminomethyl group, in enantiomerically pure form or in racemic form if L is an aminomethyl group, are novel and form part of the invention.

The compounds of the formula

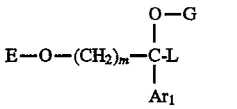

(XXXVI)

in which:

m, $Ar_1$, E and L are as defined above; and

G is a hydrogen or an O-protecting group, in enantiomerically pure form or in racemic form if L is an aminomethyl group, are novel and form part of the invention.

The compounds of the formula

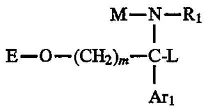

(XXXVII)

in which:

m, $Ar_1$, E and L are as defined above;

$R_1$ is as defined for a compound of formula (I); and

M is a hydrogen or an N-protecting group, in enantiomerically pure form or in racemic form if L is an aminomethyl group, are novel and form part of the invention.

The compounds of formulae (XXXV), (XXXVI) and (XXXVII) are obtained by the methods described above. More particularly, the deprotected compounds (E=G=M=H) are obtained after removal of the O-protecting or N-protecting groups by the methods known to those skilled in the art.

Thus, according to another of its features, the present invention relates to compounds of the formula

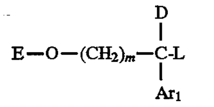

(XXXX)

in which:

m and $Ar_1$ are as defined for a compound of formula

E is a hydrogen or an O-protecting group;

L is a cyano group or an aminomethyl group;

D is a group selected from:

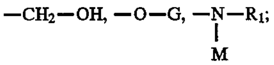

G is a hydrogen or an O-protecting group;

M is a hydrogen or an N-protecting group; and $R_1$ is as defined for a compound of formula (I), in enantiomerically pure form or in racemic form if L is an aminomethyl group.

The piperidines of formula (XI) are known or are prepared by known methods such as those described in EP-A-0428434, EP-A-0474561, EP-A-0512901 and EP-A-0515240.

The piperidines of formula (XI) can also be prepared by methods well known to those skilled in the art, such as those described in the following publications:

J. Heterocyclic Chem., 1986, 23, 73–75

J. Chem. Sec., 1950, 1469

J. Chem. Sec., 1945, 917

J. Pharmaceutical Sci., 1972, 61, 1316–1317

J. Org. Chem., 1957, 22, 1484–1489

Chem. Ber., 1975, 108, 3475–3482.

The compounds of formula (XI) are generally prepared in a form protected on the piperidine nitrogen; the actual compounds of formula (XI) are obtained after a deprotection step.

More particularly, to prepare for example a compound of formula (XI) in which $J'_1$ is a group

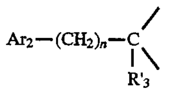

in which $Ar_2$ is a pyrid-2-yl radical n is zero and $R'_3$ is a hydroxyl, 2-bromopyridine is reacted with 1-benzylpiperid-4-one in the presence of a base such as butyllithium. The expected 4-hydroxy-4-(pyrid-2-yl)piperidine is obtained after removal of the N-protecting group.

To prepare a compound of formula (XI) in which $R'_3$ is a group $—NR_4R_5$ in which $R_4$ and $R_5$ are each hydrogen, a compound of formula (XI) in which $R'_3$ is an acetamido group is hydrolyzed in an acid medium.

A compound of formula (XI) in which $R'_3$ is a group $—NR_4R_5$ in which $R_4$ and $R_5$, together with the nitrogen atom to which they are bonded, form a heterocycle is prepared by the application or adaptation of Bruylants' reaction (Bull. Soc. Chim. Belges, 1924, 33, 467 and Tetrahedron Letters, 1988, 29 (52), 6827–6830).

To prepare a compound of formula (XI) in which $R'_3$ is a group $—CH_2—NR_{12}R_{13}$ in which $R_{12}$ and $R_{13}$ are each hydrogen, a compound of formula (XI) in which $R'_3$ is a cyano is reduced. This reduction is effected by the methods well known to those skilled in the art.

A compound of formula (XI) in which $R'_3$ is a group $—CH_2—CH_2—NR_{12}R_{13}$ in which $R_{12}$ and $R_{13}$ are each a hydrogen is prepared from a compound of formula (XI) in which $R'_3$ is a group $—CH_2—CH_2—OH$ by application or adaptation of the method described in J. Med. Chem., 1989, 32, 391–396.

A compound of formula (XI) in which $R'_3$ is a group $—NR_4R_5$ in which $R_4$ is a hydrogen and $R_5$ is a $(C_1–C_7)$-alkyl or, respectively, a $(C_3–C_7)$-cycloalkylmethyl or a benzyl can be prepared by reducing a compound of formula (XI) in which $R'_3$ is a group $—(CH_2)_q—NR_6COR_7$ in which q is zero, $R_6$ is hydrogen and $R_7$ is a hydrogen or a $(C_1–C_6)$-alkyl or, respectively, a $(C_3–C_7)$-cycloalkyl or a phenyl. The reaction is carried out by means of a reducing agent such as lithium aluminum hydride, in a solvent such as tetrahydrofuran, at the reflux temperature of the solvent.

By an identical reaction, the compounds of formula (XI) in which $R'_3$ is a group $—NR_4R_5$ in which $R_4$ is a $(C_1–C_7)$-alkyl and $R_5$ is a $(C_1–C_7)$-alkyl or, respectively, a $(C_3–C_7)$-cycloalkylmethyl or a benzyl can be prepared from a compound of formula (XI) in which $R'_3$ is a group $—(CH_2)_q—NR_6COR_7$ in which q is zero, $R_6$ is a $(C_1–C_7)$-alkyl and $R_7$ is a hydrogen or a $(C_1–C_6)$-alkyl or, respectively, a $(C_3–C_7)$-cycloalkyl or a phenyl.

Likewise, the compounds of formula (XI) in which $R'_3$ is a group $—CH_2—NR_{12}R_{13}$ or, respectively, $—CH_2CH_2NR_{12}R_{13}$ in which $R_{12}$ is a hydrogen or a $(C_1–C_7)$-alkyl and $R_{13}$ is a $(C_1–C_7)$-alkyl, a $(C_3–C_7)$-cycloalkylmethyl or a benzyl can be prepared from a compound of formula (XI) in which $R'_3$ is a group $—(CH_2)_q—NR_6COR_7$ in which q is respectively 1 or 2, $R_6$ is a hydrogen or a $(C_1–C_7)$-alkyl and $R_7$ is a hydrogen, a $(C_1–C_6)$-alkyl, a $(C_3–C_7)$-cycloalkyl or a phenyl.

A compound of formula (XI) in which $R'_3$ is a group $—(CH_2)_q—NR_6COR_7$ in which $R_6$ and $R_7$ together are a group $—(CH_2)_3—$ or $—(CH_2)_4—$ is prepared by application or adaptation of the method described in J. Med. Chem., 1985, 28, 46–50.

The compounds of formula (XI) in which $R'_3$ is a group $—(CH_2)_q—NR_6C(=W_1)R_7$ in which $W_1$ is an oxygen atom, q is 0, 1 or 2, $R_6$ is a hydrogen or a $(C_1–C_7)$-alkyl and $R_7$ is a hydrogen or, respectively, a $(C_1–C_7)$-alkyl, a phenyl, a benzyl, a pyridyl, an optionally substituted $(C_3–C_7)$-cycloalkyl, a furyl, a thienyl, a pyrrolyl or an imidazolyl are obtained by reacting formic acid in acetic anhydride or, respectively, the appropriate anhydride $(R_7CO)_2O$ or the appropriate acid chloride $R_7COCl$, in the presence of a base such as triethylamine, with a compound of formula (XI) in which $R'_3$ is a group $—NHR_6$, $—CH_2$13 $NHR_6$ or $—CH_2—CH_2—NHR_6$.

Likewise, it is obvious for those skilled in the art that the compounds of formula (XI) in which $R'_3$ is a group $—(CH_2)_q—NR_6—C(=W_1)R_7$ in which q, $R_6$ and $W_1$ are as defined above and $R_7$ is a vinyl group may be prepared by reaction with an acryloyl chloride.

Likewise, the compounds of formula (XI) in which $R'_3$ is a group $—(CH_2)_q—NR_6COOR_8$ are prepared by reaction of a compound of formula (XI) in which $R'_3$ is a group $—NHR_6$, $—CH_2—NHR_6$ or $—CH_2—CH_2—NHR_8$ in the presence of a base such as triethylamine, with a chloroformate of the formula $ClCOOR_8$.

The compounds of formula (XI) in which $R'_3$ is a group $—(CH_2)_q—NR_6SO_2R_9$ are prepared by reaction of a compound of formula (XI) in which $R'_3$ is a group $—NHR_6$, $—CH_2—NHR_6$ or $—CH_2—CH_2—NHR_6$ in the presence of a base such as triethylamine, with a sulfonyl chloride of the formula $ClSO_2R_9$.

The compounds of formula (XI) in which $R'_3$ is a group $—(CH_2)_q—NR_6C(=W_1)NR_{10}R_{11}$ in which $R_{10}$ is a hydrogen and $W_1$ is an oxygen atom are prepared by reaction of a compound of formula (XI) in which $R'_3$ is a group $—NHR_6$, $—CH_2—NHR_6$ or $—CH_2—CH_2—NHR_6$ in the presence of a base such as triethylamine, with an isocyanate of the formula $R_{11}N=C=O$, The compounds of formula (XI) in which $R'_3$ is a group $—(CH_2)_q—NR_6C(=W_1)NR_{10}R_{11}$ in which $R_{10}$ is a $(C_1–C_7)$-alkyl and $W_1$ is an oxygen atom are prepared by reaction of a compound of formula (XI) in which $R'_3$ is a group $—NHR_6$, $—CH_2—NHR_6$ or $—CH_2—CH_2—NHR_6$ in the presence of a base such as triethylamine, with a carbamoyl chloride of the formula $ClCONR_{10}R_{11}$.

A compound of formula (XI) in which $R'_3$ is a group $—(CH_2)_q—NR_6CONR_{10}R_{11}$ can also be obtained by reacting a compound $HNR_{10}R_{11}$ with a compound of formula (XI) in which $R'_3$ is a group $—(CH_2)_q—NR_6COOR_8$ in which $R_9$ is a phenyl.

A compound of formula (XI) in which $R'_3$ is a group $—(CH_2)_q—NR_6COOR_8$ in which q=0 and $R_6$ is hydrogen can also be prepared by reacting a compound $R_8OH$ with a compound of formula (XI) in which $R'_3$ is an isocyanato group, $—N=C=O$.

A compound of formula (XI) in which $R'_3$ is a group $—(CH_2)_q—NR_6CONR_{10}R_{11}$ in which q=0 and $R_6$ is hydrogen can also be prepared by reacting a compound $NHR_{10}R_{11}$ with a compound of formula (XI) in which $R'_3$ is an isocyanato group.

A compound of formula (XI) in which $R'_3$ is an isocanato group is prepared from a compound of formula (XI) in which $R'_3$ is a carboxyl by the method described in Organic Synthesis, 51, 48–52.

A compound of formula (XI) in which $R'_3$ is a group $—(CH_2)_q—NR_6C(=W_1)R_7$ in which $W_1$ is a sulfur atom is obtained from a corresponding compound of formula (XI) which is protected on the piperidine nitrogen and in which $W_1$ is an oxygen atom by reaction with phosphorus pentasulfide or Lawesson's reagent, 2,4-bis(4-methoxyphenyl)-1,3-dithia-2,4-diphosphetane-2,4-disulfide, followed by deprotection of the piperidine nitrogen.

A compound of formula (XI) in which $R'_3$ is a group $—(CH_2)_q—NR_6C(=W_1)NR_{10}R_{11}$ in which $W_1$ is a sulfur atom is prepared by reacting a compound of formula (XI) which is protected on the piperidine nitrogen and in which R'$_3$ is a group —$(CH_2)_q$—$NR_6CONR_{10}R_{11}$ with phosphorus pentasulfide or Lawesson's reagent.

A compound of formula (XI) in which R'$_3$ is a group —$(CH_2)_q$—OH in which q is respectively one or two is prepared by reducing a compound of formula (XI) in which R'$_3$ is respectively a methoxycarbonyl or a methoxycarbonylmethyl by the method described in Chem. Ber., 1975, 108, 3475–3482.

The compounds of formula (XI) in which R'$_3$ is a group —$(CH_2)_q$—$OCOR_{17}$ are obtained by reacting an acid chloride $R_{17}COCl$ with the compounds of formula (XI) in which R'$_3$ is a group —$(CH_2)_q$—OH, in the presence of a base such as triethylamine; the compounds of formula (XI) in which R'$_3$ is a group HCOO—$(CH_2)_q$— are obtained by reaction with formic acid.

The compounds of formula (XI) in which R'$_3$ is a group ($C_1$–$C_7$)-alkyl-NHCOO—$(CH_2)_q$— are obtained by reacting a carbamoyl chloride ($C_1$–$C_7$)-alkyl-NHCOCl with the compounds of formula (XI) in which R'$_3$ is a group —$(CH_2)_q$—OH.

The same compounds are prepared by reacting an isocyanate ($C_1$–$C_7$)-alkyl-N=C=O with the compounds of formula (XI) in which R'$_3$ is a group —$(CH_2)_q$—OH.

A compound of formula (XI) in which R'$_3$ is a carboxyl can be prepared by hydrolyzing a compound of formula (XI) in which R'$_3$ is a cyano by the methods known to those skilled in the art.

A compound of formula (XI) in which R'$_3$ is a carboxymethyl can be prepared by the method described in Chem. Ber., 1975, 108, 3475–3482.

A compound of formula (XI) in which R'$_3$ is respectively a ($C_1$–$C_7$)-alkoxycarbonyl or a ($C_1$–$C_7$)-alkoxycarbonylmethyl can be prepared from a compound of formula (XI) in which R'$_3$ is respectively a carboxyl or a carboxymethyl by means of an esterification reaction using the methods well known to those skilled in the art.

To prepare a compound of formula (XI) in which J'$_1$ is a group

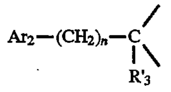

in which $Ar_2$ is an optionally substituted phenyl radical, n is one and R'$_3$ is a ($C_1$–$C_7$)-alkoxycarbonyl, a protected 4-($C_1$–$C_7$)-alkoxycarbonylpiperidine is reacted with an optionally substituted benzyl halide in the presence of a base such as sodium hydride, potassium tert-butylate or sodium diisopropylamide, in a solvent such as tetrahydrofuran, N,N-dimethylformamide or dimethyl sulfoxide, at a temperature between −78° C. an room temperature. The compound of the expected formula (XI) is obtained after a deprotection step.

To prepare a compound of formula (XI) in which R'$_3$ is respectively a group —$CONR_{10}R_{11}$ or a group —$CH_2CONR_{10}R_{11}$, a compound of formula (XI) in which R'$_3$ is respectively a carboxyl or a carboxymethyl is reacted with a compound of the formula $HNR_{10}R_{11}$ by the methods well known to those skilled in the art.

Using the methods cited above, a compound of formula (XI) in which R'$_3$ is a group —C(=$W_1$)$NR_{10}R_{11}$ or a group —$CH_2$—C(=$W_1$)$NR_{10}R_{11}$ in which $W_1$ is a sulfur atom is prepared from a compound of the corresponding formula (XI) in which $W_1$ is an oxygen atom.

To prepare a compound of formula (XI) in which R'$_3$ is a group

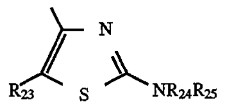

in which $R_{24}$ and $R_{25}$ are each independently a hydrogen or a ($C_1$–$C_7$)-alkyl, a compound of formula (XI) in which R'$_3$ is a group

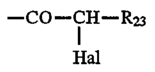

in which Hal is a halogen atom, preferably bromine, is reacted with a thiourea in which one of the amino groups is free or substituted by one or two ($C_1$–$C_7$)-alkyls.

A compound of formula (XI) in which R'$_3$ is a group

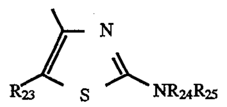

in which $R_{25}$ is is a formyl or, respectively, a ($C_1$–$C_7$)-alkylcarbonyl is prepared by reacting formic acid in acetic anhydride or, respectively, an acid chloride ($C_1$–$C_7$)-alkyl-COCl, in the presence of a base such as triethylamine, with the above compound of formula (XI) which is protected on the piperidine nitrogen and in which $R_{25}$ is hydrogen. The expected compound is obtained after a deprotection step.

The compound of formula (XI) in which R'$_3$ is a group

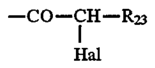

in which Hal is a bromine atom is obtained by brominating a compound of formula (XI) in which R'$_3$ is a group —CO—$CH_2$—$R_{23}$ by the conventional methods.

A compound of formula (XI) in which J'$_1$ is a group

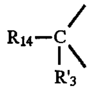

in which $R_{14}$ is a group —$CONR_{15}R_{16}$ and R'$_3$ is hydrogen can be prepared by reacting a protected 4-carboxypiperidine with a compound of the formula $HNR_{15}R_{16}$ by the methods well known to those skilled in the art. The compound of the expected formula (XI) is obtained after a deprotection step.

To prepare a compound of formula (XI) in which J'$_1$ is a group

in which $R_{14}$ is a group —$NR_{15}R_{16}$ and R'$_3$ is a cyano, a Strecker reaction is carried out by reacting a 1-benzylpiperid-4-one with a compound of the formula $HNR_{15}R_{16}$ in the presence of sodium cyanide. The compound of the expected formula (XI) is obtained after a deprotection step.

A compound of formula (XI) in which R'$_3$ is a group —O—$CH_2$—$CH_2$—$OR_{18}$ in which $R_{18}$ is hydrogen can be prepared by reacting a compound of formula (XI) in which R'$_3$ is a benzoyloxy with ethylene glycol in the presence of an acid such as sulfuric acid.

The compounds of formula (XI) in which R'$_3$ is a group —O—$CH_2$—$CH_2OR_{18}$ in which $R_{18}$ is a ($C_1$–$C_7$)-alkyl are prepared by means of an identical reaction using a 2-($C_1$–$C_7$)-alkoxyethanol.

The compounds of formula (XI) in which R'$_3$ is a group —O—$CH_2CH_2$—$OR_{18}$ in which $R_{18}$ is a formyl are prepared by reacting formic acid with a compound of formula (XI) in which R'$_3$ is a group —O—$CH_2CH_2$—OH. The compounds of formula (XI) in which R'$_3$ is a group —O—$CH_2CH_2$—$OR_{18}$ in which $R_{18}$ is a ($C_1$–$C_7$)-alkylcarbonyl are prepared by reaction with a $C_2$–$C_8$ acid chloride in the presence of a base such as triethylamine.

A compound of formula (XI) in which R'$_3$ is a group —$NR_6COCOR_{19}$ in which $R_{19}$ is a ($C_1$–$C_4$)-alkoxy is prepared by reacting a compound of the formula Cl—$COCOR_{19}$ with a compound of formula (XI) in which R'$_3$ is a group —$NHR_6$.

A compound of formula (XI) in which R'$_3$ is a group —CO—$NR_{21}R_{22}$ is prepared by reacting a compound $HNR_{20}$—$NR_{21}R_{22}$ with a compound of formula (XI) in which R'$_3$ is a chloroformyl A compound of formula (XI) in which R'$_3$ is a group

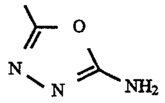

can be prepared by reacting a protected compound of formula (XI) in which R'$_3$ is a carbazoyl group (—CONH—$NH_2$) with cyanogen bromide by the method described in J. Org. Chem., 1961, 26, 88–95. The compound of formula (XI) in which R'$_3$ is a carbazoyl group is obtained by reacting hydrazine with a compound of formula (XI) in which R'$_3$ is a chloroformyl which is itself obtained by reacting thionyl chloride with a compound of formula (XI) in which R'$_3$ is a carboxyl.

The piperidines of formula (XII) are known or are prepared by known methods.

The quinuclidines of formula (XIII) are known or are prepared by known methods such as those described by T. Perrine, J. Org. Chem., 1957, 22, 1484–1489.

The pyridines of formula (XIV) are known or are prepared by known methods.

The enantiomers of the compounds according to the invention, of the formula

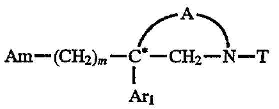
(I*)

in which:

"*" denotes that the carbon atom carrying this label has the determined (+) or (–) absolute configuration; and Am, m, $Ar_1$, A and T are as defined for the compounds of formula (I), and the salts thereof, where appropriate, with mineral or organic acids, are novel compounds which form part of the invention.

Resolution of the racemic mixtures of the compounds of formula (I) makes it possible to isolate the enantiomers of formula (I*).

It is preferable, however, to resolve the racemic mixtures from a compound of formula (II) or an intermediate which is useful for the preparation of a compound of formula (II).

Thus, if it is desired to prepare the enantiomers (I*) of the compounds of formula (I) in which —A— is the divalent radical —$CH_2$—O—CO—, the racemic mixture of an intermediate of the formula

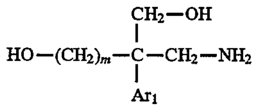
(XXXIV)

in which m and $Ar_1$ are as defined for a compound of formula (I), which is obtained by removal of the O-protecting group Pr from a compound of formula (XIX) by the methods described above, is resolved.

If it is desired to prepare the enantiomers (I*) of the compounds of formula (I) in which —A— is the divalent radical —O—CO—, —O—$CH_2$—CO—, —O—$CH_2$—$CH_2$—, or —O—$CH_2$—, the racemic mixture of an intermediate of the formula

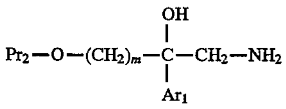
(XXVII)

in which m and $Ar_1$ are as defined for a compound of formula (I) and $Pr_2$ is as defined in SCHEME 2 above, is resolved.

If it is desired to prepare the enantiomers (I*) of the compounds of formula (I) in which —A— is the divalent radical —O—$CH_2$—$CH_2$—, it is also possible to resolve the racemic mixture of a compound of the formula

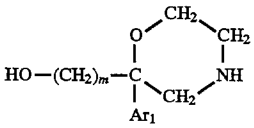

[(II) : —A— = —O—$CH_2$—$CH_2$— E = H]

in which m and $Ar_1$ are as defined for a compound of formula (I).

If it is desired to prepare the enantiomers (I*) of the compounds of formula (I) in which —A— is the divalent radical —N($R_1$)—CO—, —N($R_1$)—CO—CO— or —N($R_1$)—$CH_2$—$CH_2$—, the racemic mixture of an intermediate of the formula

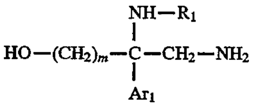
(XXXII)

in which m, $Ar_1$ and $R_1$ are as defined for a compound of formula (I), is resolved.

If resolution of the racemates is effected on the intermediates of formula (XXXIV), (XXVII), (XXXII) or (II) [—A—=—O—$CH_2$—$CH_2$— and E=H], this can be done by known methods involving the formation of a salt with optically active acids, for example with (+)- or (–)-tartaric acid. The diastereoisomers are then separated by conventional methods such as crystallization or chromatography, after which the optically pure enantiomers are obtained by hydrolysis.

The compounds of formula (I) above also include those in which one or more hydrogen, carbon or iodine atoms have been replaced with their radioactive isotope, for example tritium, carbon-14 or iodine-125. Such labeled compounds are useful in research, metabolic or pharmacokinetic studies and in biochemical tests as receptor ligands.

The affinity of the compounds for the tachykinin receptors was evaluated in vitro by several biochemical tests using radioligands:

1) The binding of $[^{125}I]$BH-SP (substance P labeled with iodine-125 using Bolton-Hunter's reagent) to the $NK_1$ receptors of human lymphoblasts.
2) The binding of $[^{125}I]$His-$NK_A$ to the $NK_2$ receptors of the rat duodenum or bladder.
3) The binding of $[^{125}I]$His[$MePhe^7$]$NK_B$ to the $NK_3$ receptors of the rat cerebral cortex, the guinea-pig cerebral cortex and the gerbil cerebral cortex, and to the human $NK_3$ cloned receptors expressed by CHO cells (Buell et al., FEBS Letters, 1992, 299, 90–95).

The tests were performed according to X. Emonds-Alt et al. (Eur. J. Pharmacol., 1993, 250, 403–413).

The compounds according to the invention have an affinity for the abovementioned tachykinin receptors, with an inhibition constant Ki below $10^{-8}$M.

In particular, the compounds of the present invention are active principles of pharmaceutical compositions, the toxicity of which is compatible with their use as drugs.

The compounds of the present invention are generally administered in dosage units. Said dosage units are preferably formulated as pharmaceutical compositions in which the active principle is mixed with a pharmaceutical excipient.

Thus, according to another of its features, the present invention relates to pharmaceutical compositions in which a compound of formula (I) or a pharmaceutically acceptable salt thereof is present as the active principle.

The compounds of formula (I) above and the pharmaceutically acceptable salts thereof can be used in daily doses of 0.01 to 100 mg per kilogram of body weight of the mammal to be treated, preferably in daily doses of 0.1 to 50 mg/kg. In humans, the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral, sublingual, inhalational, subcutaneous, intramuscular, intravenous, transdermal, local or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

When a solid composition in the form of tablets is prepared, the main active principle is mixed with a pharmaceutical vehicle such as silica, gelatin, starch, lactose, magnesium stearate, talc, gum arabic or the like. The tablets can be coated with sucrose, various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester, and incorporating the mixture obtained into soft or hard gelatin capsules.

A preparation in the form of a syrup or elixir can contain the active principle together with a sweetener, which is preferably calorie-free, methylparaben and propylparaben as an antiseptic, a flavoring and an appropriate color.

The water-dispersible granules or powders can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol or butylene glycol.

Administration by inhalation is effected using an aerosol which contains for example sorbitan trioleate or oleic acid, as well as trichlorofluoromethane, dichlorofluoromethane, dichlorotetrafluoroethane or any other biologically compatible propellant gas; it is also possible to use a system containing the active principle in powder form, by itself or associated with an excipient.

The active principle can also be formulated as microcapsules, with one or more carriers or additives if appropriate.

In each dosage unit, the active principle of formula (I) is present in the amounts appropriate to the daily doses envisaged- In general, each dosage unit is suitably adjusted according to the dosage and the intended type of administration, for example tablets, gelatin capsules and the like, sachets, ampoules, syrups and the like, and drops, so that such a dosage unit contains from 0.5 to 1000 mg of active principle, preferably from 2.5 to 250 mg, to be administered one to four times a day.

The abovementioned compositions can also contain other active products such as, for example, bronchodilators, antitussives, antihistamines, anti-inflammatories, antiemetics and chemotherapeutic agents.

According to another of its features, the present invention relates to the use of the products of formula (I) for the preparation of drugs intended for the treatment of physiological disorders associated with an excess of tachykinins, and all neurokinin-dependent pathological conditions of the respiratory, gastrointestinal, urinary, immune, cardiovascular and central nervous systems, as well as pain and migraine Non-limiting examples are:

acute and chronic pain associated for example with migraine, with pains experienced by cancer and angina patients, and with chronic inflammatory processes such as osteoarthritis and rheumatoid arthritis, inflammations such as neurogenic inflammations, chronic inflammatory diseases, for example obstructive chronic respiratory diseases, asthma, allergies, rhinitis, coughs, bronchitis, hypersensitivity, for example to pollen and mites, rheumatoid arthritis, fibrositis, osteoarthritis, psoriasis, ulcerative colitis, Crohn's disease, inflammation of the intestines (irritable colon), prostatitis, nervous bladder, incontinence, cystitis, urethritis and nephritis, ophthalmic diseases such as conjunctivitis and vitreoretinopathy, and skin diseases such as contact dermatitis, atopical dermatitis, urticaria, eczema, pruritus and burns, especially sunburn, diseases of the immune system associated with suppression or stimulation of the functions of the immune cells, for example rheumatoid arthritis, psoriasis, Crohn's disease, diabetes, lupus and rejection reactions following transplantation, small-cell lung cancers and demyelination diseases such as multiple sclerosis or amyotrophic lateral sclerosis, diseases of the central nervous system of the neuropsychiatric or neurological type, such as anxiety, vigilance disorders, mood disorders, depression, psychosis, schizophrenia, mania, dementia, epilepsy, Parkinson's disease, Alzheimer's disease, drug dependence, alcoholism, Down's syndrome and Huntington's chorea, as well as neurodegenerative diseases and stress-related somatic disorders, diseases of the gastrointestinal system, such as nausea, vomiting of any origin, irritable colon, gastric and duodenal ulcers, esophageal ulcer, diarrhea and hypersecretions, diseases of the cardiovascular system, such as hypertension, the vascular aspects of migraine, edema, thrombosis, angina pectoris, vascular spasms, circulatory diseases due to vasodilation, Reynauld's diseases, fibrosis and collagen diseases, and heart rate and rhythm disorders, in particular those caused by pain or stress.

The present invention also includes a method of treating said complaints at the doses indicated above.

The following abbreviations are used in the Preparations and in the Examples:

Me, OMe: methyl, methoxy
Et, OEt: ethyl, ethoxy
EtOH: ethanol
MeOH: methanol
Ether: diethyl ether
Iso ether: diisopropyl ether
DMF: dimethylformamide
DMSO: dimethyl sulfoxide
DCM: dichloromethane
THF: tetrahydrofuran
AcOEt: ethyl acetate
$Na_2CO_3$: sodium carbonate
$NaHCO_3$: sodium hydrogencarbonate
NaCl: sodium chloride
$Na_2SO_4$: sodium sulfate
$MgSO_4$: magnesium sulfate
NaOH: sodium hydroxide
HCl: hydrochloric acid
TFA: trifluoroacetic acid
KCN: potassium cyanide
$Na_2S_2O_5$: sodium metabisulfite
DBU: 1,8-diazabicyclo[5.4.0]undec-7-ene
$NH_4Cl$: ammonium chloride
M.p.: melting point
RT: room temperature
Silica H: silica gel 60H, marketed by Merck (DARMSTADT)
NMR: nuclear magnetic resonance δ: chemical shift
s: singlet
bs: broad singlet
d: doublet
t: triplet
q: quadruplet
mt: multiplet
u: unresolved signals

PREPARATIONS

Preparation 1.1

5-(3,4-Dichlorophenyl)-5-[2-(tetrahydropyran-2-yloxy)ethyl]tetrahydro-2H-1,3-oxazin-2-one A) 2-(3,4-Dichlorophenyl)-4-(tetrahydropyran-2-yloxy)butanenitrile A suspension of 17.75 g of sodium hydride (80% dispersion in oil) in 750 ml of THF is cooled in an ice bath, a solution of 100 g of 3,4-dichlorophenylacetonitrile in 250 ml of THF is added dropwise and the reaction mixture is stirred for two hours at RT. It is cooled to −20° C., a solution of 112.36 g of 1-bromo-2-(tetrahydropyran-2-yloxy)ethane in 120 ml of THF is added dropwise and the reaction mixture is stirred for 2 hours at RT. It is concentrated under vacuum, the residue is taken up with water and extracted with ether, the organic phase is washed twice with a buffer solution of pH 4, with a buffer solution of pH 7 and twice with saturated NaCl solution and dried over $Na_2SO_4$ and the solvent is evaporated off under vacuum. The residue is chromatographed on silica using toluene and then a toluene/AcOEt mixture (100/3; v/v) as the eluent to give 113.5 g of the expected product, which is used as such.

B) 2-(3,4-Dichlorophenyl)-2-(hydroxymethyl)-4-(tetrahydropyran-2-yloxy)butanenitrile A mixture of 12.56 g of the compound obtained in the previous step, 9.6 g of 37% aqueous formaldehyde solution and 0.3 g of DBU in 25 ml of 1,2-dimethoxyethane is refluxed for 1 hour. The reaction mixture is concentrated under vacuum, the residue is extracted with ether, the organic phase is washed twice with water, twice with a buffer solution of pH 4, twice with water and twice with saturated NaCl solution and dried over $Na_2SO_4$ and the solvent is evaporated off under vacuum to give 17 g of the expected product, which is used as such.

C) 2-(3,4-Dichlorophenyl)-2-hydroxymethyl)-4-(tetrahydropyran-2-yloxy)butylamine A mixture of 17 g of the compound obtained in the previous step and 6 g of Raney® nickel in 300 ml of EtoH and 40 ml of 20% aqueous ammonia solution is hydrogenated for 5 hours at 40° C. and at atmospheric pressure. The catalyst is filtered off and the filtrate is concentrated under vacuum. The residue is taken up with DCM, the organic phase is washed with water and with saturated NaCl solution and dried over $MgSO_4$ and the solvent is evaporated off under vacuum to give 16.5 g of the expected product in the form of an oil, which is used as such.

D) 5-(3,4-Dichlorophenyl)-5-[2-(tetrahydropyran-2-yl-oxy)ethyl]tetrahydro-2H-1,3oxazin-2-one 24.6 g of a 20% solution of phosgene in toluene, diluted in 150 ml of DMC, are cooled to 31 70° C., a solution of 16.5 g of triethylamine in 100 ml of DMC is added dropwise and the reaction mixture is stirred while the temperature is allowed to rise to RT. It is concentrated under vacuum, the residue is taken up with a water/AcOEt mixture and the product which crystallizes at the interphase is wrung to give a first crop of the expected product. After decantation of the filtrate, the organic phase is washed with water, with a buffer solution of pH 4 and with saturated NaCl solution and dried over $MgSO_4$ and the solvent is evaporated off under vacuum. The residue is taken up with AcOEt and the crystalline product formed is wrung to give the second crop of the product. A total of 4.5 g of the expected product is obtained.

Preparation 1.2

5-(3,4-Dichlorophenyl)-5-[3-(tetrahydropyran-2-yloxy)propyl]tetrahydro-2H-1,3-oxazin-2-one A) 2-(3,4-Dichlorophenyl)-5-(tetrahydropyran-2-yloxy)pentanenitrile A solution of 50.8 g of 3,4-dichlorophenylacetonitrile in 250 ml of THF is added dropwise at a temperature below 20° C. to a suspension of 12 g of sodium hydride (55% dispersion in oil) in 175 ml of THF and the reaction mixture is stirred for 2 hours at RT. It is cooled to −20° C., a solution of 62.5 g of 1-bromo-3-(tetrahydropyran-2-yloxy)propane in 60 ml of THF is added dropwise and the reaction mixture is stirred while the temperature is allowed to rise to RT. It is poured into a solution of 31 g of ammonium chloride in 1.4 liters of water and extracted with ether, the combined organic phases are washed with saturated NaCl solution and dried over $MgSO_4$ and the solvents are evaporated off under vacuum. The residue is chromatographed on silica using toluene and then a toluene/AcOEt mixture (95/5; v/v) as the eluent to give 64 g of the expected product, which is used as such.

B) 2-(3,4-Dichlorophenyl)-2-(hydroxymethyl)-5-(tetrahydropyran-2-yloxy)pentanenitrile A mixture of 15 g of the compound obtained in the previous step, 11.2 g of 37% aqueous formaldehyde solution and 0.35 g of DBU in 30 ml of 1,2-dimethoxyethane is refluxed for 1 hour. The reaction mixture is concentrated under vacuum, the residue is extracted with ether, the organic phase is washed with water, twice with a buffer solution of pH 4, twice with water and twice with saturated NaCl solution and dried over $Na_2SO_4$ and the solvent is evaporated off under vacuum. The residue is chromatographed on silica using toluene and then a toluene/AcOEt mixture (80/20; v/v) as the eluent to give 15.5 g of the expected product, which is used as such.

C) 2-(3,4-Dichlorophenyl)-2-(hydroxymethyl)-5-(tetrahydropyran-2-yloxy)pentylamine A mixture of 15.5 g of the compound obtained in the previous step and 5 g of Raney® nickel in 200 ml of EtOH and 40 ml of 20% aqueous ammonia solution is hydrogenated for 5 hours at 30° C. and at atmospheric pressure. The catalyst is filtered off and the filtrate is concentrated under vacuum. The residue is taken up with DMC, the organic phase is washed with water and with saturated NaCl solution and dried over $MgSO_4$ and the solvent is evaporated off under vacuum to give 14.9 g of the expected product in the form of an oil, which is used as such.

D) 5-(3,4-Dichlorophenyl)-5-[3-(tetrahydrppyran-2-yloxy)propyl]tetrahydro-2H-1,3-oxazine-2-one 21.4 g of a 20% solution of phosgene in toluene, diluted in 120 ml of DCM, are cooled to −70° C., a solution of 14.9 g of the compound obtained in the previous step and 4.98 g of triethylamine in 80 ml of DCM is added dropwise and the reaction mixture is stirred while the temperature is allowed to rise to RT. It is concentrated under vacuum, the residue is taken up with water and extracted with ether, the organic phase is washed with water and with saturated NaCl solution and dried over $MgSO_4$ and the solvent is evaporated off under vacuum to give 12.5 g of the expected product, which is used as such.

Preparation 1.3

6-(3,4-(Dichlorophenyl)-6-[2-(tetrahydropyran-2-yloxy)ethyl]morpholin-3-one

A) 2-(3,4-Dichlorophenyl)-2-hydroxyacetonitrile

A mixture of 70 g of 3,4-dichlorobenzaldehyde and 90 g of $Na_2S_2O_5$ in 300 ml of water is stirred overnight at RT. The reaction mixture is cooled to 0° C., a solution of 52 g of KCN in 100 ml of water is added dropwise and the reaction mixture is stirred while the temperature is allowed to rise to RT. It is extracted with ether, the organic phase is washed with water and dried over $Na_2SO_4$ and the solvent is evaporated off under vacuum to give 76 g of the expected product, which is used as such.

B) 2-(3,4-Dichlorophenyl)-2-(tetrahydropyran-2-yloxy)acetonitrile

A solution of 76 g of the compound obtained in the previous step and 0.25 g of p-toluenesulfonic acid monohydrate in 300 ml of DCM is cooled to 0° C., a solution of 39 g of 3,4-dihydro-2H-pyran in 50 ml of DCM is added dropwise and the reaction mixture is stirred while the temperature is allowed to rise to RT. It is washed with saturated $NaHCO_3$ solution and with water, the organic phase is dried over $Na_2SO_4$ and the solvent is evaporated off under vacuum to give 33 g of the expected product after crystallization at 0° C. from pentane. M.p.=61° C.

C) 4-(Benzoyloxy)-2-(3,4-dichlorophenyl)-2-(tetrahydropyran-2-yloxy)butanenitrile 56 ml of a 2M solution of lithium diisopropylamide in THF are cooled to −60° C., a solution of 32 g of the compound obtained in the previous step in 50 ml of THF is added dropwise and the mixture is stirred for 1 hour at −60° C. A solution of 25.4 g of 2-bromoethyl benzoate in 50 ml of THF is then added dropwise at −60° C. and the reaction mixture is stirred while the temperature is allowed to rise to RT. It is concentrated under vacuum, the residue is extracted with ether, the organic phase is washed with water and with a buffer solution of pH 4 and dried over $Na_2SO_4$ and the solvent is evaporated off under vacuum. The residue is chromatographed on silica using a toluene/AcOEt mixture (100/5; v/v) as the eluent to give 34 g of the expected product, which is used as such.

D) 4-(Benzoyloxy)-2-(3,4-dichlorophenyl)-2-(tetrahydropyran-2-yloxy)butylamine

A mixture of 34 g of the compound obtained in the previous step and 10 g of Raney® nickel in 400 ml of EtOH and 40 ml of concentrated ammonia solution is hydrogenated at RT and at atmospheric pressure. The catalyst is filtered off and the filtrate is concentrated under vacuum. The residue is taken up with water and extracted with ether, the organic phase is washed with saturated NaCl solution and dried over $Na_2SO_4$ and the solvent is evaporated off under vacuum. The residue is chromatographed on silica H using a gradient of a DCM/MeOH mixture (from 100/1; v/v to 100/3; v/v) as the eluent to give 16 g of the expected product, which is used as such.

E) N-(2-Bromoacetyl)-4-(benzoyloxy)-2-(3,4-dichlorophenyl)-2-hydroxybutylamine

A solution of 16 g of the compound obtained in the previous step and 4.8 g of triethylamine in 100 ml of DCM is cooled to −60° C., a solution of 5.68 g of bromoacetyl chloride in 20 ml of DCM is added dropwise and the reaction mixture is stirred for 30 minutes. It is concentrated under vacuum, the residue is extracted with ether, the organic phase is washed with water and with a buffer solution of pH 4 and dried over $Na_2SO_4$ and the solvent is evaporated off under vacuum. The product obtained is dissolved in the minimum amount of MeOH and acidified to pH 1 by the addition of a saturated solution of gaseous HCl in ether, and the solvents are evaporated off under vacuum. The residue is taken up with water and extracted with AcOEt, the organic phase is washed with saturated $NaHCO_3$ solution and with water and dried over $Na_{2SO_4}$ and the solvent is evaporated off under vacuum to give 16 g of the expected product, which is used as such.

F) 6-(3,4-Dichlorophenyl)-6-(2-hydroxyethyl)morpholin-3-one

A mixture of 16 g of the compound obtained in the previous step, 50 ml of propan-2-ol, 15 ml of 10N NaOH solution and 10 ml of DMF is stirred for 4 hours. The reaction mixture is concentrated under vacuum, the residue is extracted with AcOEt, the organic phase is washed with water and dried over $Na_2SO_4$ and the solvent is evaporated off under vacuum. The residue is chromatographed on silica H using a gradient of a DCM/MeOH mixture (from 100/3; v/v to 100/5; v/v) as the eluent to give 6.1 g of the expected product.

Proton NMR spectrum at 200 MHz in DMSO-$d_6$ δ: 2.05 ppm: mt: 2H 3.0 to 4.4 ppm: u: 6H 4.5 ppm: t: 1H 7.3 to 8.3 ppm: u: 4H G) 6-(3,4-Dichlorophenyl)-6-[2-(tetrahydropyran-2-yl-oxy) ethyl]morpholin-3-one A solution of 1.7 g of the compound obtained in the previous step and 0.003 g of p-toluenesulfonic acid monohydrate in 50 ml of DCM is cooled to 0° C., 0.588 g of 3,4-dihydro-2H-pyran in 10 ml of DCM is added dropwise and the reaction mixture is stirred for 1 hour at RT. It is concentrated under vacuum, the residue is extracted with ether, the organic phase is washed with saturated $NaHCO_3$ solution and with water and dried over $Na_2SO_4$ and the solvent is evaporated off under vacuum. The residue is chromatographed on silica H using a DCM/MeOH mixture (100/2; v/v) as the eluent to give 1.8 g of the expected product, which is used as such.

Preparation 1.4

6-[2-(Benzoyloxy)ethyl]-6-(3,4-dichlorophenyl) morpholin-3-one

A mixture of 4.8 g of the compound obtained in step E of Preparation 1.3 and 1.4 g of $K_2CO_3$ in 100 ml of xylene is heated at 130° C. overnight. After cooling to RT, the reaction mixture is filtered and the filtrate is concentrated under vacuum. The residue is extracted with ether, the organic phase is washed with a buffer solution of pH 2 and with water and dried over $MgSO_4$ and the solvent is evaporated off under vacuum. The residue is chromatographed on silica H using a DCM/MeOH mixture (100/1; v/v) as the eluent to give 1.4 g of the expected product.

Proton NMR spectrum at 200 MHz in DMSO-$d_6$

| | |
|---|---|
| δ: | 2.45 ppm : mt : 2H |
| | 3.75 ppm : AB system : 2H |
| | 3.9 to 4.5 ppm : u : 4H |
| | 7.4 to 7.9 ppm : u : 8H |
| | 8.25 ppm : bs : 1H |

This compound can also be obtained by following the three steps of the method described below.

A') 4-(Benzoyloxy)-2-(3,4-dichlorophenyl)-2-hydroxybutylamine hydrochloride

This compound is described in step A of Preparation 1.7.

B') N-(2-Chloroacetyl)-4-(benzoyloxy)-2-(3,4-dichlorophenyl)-2-hydroxybutylamine A solution of 20 g of the compound obtained in the previous step and 10.3 g of triethylamine in 100 ml of DCM is cooled to 0° C., 5.8 g of chloroacetyl chloride are added dropwise and the reaction mixture is stirred for 30 minutes. It is concentrated under vacuum, the residue is extracted with AcOEt, the organic phase is washed with water, with a buffer solution of pH 2 and with water and dried over $MgSO_4$ and the solvent is evaporated off under vacuum to give 22 g of the expected product, which is used as such.

C') 6-[2-(Benzoyloxy)ethyl]-6-(3,4-dichlorophenyl) morpholin-3-one

A solution of 22 g of the compound obtained in the previous step in 600 ml of THF is cooled to −10° C., 11.42 g of potassium tert-butylate are added and the reaction mixture is stirred until dissolution is complete. It is concentrated under vacuum, the residue is extracted with AcOEt, the organic phase is washed with a buffer solution of pH 2 and with water and dried over $MgSO_4$ and the solvent is evaporated off under vacuum to give 12.8 g of the expected product after crystallization from ether.

Preparation 1.5

2-(3,4-Dichlorophenyl)-2-(2-hydroxyethyl) morpholine

A suspension of 1.6 g of lithium aluminum hydride in 25 ml of THF is heated to 60° C., a solution of 4 g of the compound obtained in step F of Preparation 1.3 in 20 ml of THF is added dropwise and the mixture is stirred for 30 minutes under reflux. After cooling, 1.5 ml of water, 1.5 ml of 4N NaOH and then 4.5 ml of water are added. The mineral salts are filtered off on Célite®, the filtrate is decanted and the organic phase is evaporated under vacuum. The residue is taken up with ether and dried over $Na_2SO_4$ and the solvent is evaporated off under vacuum to give 3.6 g of the expected product.

Preparation 1.6

2-(3,4-Dichlorophenyl)-2-(3-hydroxypropyl) morpholine

A) 5-(Benzoyloxy)-2-(3,4-dichlorophenyl)-2-(tetrahydropyran-2-yloxy)pentanenitrile 47 ml of a 1.5M solution of lithium diisopropylamide in THF are cooled to −60° C., a solution of 19.3 g of the compound obtained in step B of Preparation 1.3 in 100 ml of THF is added dropwise and the mixture is stirred for 30 minutes at −60° C. 17 g of 3-bromopropyl benzoate are then added dropwise at −60° C. and the reaction mixture is stirred while the temperature is allowed to rise to RT. It is concentrated under vacuum, the residue is extracted with ether, the organic phase is washed with water and with saturated NaCl solution and dried over $Na_2SO_4$ and the solvent is evaporated off under vacuum to give 21 g of the expected product after crystallization from hexane.

B) 5-(Benzoyloxy)-2-(3,4-dichlorophenyl)-2-(tetrahydropyran-2-yloxy)pentylamine

A mixture of 20 g of the compound obtained in the previous step and 7 g of Raney® nickel in 300 ml of MeOH is hydrogenated at RT and at atmospheric pressure. The catalyst is filtered off and the filtrate is concentrated under vacuum. The residue is taken up with water and extracted with ether, the organic phase is washed with water and dried over $Na_2SO_4$ and the solvent is evaporated off under vacuum to give 20 g of the expected product, which is used as such.

C) N-(2-Chloroacetyl)-5-(benzoyloxy)-2-(3,4-dichlorophenyl)-2-(tetrahydropyran-2-yloxy)pentylamine A solution of 9 g of the compound obtained in the previous step and 2.4 g of triethylamine in 100 ml of DCM is cooled to 0° C., a solution of 2.23 g of chloroacetyl chloride in 20 ml of DCM is added dropwise and the reaction mixture is stirred for 30 minutes. It is concentrated under vacuum, the residue is extracted with ether, the organic phase is washed with water and dried over $Na_2SO_4$ and the solvent is evaporated off under vacuum to give 9.5 g of the expected product, which is used as such.

D) N-(2-Chloroacetyl)-5-(benzoyloxy)-2-(3,4-dichlorophenyl)-2-hydroxypentylamine A saturated solution of gaseous HCl in ether is added to a solution of 9 g of the compound obtained in the previous step in 50 ml of DCM and 50 ml of MeOH until the pH is 1, and the mixture is stirred for 30 minutes at RT. It is concentrated under vacuum, the residue is extracted with ether, the organic phase is washed with water and with saturated $NaHCO_3$ solution and dried over $Na_2SO_4$ and the solvent is evaporated off under vacuum. The residue is chromatographed on silica H using a DCM/MeOH mixture (100/3; v/v) as the eluent to give 4.7 g of the expected product, which is used as such.

E) 6-(3,4-Dichlorophenyl)-6-(3-hydroxypropyl)morpholin-3-one

A mixture of 2.95 g of the compound obtained in the previous step, 40 ml of propan-2-ol and 3 ml of 10N NaOH solution is stirred for 2 hours at RT. The reaction mixture is concentrated under vacuum, the residue is extracted with DCM, the organic phase is washed with water and dried over $Na_2SO_4$ and the solvent is evaporated off under vacuum. The residue is chromatographed on silica H using a gradient of a DCM/MeOH mixture (100/2; v/v to 100/5; v/v) as the eluent to give 0.5 g of the expected product. M.p.=130°–132° C.

F) 2-(3,4-Dichlorophenyl)-2-(3-hydroxypropyl)morpholine

A suspension of 0.82 g of lithium aluminum hydride in 10 ml of THF is heated to 60° C., a solution of 2 g of the compound obtained in the previous step in ml of THF is added dropwise and the mixture is stirred for 30 minutes under reflux. After cooling, 1 ml of water, 1 ml of 4N NaOH and then 3 ml of water are added. The mineral salts are filtered off on Célite®, the filtrate is decanted and the organic phase is evaporated under vacuum. The residue is taken up with ether and dried over $Na_2SO_4$ and the solvent is evaporated off under vacuum to give 2 g of the expected product.

| | |
|---|---|
| δ: | 0.8 to 2.2 ppm : u : 4H |
| | 2.5 to 3.7 ppm : u : 8H |
| | 4.3 ppm : t : 1H |
| | 7.2 to 7.7 ppm : u : 3H |

Preparation 1.7

5-[2-(Benzoyloxy)ethyl]-5-(3,4-dichlorophenyl)oxazolidin-2-one

A) 4-(Benzoyloxy)-2-(3,4-dichlorophenyl)-2-hydroxybutylamine hydrochloride

A saturated solution of gaseous HCl in ether is added at RT to a solution of 12 g of the compound obtained in step D of Preparation 1.3 in 50 ml of MeOH until the pH is 1, and the reaction mixture is stirred for 1 hour at RT. It is concentrated under vacuum, the residue is taken up with DCM and the precipitate formed is wrung and washed with ether to give 3.4 g of the expected product after recrystallization from propan-2-ol. M.p.=200°–204° C.

B) 5-[2-(Benzoyloxy)ethyl]-5-(3,4-dichlorophenyl)oxazolidin-2-one 1.4 g of 1,1'-carbonyldiimidazole are added at RT to a solution of 3 g of the compound obtained in the previous step and 0.85 g of triethylamine in 30 ml of 1,2-dichloroethane and the reaction mixture is stirred for 30 minutes at RT and then heated at 50° C. for 2 hours. It is concentrated under vacuum, the residue is taken up with water and extracted with DCM, the organic phase is washed with a buffer solution of pH 2 and with water and dried over $Na_2SO_4$ and the solvent is evaporated off under vacuum to give 3 g of the expected product.

Proton NMR spectrum at 200 MHz in DMSO-$d_6$

| | |
|---|---|
| δ: | 2.6 ppm : mt : 2H |
| | 3.75 ppm : AB system : 2H |
| | 4.35 ppm : mt : 2H |
| | 7.4 to 7.8 ppm : u : 8H |
| | 7.9 ppm : s : 1H |

Preparation 1.8

6-(3,4-Dichlorophenyl)-1-methyl-6-[2-(tetrahydropyran-2-yloxy)ethyl]piperazine-2,3-dione A) 2-(3,4-Dichlorophenyl)-2-(methylamino)acetonitrile hydrochloride A mixture of 10 g of 3,4-dichlorobenzaldehyde and 9.5 ml of cyanotrimethylsilane is cooled in an ice bath, 10 mg of zinc iodide are added and the mixture is stirred for 30 minutes at RT. 20 ml of a 33% solution of methylamine in EtOH are then added and the mixture is heated at 40° C. for 2 hours. The solvent is concentrated under vacuum, the residue is extracted with ether and the organic phase is dried over $MgSO_4$ and filtered. A saturated solution of gaseous HCl in ether is added to the filtrate until the pH is 1, and acetone is then added until the product precipitates. The precipitate formed is wrung, washed with ether and dried to give 12.8 g of the expected product. M.p.=172° C.

B) 2-(tert-Butoxycarbonyl-N-methylamino)-2-(3,4-dichlorophenyl)acetonitrile

Concentrated NaOH solution is added to an aqueous suspension of 12.8 g of the compound obtained in the previous step until the pH is 13, the mixture is extracted with ether, the organic phase is dried over $MgSO_4$ and the solvent is evaporated off under vacuum. The residue is taken up with 20 ml of 1,4-dioxane, 12.5 g of di-tert-butyl dicarbonate are added and the reaction mixture is heated at 60° C. for 2 hours. It is concentrated under vacuum, the residue is extracted with ether, the organic phase is washed with a buffer solution of pH 2, with saturated NaCl solution and with 10% $Na_2CO_3$ solution and dried over $MgSO_4$ and the solvent is evaporated off under vacuum. The residue is chromatographed on silica using heptane and then a heptane/AcOEt mixture (96/4; v/v) as the eluent to give 12.7 g of the expected product, which is used as such.

C) 2-(tert-Butoxycarbonyl-N-methylamino)-2-(3,4-dichlorophenyl)-4-(tetrahydropyran-2-yloxy)butanenitrile A solution of 11.1 g of the compound obtained in the previous step in 60 ml of DMF is added dropwise to a suspension of 1.5 g of sodium hydride (60% dispersion in oil) in 50 ml of DMF, the temperature being maintained at 25° C., and the mixture is stirred for 1 hour at RT. A solution of 8.1 g of 1-bromo-2-(tetrahydropyran-2-yloxy)ethane in 20 ml of DMF is then added and the reaction mixture is heated at 60° C. for 4 hours. After cooling to RT, it is poured into a mixture of ice and a buffer of pH 2 and extracted with ether, the organic phase is washed twice with water and dried over $MgSO_4$ and the solvent is evaporated off under vacuum. The residue is chromatographed on silica using heptane and then a heptane/AcOEt mixture (75/25; v/v) as the eluent to give 13.2 g of the expected product, which is used as such.

D) 2-(tert-Butoxycarbonyl-N-methylamino)-2-(3,4-dichlorophenyl)-4-(tetrahydropyran-2-yloxy)butylamine A mixture of 13.2 g of the compound obtained in the previous step and 4 g of Raney® nickel in 150 ml of EtOH and 50 ml of 20% aqueous ammonia solution is hydrogenated at 30° C. and at atmospheric pressure. After 5 hours, the catalyst is filtered off and the filtrate is concentrated under vacuum. The residue is extracted with ether, the organic phase is washed twice with water and dried over $MgSO_4$ and the solvent is evaporated off under vacuum to give 12.6 g of the expected product, which is used as such.

E) 2-(3,4-Dichlorophenyl)-4-hydroxy-2-(methylamino) butylamine hydrochloride

A mixture of 4.6 g of the compound obtained in the previous step and 10 ml of concentrated HCl solution in 40 ml of MeOH is heated at 70° C. for 1 hour. The solvent is then concentrated under vacuum, the residue is taken up with acetone and the precipitate formed is wrung, washed with ether and dried to give 2.79 g of the expected product. M.p.=240° C. (dec.).

F) 6-(3,4-Dichlorophenyl)-6-(2-hydroxyethyl)-1-methylpiperazine-2,3-dione

Concentrated NaOH solution is added to an aqueous suspension of 5.3 g of the compound obtained in the previous step until the pH is 13, the mixture is extracted with ether, the organic phase is dried over $MgSO_4$ and the solvent is evaporated off under vacuum. The product obtained (4 g) is taken up with 50 ml of EtOH, 2.57 g of diethyl oxalate are added and the reaction mixture is stirred for 1 hour at RT. It is concentrated under vacuum and the residue is taken up with 60 ml of toluene and refluxed for 70 hours. It is concentrated under vacuum to give 2.8 g of the expected product after crystallization from DCM. M.p.=260° C.

G) 6-(3,4-Dichlorophenyl)-1-methyl-6-[2-(tetrahydropyran-2-yloxy)ethyl]piperazine-2,3-dione 0.1 g of p-toluenesulfonic acid monohydrate and then 1.26 ml of 3,4-dihydro-2H-pyran are added to a suspension of 2.8 g of the compound obtained in the previous step in 50 ml of DCM and the reaction mixture is stirred overnight at RT. It is washed with 10% $Na_2CO_3$ solution and with water, the organic phase is dried over $MgSO_4$ and the solvent is evaporated off under vacuum. The residue is chromatographed on silica using AcOEt and then an AcOEt/MeOH mixture (93/7; v/v) as the eluent to give 3.1 g of the expected product which is used as such.

Preparation 1.9

2-(3,4-Dichlorophenyl)-1-methyl-2-[2-(tetrahydropyran-2-yloxy)ethyl]piperazine

A solution of 2 g of the compound obtained in Preparation 1.8 in 20 ml of THF is added dropwise to a suspension of 1.2 g of lithium aluminum hydride in 20 ml of THF and the mixture is refluxed for 1 hour. After cooling, 5 ml of water are added, the mineral salts are filtered off, the filtrate is concentrated under vacuum, the residue is taken up with ether, the organic phase is dried over $MgSO_4$ and the solvent evaporated off under vacuum to give 1.9 g of the expected product in the form of an oil.

Preparation 1.10

6-[2-(Benzoyloxy)ethyl]-6-(3,4-difluorophenyl) morpholin-3-one

A) 2-(3,4-Difluorophenyl)-2-hydroxyacetonitrile

A solution of 80.2 g of $Na_2S_2O_5$ in 250 ml of water is heated to 50° C., 50 g of 3,4-difluorobenzaldehyde are added and the reaction mixture is stirred for 1 hour at 50° C. and left to stand overnight at RT. It is cooled to 0° C., a solution of 77.7 g of KCN in 100 ml of water is added dropwise, the mixture is stirred while the temperature is allowed to rise to RT, and stirring is then continued for 1 hour at RT. The reaction mixture is extracted with ether, the organic phase is washed with water and dried over $MgSO_4$ and the solvent is evaporated off under vacuum to give 48 g of the expected product, which is used as such.

B) 2-(3,4-Difluorophenyl)-2-(tetrahydropyran-2-yloxy) acetonitrile

A solution of 48 g of the compound obtained in the previous step and 0.2 g of p-toluenesulfonic acid monohydrate in 500 ml of DCM is cooled to 0° C., a solution of 28.6 g of 3,4-dihydro-2H-pyran in 50 ml of DCM is added dropwise, the mixture is stirred while the temperature is allowed to rise to RT, and stirring is then continued overnight at RT. The reaction mixture is concentrated under vacuum, the residue is extracted with DCM, the organic phase is washed with 10% $Na_2CO_3$ solution and with water and dried over $Na_2SO_4$ and the solvent is evaporated off under vacuum. The residue is chromatographed on silica using a toluene/AcOEt mixture (100/15; v/v) as the eluent to give 43 g of the expected product, which is used as such.

C) 4-(Benzoyloxy)-2-(3,4-difluorophenyl)-2-(tetrahydropyran-2-yloxy)butanenitrile 133 ml of a 1.5M solution of lithium diisopropylamide in THF are cooled to −60° C., a solution of 43 g of the compound obtained in the previous step in 250 ml of THF is added dropwise and the mixture is stirred for 30 minutes at −60° C. A solution of 45.8 g of 2-bromoethyl benzoate in 100 ml of THF is then added dropwise at −60° C. and the reaction mixture is stirred while the temperature is allowed to rise to RT. It is concentrated under vacuum, the residue is extracted with ether, the organic phase is washed with water and with a buffer solution of pH 4 and dried over $Na_2SO_4$ and the solvent is evaporated off under vacuum. The residue is chromatographed on silica using a toluene/AcOEt mixture (100/5; v/v) as the eluent to give 47 g of the expected product, which is used as such.

D) 4-(Benzoyloxy)-2-(3,4-difluorophenyl)-2-(tetrahydropyran-2-yloxy)butylamine

A mixture of 47 g of the compound obtained in the previous step and 10 g of Raney® nickel in 400 ml of EtOH is hydrogenated at RT and at atmospheric pressure. The catalyst is filtered off and the filtrate is concentrated under vacuum. The residue is taken up with water and extracted with ether, the organic phase is washed with water and dried over $Na_2SO_4$ and the solvent is evaporated off under vacuum to give 45 g of the expected product, which is used as such.

E) 4-(Benzoyloxy)-2-(3,4-difluorophenyl)-2-hydroxybutylamine hydrochloride

A saturated solution of gaseous HCl in ether is added at RT to a solution of 45 g of the compound obtained in the previous step in 250 ml of MeOH until the pH is 1, and the reaction mixture is stirred for 30 minutes at RT. It is concentrated under vacuum, the residue is taken up with ether and the precipitate formed is wrung and washed with ether to give 15 g of the expected product after recrystallization from propan-2-ol. M.p.=202°–204° C.

F) N-(2-Chloroacetyl)-4-(benzoyloxy)-2-(3,4-difluorophenyl)-2-hydroxybutylamine

A solution of 12.2 g of the compound obtained in the previous step and 7.88 g of triethylamine in 100 ml of DCM is cooled to 0° C., a solution of 3.85 g of chloroacetyl chloride in 100 ml of DCM is added dropwise and the reaction mixture is stirred for 30 minutes. It is concentrated under vacuum, the residue is extracted with an ether/AcOEt mixture (50/50; v/v), the organic phase is washed with water, with a buffer solution of pH 4 and with water and dried over $Na_2SO_4$ and the solvent is evaporated off under vacuum to give 13.5 g of the expected product, which is used as such.

G) 6-[2-(Benzoyloxy)ethyl]-6-(3,4-difluorophenyl) morpholin-3-one

A mixture of 13.5 g of the compound obtained in the previous step and 20.7 g of $K_2CO_3$ in 100 ml of toluene is refluxed overnight. The reaction mixture is concentrated under vacuum, the residue is taken up with ether and the mixture is filtered. The filtrate is washed with water, with a buffer solution of pH 2 and with water and dried over $MgSO_4$ and the solvent is evaporated off under vacuum. The residue is chromatographed on silica H using a DCM/MeOH mixture (100/1; v/v) as the eluent to give 4.9 g of the expected product.

| | |
|---|---|
| δ: | 2.35 ppm : mt : 2H |
| | 3.65 ppm : AB system : 2H |
| | 3.8 to 4.35 ppm : u : 4H |
| | 7.1 to 7.8 ppm : u : 8H |
| | 8.2 ppm : bs : 1H |

Preparation 1.11

2-(3,4-Difluorophenyl)-2-(2-hydroxyethyl) morpholine

A suspension of 1.8 g of lithium aluminum hydride in 20 ml of THF is added dropwise at RT to a solution of 2.8 g of the compound obtained in Preparation 1.10 in 20 ml of THF and the mixture is then refluxed for 5 hours. After cooling, 2 ml of water, 2 ml of 4N NaOH and then 6 ml of water are added. The mineral salts are filtered off and the filtrate is concentrated under vacuum. The residue is dissolved in DCM, acidified to pH 1 by the addition of a saturated solution of gaseous HCl in ether, and extracted with water, the aqueous phase is washed with ether, rendered alkaline to pH 8 by the addition of concentrated NaOH solution, and extracted with DCM, the organic phase is washed with water and dried over $MgSO_4$ and the solvent is evaporated off under vacuum to give 0.77 g of the expected product, which is used as such in EXAMPLE 27, step A.

Preparation 1.12

5-[2-(Benzoyloxy)ethyl]-5-(3,4-difluorophenyl) oxazolidin-2-one 1 g of 1,1'-carbonyldiimidazole is added at RT to a solution of 2.1 g of the compound obtained in step E of Preparation 1.10 and 0.63 g of triethylamine in 50 ml of 1,2-dichloroethane and the reaction mixture is then stirred for 1 hour at RT and heated for 2 hours at 50° C. It is concentrated under vacuum, the residue is extracted with DCM, the organic phase is washed with water, with a buffer solution of pH 2 and with water and dried over $MgSO_4$ and the solvent is evaporated off under vacuum to give 1.5 g of the expected product.

Preparation 1.13

5-(3,4-Dichlorophenyl)-1-methyl-5-[2-(tetrahydropyran-2-yloxy)ethyl]imidazolidin-2-one A) 2-(3,4-Dichlorophenyl)-2-(methylamino)-4-(tetrahydropyran-2-yloxy)butylamine A mixture of 3.4 g of the compound obtained in step E of Preparation 1.8, 0.05 g of p-toluenesulfonic acid monohydrate and 2.1 ml of 3,4-dihydro-2H-pyran in 30 ml of DMF is heated at 60° C. for 45 minutes. The reaction mixture is poured onto ice, rendered alkaline by the addition of concentrated NaOH and extracted with ether, the organic phase is washed with water and dried over $MgSO_4$ and the solvent is evaporated off under vacuum to give 4.3 g of the expected product, which is used as such.

B) 5-(3,4-Dichlorophenyl)-1-methyl-5-[2-(tetrahydropyran-2-yloxy)ethyl]imidazolidin-2-one 1.6 g of 1,1'-carbonyldiimidazole are added to a solution of 3.2 g of the compound obtained in the previous step in 100 ml of 1,2-dichloroethane and the reaction mixture is stirred for 30 minutes at RT. It is then heated at 60° C. for 2 hours and concentrated under vacuum. The residue is extracted with AcOEt, the organic phase is washed with a buffer solution of pH 2, with saturated NaCl solution and with 10% $Na_2CO_3$ solution and dried over $MgSO_4$ and the solvent is evaporated off under vacuum. The residue is chromatographed on silica H using DCM and then a DCM/MeOH mixture (98/2; v/v) as the eluent to give 2.4 g of the expected product in the form of an oil.

Preparation 1.14

6-[3-(Benzoyloxy)propyl]-6-(3,4-dichlorophenyl) morpholin-3-one

A mixture of 7.5 g of the compound obtained in step D of Preparation 1.6, 9.3 g of $K_2CO_3$ and 3.75 g of sodium iodide in 100 ml of methyl ethyl ketone is refluxed overnight. After cooling, the reaction mixture is concentrated under vacuum, the residue is taken up with ether, the mineral salts are filtered off, the filtrate is washed with a buffer solution of pH 2 and with water, the organic phase is dried over $MgSO_4$ and the solvent is evaporated off under vacuum. The residue is chromatographed on silica H using DCM and then a gradient of a DCM/MeOH mixture (from 99/1; v/v to 98/2; v/v) as the eluent to give 1.3 g of the expected product.

Proton NMR spectrum at 200 MHz in DMSO-$d_6$

| | |
|---|---|
| δ: | 1.1 to 2.3 ppm : u : 4H |
| | 3.65 ppm : AB system : 2H |
| | 3.8 to 4.4 ppm : u : 4H |
| | 7.2 to 8.05 ppm : u : 8H |
| | 8.2 ppm : s : 1H |

Preparation 1.15

6-[2-(Benzoyloxy)ethyl]-6-(3,4-difluorophenyl) morpholin-3-one, (–) isomer

A) 4-(Benzoyloxy)-2-(3,4-difluorophenyl)-2-hydroxybutylamine, (+) isomer

A solution of 41 g of L-(+)-tartaric acid in 1200 ml of MeOH is heated to the reflux temperature, a solution of 81.4 g of the compound obtained in step E of Preparation 1.10, in the form of the free base, in 200 ml of MeOH is then added all at once and the mixture is left to crystallize for 48 hours while the temperature is allowed to return to RT. The crystals formed are wrung and washed with ether to give 42.5 g of the tartaric acid salt.

$[\alpha]_D^{20}$=+36.2° (c=1; DMF)

The resulting salt is recrystallized from 1450 ml of 70° EtOH to give 35 g of the tartaric acid salt after the crystals formed have been wrung and washed with ether.

$[\alpha]_D^{20}$+38.9° (c=1; DMF)

The resulting salt is taken up with 2000 ml of AcOEt, 40 ml of 10% $Na_2CO_3$ solution are added and then, after stirring and decantation, the organic phase is washed with water and dried over $MgSO_4$ and the solvent is evaporated off under vacuum to give 23.5 g of the expected product after crystallization from an iso ether/pentane mixture. M.p.=100.5°–100.6° C.

$[\alpha]_D^{20}$=+42.5° (c=1; MeOH)

B) N-(2-Chloroacetyl)-4-(benzoyloxy)-2-(3,4-difluorophenyl)-2-hydroxybutylamine, (+) isomer A solution of 23.5 g of the compound obtained in the previous step and 8.1 g of triethylamine in 300 ml of DCM is cooled to 0° C., a solution of 8.3 g of chloroacetyl chloride in 50 ml of DCM is added dropwise and the reaction mixture is stirred for 30 minutes at 0° C. It is concentrated under vacuum, the residue is extracted with an AcOEt/ether mixture (50/50; v/v), the organic phase is washed with a buffer solution of pH 2 and dried over $MgSO_4$ and the solvent is evaporated off under vacuum to give 24.8 g of the expected product after crystallization from an iso ether/pentane mixture.

$[\alpha]_D^{20}$=+26.1° (c=1; MeOH)

C) 6-[2-(Benzoyloxy)ethyl]-6-(3,4-difluorophenyl) morpholin-3-one, (−) isomer

A solution of 23.6 g of the compound obtained in the previous step in 750 ml of THF is cooled to 0° C., 13.7 g of potassium tert-butylate are added and the reaction mixture is stirred for 15 minutes. It is concentrated under vacuum, the residue is extracted with AcOEt, the organic phase is washed with a buffer solution of pH 2 and with water and dried over $MgSO_4$ and the solvent is evaporated off under vacuum. The residue is chromatographed on silica H using a DCM/MeOH mixture (from 100/1; v/v to 100/1.5; v/v) as the eluent to give 14.5 g of the expected product after crystallization from pentane.

$[\alpha]_D^{20}$=−7.1° (c=1; MeOH)

Preparation 1.16

6-[2-(Benzoyloxy)ethyl]-6-(3,4-difluorophenyl) morpholin-3-one, (+) isomer

A) 4-(Benzoyloxy)-2-(3,4-difluorophenyl)-2-hydroxybutylamine, (−) isomer

The wringing and wash liquors obtained from the crystallization and then recrystallization of the tartaric acid salt prepared in step A of Preparation 1.15 are concentrated under vacuum. The residue is treated with 10% $Na_2CO_3$ solution and extracted with AcOEt, the organic phase is dried over $MgSO_4$ and the solvent is evaporated off under vacuum to give 49 g of the amino alcohol in the form of a mixture of isomers. The amino alcohol is dissolved in 120 ml of MeOH and this solution is added all at once to a refluxing solution of 24.1 g of D-(−)-tartaric acid in 730 ml of MeOH. The mixture is left to crystallize for 48 hours while the temperature is allowed to return to RT. The crystals formed are wrung and washed with ether to give 40.7 g of the tartaric acid salt.

The resulting salt is recrystallized from 1445 ml of 70° EtOH to give 35 g of the tartaric acid salt after the crystals formed have been wrung and washed with ether. The resulting salt is taken up with 2000 ml of AcOEt, 10% $Na_2CO_3$ solution is added and then, after stirring and decantation, the organic phase is washed with water and dried over $MgSO_4$ and the solvent is evaporated off under vacuum to give 27 g of the expected product. M.p.=102° C.

$[\alpha]_D^{20}$=−40.5° (c=1; MeOH)

B) N-(2-Chloroacetyl)-4-(benzoyloxy)-2-(3,4-difluorophenyl)-2-hydroxybutylamine, (−) isomer A solution of 27 g of the compound obtained in the previous step and 13 ml of triethylamine in 500 ml of DCM is cooled to −30° C., 5.8 g of chloroacetyl chloride are added dropwise and the reaction mixture is stirred for 15 minutes. It is then washed with water, with 1N HCl solution and with 10% $Na_2CO_3$ solution, the organic phase is dried over $MgSO_4$ and the solvent is evaporated off under vacuum to give 28.6 g of the expected product after crystallization from an iso ether/pentane mixture. M.p.=63° C.

$[\alpha]_D^{20}$=−31.5° (c=1; MeOH)

C) 6-[2-(Benzoyloxy)ethyl]-6-(3,4-difluorophenyl) morpholin-3-one, (+) isomer

A solution of 28.5 g of the compound obtained in the previous step in 250 ml of THF is cooled to −30° C., 18.5 g of potassium tert-butylate are added all at once and the reaction mixture is stirred for 45 minutes. It is poured into 1000 ml of a buffer solution of pH 2 and extracted with ether, the organic phase is dried over $MgSO_4$ and the solvent is evaporated off under vacuum to give 20.5 g of the expected product after crystallization from an ether/iso ether mixture.

M.p.=92° C.

$[\alpha]_D^{20}$=+8.2° (c=1; MeOH)

Preparation 1.17

2-[2-(Benzoyloxy)ethyl]-2-(3,4-difluorophenyl) morpholine, (−) isomer

A solution of 12 g of the compound obtained in Preparation 1.15 ((−) isomer) in 75 ml of THF is added dropwise at RT to 100 ml of a 1M solution of borane in THF and the reaction mixture is stirred for 30 minutes at RT. It is then refluxed for 3 hours, 40 ml of a 1M solution of borane in THF are added and reflux is continued for 30 minutes. 80 ml of boiling MeOH are added and reflux is continued for 30 minutes. The reaction mixture is cooled in an ice bath, 30 ml of a saturated solution of gaseous HCl in ether are added and the reaction mixture is stirred overnight at RT. It is concentrated under vacuum, the residue is taken up with 10% $Na_2CO_3$ solution and extracted with ether, the organic phase is washed with water and with saturated NaCl solution and dried over $MgSO_4$ and the solvent is evaporated off under vacuum to give 11.2 g of the expected product in the form of an oil.

Preparation 1.18

2-[2-(Benzoyloxy)ethyl]-2-(3,4-difluorophenyl) morpholine, (+) isomer

A mixture of 19.9 g of the compound obtained in Preparation 1.16 ((+) isomer) and 300 ml of a 1M solution of borane in THF is heated at 60° C. for 2 hours. 60 ml of boiling MeOH are added and reflux is continued for 30 minutes. The reaction mixture is cooled to 10° C., 50 ml of a solution of gaseous HCl in ether are added and the reaction mixture is left to stand overnight at RT. It is concentrated under vacuum, the residue is taken up with 300 ml of 10% $Na_2CO_3$ solution, 300 ml of ether are added and the mixture is stirred for 30 minutes. After decantation, the organic phase is dried over $MgSO_4$ and the solvent is evaporated off under vacuum to give 20 g of the expected product in the form of an oil.

Preparation 1.19

2-[2-(Benzoyloxy)ethyl]-2-(3,4-dichlorophenyl) morpholine

A solution of 6 g of the compound obtained in Preparation 1.4 in 30 ml of THF is added dropwise at RT to 76 ml of a 1M solution of borane in THF and the mixture is then refluxed for 4 hours. 30 ml of MeOH are added dropwise and reflux is continued for 30 minutes. The reaction mixture is cooled to 0° C., 30 ml of a saturated solution of gaseous HCl in ether are added and the reaction mixture is stirred overnight at RT. It is concentrated under vacuum, the residue is taken up with 10% $Na_2CO_3$ solution and extracted with ether, the organic phase is washed with 10% $Na_2CO_3$ solution and with water and dried over $MgSO_4$ and the solvent is evaporated off under vacuum to give 5 g of the expected product.

Preparation 1.20

5-[2-(Benzoyloxy)ethyl]-5-(3,4-difluorophenyl) oxazolidin-2-one, (−) isomer

A mixture of 4 g of the compound obtained in step A of Preparation 1.16 ((−) isomer) and 2.2 g of 1,1'- carbonyldiimidazole in 40 ml of DCM is stirred for 30 minutes at RT and then refluxed for 1 hour. After cooling to RT, the reaction mixture is washed twice with 1N HCl solution, the organic phase is dried over $MgSO_4$ and the solvent is evaporated off under vacuum to give 4.18 g of the expected product after crystallization from iso ether. M.p.=147° C.

$[\alpha]_D^{20}$=−62.2° (c=1; DMF)

Preparation 1.21

2-[2-(Benzoyloxy)ethyl]-2-(3,4-difluorophenyl) morpholine 48 g of the compound obtained in Preparation 1.10 are added in portions at RT to 700 ml of a 1M solution of borane in THF and the mixture is then heated at 60° C. for 2 hours. 150 ml of MeOH are added dropwise and heating is continued for 30 minutes. The reaction mixture is cooled to 10° C., 120 ml of a saturated solution of hydrochloric acid in ether are added and the reaction mixture is left to stand overnight at RT. It is concentrated under vacuum, the residue is taken up with 600 ml of saturated $Na_2CO_3$ solution and 500 ml of ether and the mixture is stirred for 1 hour at RT. After decantation, the organic phase is washed with water and dried over $MgSO_4$ and the solvent is evaporated off under vacuum. The residue is taken up with 400 ml of propan-2-ol, 15 g of fumaric acid are added, the mixture is stirred for 30 minutes and the precipitate formed is wrung. It is taken up with 400 ml of 10% $Na_2CO_3$ solution and extracted with ether, the organic phase is dried over $MgSO_4$ and the solvent is evaporated off under vacuum to give 22 g of the expected product in the form of an oil.

Preparation 1.22

5-[2-(Benzoyloxy)ethyl]-5-(3,4-dichlorophenyl) oxazolidine 4 g of 37% aqueous formaldehyde solution are added to a solution of 9 g of the compound obtained in step A of Preparation 1.7 (in the form of the free base) in 100 ml of THF and the mixture is then refluxed for 30 minutes and stirred overnight at RT. It is concentrated under vacuum, the residue is extracted with ether, the organic phase is washed with water and dried over $Na_2SO_4$ and the solvent is evaporated off under vacuum to give 9 g of the expected product. Proton NMR spectrum at 200 MHz in DMSO-$d_6$ δ: 2.4 ppm: mt: 2H; 3.2 ppm: mt: 2H; 3.8 to 5.0 ppm: u: 4H; 7.0 to 8.0 ppm: u: 8H.

Preparation 1.23

5-[2-(Benzoyloxy)ethyl]-5-(3,4-difluorophenyl) oxazolidin-2-one, (+) isomer

This compound is prepared by the procedure described in Preparation 1.20 from the compound obtained in step A of Preparation 1.15 ((+) isomer).

$[\alpha]_D^{20}$=+61° (c=1; DMF)

Preparation 2.1

4-Phenyl-4-(pyrrolidin-1-ylcarbonyl)piperidine hemihydrate

A) 1-tert-Butoxycarbonyl-4-carboxy-4-phenylpiperidine 30 ml of water and 32.9 g of $K_2CO_3$ are added to a mixture of 30 g of 4-carboxy-4-phenylpiperidine p-toluenesulfonate and 300 ml of dioxane, the resulting mixture is then heated to 60° C. and 18.2g of di-tertbutyl dicarbonate are added dropwise. The reaction mixture is then heated at 60° C. for 2 hours and under reflux for 30 minutes. After cooling to RT, it is concentrated under vacuum, the residue is extracted with DCM, the organic phase is washed with a buffer solution of pH 2, acidified to pH 4 by the addition of 2N HCl, washed with a buffer solution of pH 2 , with water and with saturated NaCl solution and dried over $MgSO_4$ and the solvent is evaporated off under vacuum to give 23.7 g of the expected product.

B) 1-tert-Butoxycarbonyl-4-(pyrrolidin-1-ylcarbonyl)-4-phenylpiperidine 9.29 g of triethylamine and then 3.27 g of pyrrolidine are added to a solution of 14 g of the compound obtained in the previous step in 200 ml of DCM. The mixture is cooled in an ice bath, 22.4 g of BOP are added and the reaction mixture is stirred while the temperature is allowed to rise to RT. It is concentrated under vacuum, the residue is extracted with DCM, the organic phase is washed with water, three times with 10% NaOH solution, with water and three times with saturated NaCl solution and dried over $MgSO_4$ and the solvent is evaporated off under vacuum to give 16.4 g of the expected product.

C) 4-Phenyl-4-(pyrrolidin-1-ylcarbonyl)piperidine hemihydrate

Concentrated HCl solution is added to a solution of 16.4 g of the compound obtained in the previous step in 200 ml of MeOH until the pH is 1, and the reaction mixture is stirred for 5 hours at RT. It is concentrated under vacuum, the residue is taken up with acetone and the solvent is evaporated off under vacuum to give a white solid, which is recrystallized from propan-2-ol. The product obtained is taken up with 10% NaOH solution and extracted with DCM, the organic phase is washed with 10% NaOH solution and with saturated NaCl solution and dried over $MgSO_4$ and the solvent is evaporated off under vacuum to give 7 g of the expected product after crystallization from ether. M.p.=126° C.

Preparation 2.2

4-(N',N'-Dimethylureido)-4-phenylpiperidine p-toluenesulfonate hemihydrate

A) 4-Acetamido-1-benzyl-4-phenylpiperidine

This compound is prepared by reacting acetonitrile with 1-benzyl-4-hydroxy-4-phenylpiperidine by the method described in EP-A-474561.

B) 4-Amino-1-benzyl-4-phenylpiperidine dihydrochloride

A mixture of 30 g of the compound obtained in the previous step and 58 ml of concentrated HCl solution in 135 ml of water is refluxed for 48 hours. The reaction mixture is concentrated under vacuum, the residue is taken up with an EtOH/toluene mixture and the solvents are evaporated off under vacuum. The residue is dissolved in 50 ml of MeOH and crystallized by the addition of 250 ml of acetone to give 30.5 g of the expected product after wringing and drying.

C) 1-Benzyl-4-(N',N'-dimethylureido)-4-phenylpiperidine

A solution of 1.9 g of N,N-dimethylcarbamoyl chloride in 10 ml of 1,2-dichloroethane is added dropwise at RT to a solution of 6 g of the compound obtained in the previous step and 7.14 g of triethylamine in 50 ml of 1,2-dichloroethane and the mixture is refluxed for 8 hours. A few more drops of N,N-dimethylcarbamoyl chloride are added and reflux is continued for 3 hours. The reaction mixture is concentrated under vacuum, the residue is extracted with DCM, the organic phase is washed with water, with 10% NaOH solution, with water and with saturated NaCl solution and dried over $MgSO_4$ and the solvent is evaporated off under vacuum. The residue is chromatographed on silica using a gradient of a DCM/MeOH mixture (from 99/1; v/v to 96/4; v/v) as the eluent to give 1.8 g of the expected product.

D) 4-(N',N'-Dimethylureido)-4-phenylpiperidine p-toluenesulfonate hemihydrate

A mixture of 1.8 g of the compound obtained in the previous step, 1.11 g of p-toluenesulfonic acid monohydrate and 0.2 g of 10% palladium-on-charcoal in 150 ml of 95° EtOH is hydrogenated at 40° C. and at atmospheric pressure. The catalyst is filtered off on Célite® and the filtrate is evaporated under vacuum. The residue is taken up with acetone and the solvent is evaporated off under vacuum. The product obtained is dissolved in 25 ml of acetone, this solution is added slowly to 200 ml of ether and the crystalline product formed is wrung to give 1.86 g of the expected product.

M.p.=120°–122° C.

Preparation 2.3

4-(Acetyl-N-methylamino)-4-phenylpiperidine p-toluenesulfonate

A) 1-Benzyl-4-(formylamino)-4-phenylpiperidine 110 ml of acetic anhydride are added dropwise to a solution of 48.9 g of the compound obtained in step B of Preparation 2.2 and 25 g of sodium formate in 340 ml of formic acid and the reaction mixture is stirred overnight at RT. It is concentrated under vacuum, the residue is taken up with water, rendered alkaline by the addition of concentrated NaOH solution and extracted with DCM, the organic phase is dried over $MgSO_4$ and the solvent is evaporated off under vacuum to give 38.8 g of the expected product after crystallization from an iso ether/pentane mixture. M.p.=140° C.

B) 1-Benzyl-4-(methylamino)-4-phenylpiperidine

A solution of 38.8 g of the compound obtained in the previous step in 400 ml of THF is added slowly to a suspension of 12.5 g of lithium aluminum hydride in 100 ml of THF and the mixture is refluxed for 3 hours. After cooling, a solution of 5 ml of concentrated NaOH in 45 ml of water is added to the reaction mixture, the mineral salts are filtered off and the filtrate is concentrated under vacuum to give 38 g of the expected product.

C) 4-(Acetyl-N-methylamino)-1-benzyl-4-phenylpiperidine

A solution of 30 g of the compound obtained in the previous step and 16.5 ml of triethylamine in 300 ml of DCM is cooled to 0°–5° C., 8 ml of acetyl chloride are added dropwise and the reaction mixture is stirred for 30 minutes at RT. It is washed twice with water and with 2N NaOH solution, the organic phase is dried over $MgSO_4$ and the solvent is evaporated off under vacuum to give 31.6 g of the expected product after crystallization from an iso ether/pentane mixture.

M.p.=104° C.

D) 4-(Acetyl-N-methylamino)-4-phenylpiperidine p-toluenesulfonate

A mixture of 5 g of the compound obtained in the previous step, 2.9 g of p-toluenesulfonic acid monohydrate, 0.5 g of 10% palladium-on-charcoal and 80 ml of EtOH is hydrogenated for 3 hours at 25° C. and at atmospheric pressure. The catalyst is filtered off and the filtrate is concentrated under vacuum to give 5.7 g of the expected product after crystallization from acetone. M.p.=165° C.

Preparation 2.4

4-(Ethoxycarbonylamino)-4-phenylpiperidine trifluoroacetate

A) 1-tert-Butoxycarbonyl-4-isocyanato-4-phenylpiperidine

A solution of 25 g of the compound obtained in step A of Preparation 2.1 and 10.35 g of triethylamine in 100 ml of acetone is cooled to 0°–5° C., a solution of 8.7 g of methyl chloroformate in 30 ml of acetone is added dropwise at a temperature below 5° C. and the mixture is stirred for 30 minutes at 5° C. A solution of 10.66 g of sodium azide in 30 ml of water is then added dropwise at a temperature below 5° C. and the reaction mixture is stirred for 30 minutes at 5° C. It is poured into 500 ml of iced water and extracted four times with toluene and the organic phase is washed twice with a buffer solution of pH 2 and with saturated NaCl solution, dried over $MgSO_4$ and filtered. The filtrate is heated at 90° C. for 1 hour and the solvent is evaporated off under vacuum to give 18.9 g of the expected product in the form of an oil.

B) 1-tert-Butoxycarbonyl-4-(ethoxycarbonylamino)-4-phenylpiperidine

A solution of 6.28 g of the compound obtained in the previous step in 100 ml of EtOH is refluxed for 5 hours 30 minutes. Two drops of triethylamine are added and the mixture is then stirred overnight at RT and concentrated under vacuum to give 7.25 g of the expected product.

C) 4-(Ethoxycarbonylamino)-4-phenylpiperidine trifluoroacetate

A solution of 7.25 g of the compound obtained in the previous step in 20 ml of TFA is stirred for 30 minutes at RT and then concentrated under vacuum. The residue is taken up with acetone and the solvent is evaporated off under vacuum to give 6.02 g of the expected product after crystallization from an acetone/ether mixture. M.p.=173° C.

Preparation 2.5

4-Benzylquinuclidine

A) 1,4-Dibenzyl-4-cyanopiperidine

A solution of 15 g of 4-cyanopiperidine in 250 ml of THF is cooled to −50° C., 190 ml of a 1.5M solution of lithium diisopropylamide in cyclohexane are added dropwise and the mixture is stirred for 30 minutes at −50° C. 34 ml of benzyl bromide are then added and the mixture is stirred for 3 hours after the temperature has been allowed to rise to RT. The reaction mixture is poured into an ice/concentrated HCl mixture, ether is added and the precipitate formed is wrung and washed with water. The precipitate is taken up with water, rendered alkaline to pH 12 by the addition of concentrated NaOH solution and extracted with ether, the organic phase is dried over $MgSO_4$ and the solvent is evaporated off to give 31.7 g of the expected product after crystallization from pentane.

M.p.=92° C.

B) 4-Acetyl-1,4-dibenzylpiperidine hydrochloride 55 ml of a 1.6M solution of methyllithium in ether are added to a solution of 20 g of the compound obtained in the previous step in 400 ml of ether and the reaction mixture is stirred for 3 hours at RT. It is poured into iced water, the organic phase is decanted and then dried over $MgSO_4$ and the solvent is evaporated off under vacuum. The residue is taken up with 400 ml of water and 40 ml of concentrated HCl and refluxed for 2 hours. After one night at RT, the crystals formed are wrung, washed with acetone and then with ether and dried to give 17.6 g of the expected product. M.p.=246° C.

C) 1,4-Dibenzyl-4-(2-bromoacetyl)piperidine hydrobromide 1.6 ml of bromine are added to a solution of 10 g of the compound obtained in the previous step in 40 ml of acetic acid and the reaction mixture is stirred overnight at RT. 50 ml of ether are added and the crystals formed are wrung and washed with an acetone/ether mixture and then with ether to give 12.5 g of the expected product. M.p.=205° C.

D) 1,4-Dibenzyl-3-oxoquinuclidinium bromide

Concentrated NaOH solution is added to an aqueous suspension of 12.5 g of the compound obtained in the previous step until the pH is 12, the mixture is extracted with ether, the organic phase is dried over $MgSO_4$ and the solvent is evaporated off under vacuum. The residue is taken up with acetone and stirred for 2 hours at RT. The precipitate is wrung, washed with ether and dried to give 10.08 g of the expected product. M.p.=234° C.

E) 4-Benzyl-3-oxoquinuclidine

A mixture of 10 g of the compound obtained in the previous step and 1 g of 10% palladium-on-charcoal in 200 ml of MeOH is hydrogenated at RT and at atmospheric pressure. The catalyst is filtered off and the filtrate is evaporated under vacuum. The residue is taken up with ether and the precipitate formed is wrung. The precipitate is dissolved in water and rendered alkaline to pH 12 by the addition of concentrated NaOH solution and the precipitate formed is wrung, washed with water and dried to give 5 g of the expected product. M.p.=111° C.

F) 4-Benzylquinuclidine

A mixture of 5 of the compound obtained in the previous step, 2.5 g of hydrazine hydrate and 4.3 g of KOH in 25 ml of ethylene glycol is heated at 175° C. for 2 hours. The reaction mixture is poured into iced water and extracted twice with ether, the organic phase is washed with water and dried over $MgSO_4$ and the solvent is evaporated off under vacuum. The residue is dissolved in acetone and acidified to pH 1 by the addition of a saturated solution of hydrochloric acid in ether and the precipitate formed is wrung and washed with an acetone/ether mixture (50/50; v/v) and then with ether. The precipitate is dissolved in water, rendered alkaline to pH 12 by the addition of concentrated NaOH solution and extracted with ether, the extract is dried over $MgSO_4$ and the solvent is evaporated off under vacuum to give 1.8 g of the expected product. M.p.=48° C.

Preparation 2.6

4-Phenyl-4-(pyrrolidin-1-ylcarbonylamino) piperidine benzenesulfonate

A) 1-(Benzyloxycarbonyl)-4-carboxy-4-phenylpiperidine

A mixture of 37.7 g of 4-carboxy-4-phenylpiperidine p-toluenesulfonate, 53.3 g of 30% aqueous NaOH solution and 250 ml of water is cooled to 5° C. A solution of 18 g of benzyl chloroformate in 60 ml of acetone is added rapidly at 5° C. and the reaction mixture is stirred overnight while the temperature is allowed to rise to RT. It is washed twice with ether and, after decantation, the aqueous phase is acidified to pH 1 by the addition of concentrated HCl and then 2N HCl. The precipitate formed is wrung, dried, taken up with ether and wrung again to give 30.6 g of the expected product. M.p.=142°–144° C.

B) 1-(Benzyloxycarbonyl)-4-phenyl-4-(pyrrolidin-1-ylcarbonylamino)piperidine

A mixture of 33.9 g of the compound obtained in the previous step and 47.6 g of thionyl chloride in 200 ml of 1,2-dichloroethane is refluxed for 1 hour. The reaction mixture is concentrated under vacuum, the residue is taken up with acetone and the solvent is evaporated off under vacuum. The residue is dissolved in 200 ml of acetone and cooled to 5° C., a solution of 13 g of sodium azide in 50 ml of water is added dropwise and the mixture is stirred for 1 hour. 100 ml of acetone are evaporated off under vacuum at RT, saturated $NaHCO_3$ solution is added to the remaining solution, the mixture is extracted with toluene, the organic phase is washed with water and with saturated NaCl solution and dried over $Na_2SO_4$ and 50% by volume of the solvent is evaporated off. The remaining toluene solution is refluxed for 30 minutes and then concentrated under vacuum. The residue is taken up with 200 ml of ether, a solution of 7.1 g of pyrrolidine in 20 ml of ether is added dropwise and the mixture is stirred for 5 minutes. It is concentrated under vacuum, the residue is extracted with DCM, the organic phase is washed with 2N HCl solution, with 5% $NaHCO_3$ solution and with saturated NaCl solution and dried over $Na_2SO_4$ and the solvent is evaporated off under vacuum. The residue is dissolved in 40 ml of hot AcOEt, 200 ml of ether are added and the crystalline product formed is wrung to give 31.4 g of the expected product.

C) 4-Phenyl-4-(pyrrolidin-1-ylcarbonylamino)piperidine benzenesulfonate

A mixture of 29 g of the compound obtained in the previous step, 11.27 g of benzenesulfonic acid, 2 g of 10% palladium-on-charcoal and 250 ml of EtOH is hydrogenated at 40° C. and at atmospheric pressure. The catalyst is filtered off on Célite® and the filtrate is concentrated under vacuum. The residue is crystallized from an EtOH/acetone mixture to give 29.4 g of the expected product. M.p.=185° C.

Preparation 2.7

4-[2-(Dimethylamino)thiazol-4-yl]-4-phenylpiperidine p-toluenesulfonate

A) 1,1-Dimethylthiourea

A solution of 10.67 g of potassium thiocyanate in 100 ml of acetone is cooled in an ice bath, a solution of 12.06 g of pivaloyl chloride in 30 ml of acetone is added dropwise and the reaction mixture is stirred for 30 minutes while the temperature is allowed to rise to RT. It is cooled to −10° C., 17.9 ml of a 5.6N solution of dimethylamine in MeOH are added dropwise and the mixture is stirred while the temperature is allowed to rise to RT. It is concentrated under vacuum, the residue is extracted with ether, the organic phase is washed twice with water and with saturated NaCl solution and dried over $MgSO_4$ and the solvent is evaporated off under vacuum. The product obtained is taken up with 50 ml of concentrated HCl solution and refluxed for 1 hour. After cooling to RT, the reaction mixture is washed twice with ether, the aqueous phase is rendered alkaline to pH 9 by the addition of 30% NaOH solution and extracted with DCM, the organic phase is washed with 5% NaOH solution and with saturated NaCl solution and dried over $MgSO_4$ and the solvent is evaporated off under vacuum. The residue is taken up with ether and the precipitate formed is wrung to give 6.7 g of the expected product.

B) 4-(2-Bromoacetyl)-4-phenylpiperidine hydrobromide 7.9 g of bromine are added rapidly at RT to a suspension of 14 g of 4-acetyl-4-phenylpiperidine hydrobromide in 200 ml of DCM and the reaction mixture is stirred overnight at RT. It is diluted by the addition of 200 ml of ether and the precipitate formed is wrung and washed with ether to give 16.7 g of the expected product after drying under vacuum.

C) 4-[2-(Dimethylamino)thiazol-4-yl]-4-phenylpiperidine p-toluenesulfonate

A mixture of 7.26 g of the compound obtained in step B) and 2.08 g of the compound obtained in step A) in 150 ml of EtOH is refluxed for 1 hour 30 minutes. After cooling to RT, the mixture is concentrated under vacuum, the residue is taken up with water, rendered alkaline to pH 10 by the addition of 10% NaOH solution and extracted with DCM, the organic phase is washed with 10% NaOH solution and with saturated NaCl solution and dried over $MgSO_4$ and the solvent is evaporated off under vacuum. The product obtained is dissolved in acetone, a solution of 3.31 g of p-toluenesulfonic acid monohydrate in 10 ml of acetone is added dropwise and the crystalline product formed is wrung to give 6.1 g of the expected product. M.p.=164° C.

Preparation 2.8

4-(Morpholin-4-ylcarbonylamino)-4-phenylpiperidine p-toluenesulfonate monohydrate A) 1-tert-Butoxycarbonyl-4-(morpholin-4-ylcarbonylamino)-4-phenylpiperidine A solution of 1.74 g of morpholine in 10 ml of acetone is added dropwise at RT to a solution of 6 g of the compound obtained in step A of Preparation 2.4 in 100 ml of acetone. The reaction mixture is concentrated under vacuum, the residue is extracted with AcOEt, the organic phase is washed with a buffer solution of pH 2 and with saturated NaCl solution and dried over $MgSO_4$ and the solvent is evaporated off under vacuum to give 7.1 g of the expected product.

B) 4-(Morpholin-4-ylcarbonylamino)-4-pheylpiperidine p-toluenesulfonate monohydrate 15 ml of concentrated HCl solution are added to a solution of 7.1 g of the compound obtained in the previous step in 100 ml of MeOH and the reaction mixture is stirred overnight at RT. It is concentrated under vacuum, the residue is taken up with water, rendered alkaline to pH 10 by the addition of concentrated NaOH solution and extracted three times with DCM, the combined organic phases are washed with saturated NaCl solution and dried over $MgSO_4$ and the solvent is evaporated off under vacuum. The product obtained is dissolved in acetone, a solution of 3.46 g of p-toluenesulfonic acid monohydrate in 10 ml of acetone is added dropwise and the mixture is concentrated under vacuum. The residue is taken up with ether and the precipitate formed is wrung to give 7 g of the expected product. M.p.=93° C.

Preparation 2.9

4-Phenyl-4-(pyrrolidin-1-ylaminocarbonyl)piperidine benzenesulfonate

A) 1-(Benzyloxycarbonyl)-4-phenyl-4-(pyrrolidin-1-ylaminocarbonyl)piperidine benzenesulfonate A mixture of 11.54 g of the compound obtained in step A of Preparation 2.6 and 100 ml of 1,2-dichloroethane is heated to the reflux temperature, 16.18 g of thionyl chloride are then added and the reaction mixture is refluxed for 1 hour and stirred overnight at RT. It is concentrated under vacuum, the residue is dissolved in 100 ml of DCM and cooled to 5° C. and 10.3 g of triethylamine and then 5 g of 1-aminopyrrolidine hydrochloride are added successively. After stirring for 1 hour, the reaction mixture is concentrated under vacuum, the residue is extracted with AcOEt, the organic phase is washed with water and with saturated NaCl solution and dried over $MgSO_4$ and the solvent is evaporated off under vacuum. The product obtained is dissolved in acetone, ether is added until precipitation occurs, and the precipitate formed is wrung. The precipitate is dissolved in ETCH, 2.61 g of benzenesulfonic acid are added and the precipitate formed is wrung to give 9.34 g of the expected product.

B) 4-Phenyl-4-(pyrrolidin-1-ylaminocarbonyl)piperidine benzenesulfonate

A mixture of 9.34 g of the compound obtained in the previous step, 1 g of 5% palladium-on-charcoal and 200 ml of EtCH is hydrogenated for 3 hours at 40° C. and at atmospheric pressure. The catalyst is filtered off and the filtrate is concentrated under vacuum to give 6.13 g of the expected product after crystallization from an EtOH/acetone mixture.

Preparation 2.10

4-Benzyl-4-(pyrrolidin-1-ylcarbonylamino)piperidine p-toluenesulfonate

A) 4-Cyanopiperidine 25 g of isonipecotamide (or piperidine-4-carboxamide) are added in small portions to 70 ml of $POCl_3$ and the reaction mixture is refluxed for 4 hours. It is concentrated under vacuum, the residue is taken up with ice, rendered alkaline to pH 13 by the addition of concentrated NaOH solution and extracted with DCM and then 4 times with ether, the combined organic phases are dried over $MgSO_4$ and the solvents are evaporated off under vacuum. The oil obtained is distilled under reduced pressure to give 6.4 g of the expected product. B.p.=108°–110° C. under 2400 Pa.

B) 4-Cyano-1,4-dibenzylpiperidine

A solution of 15 g of the compound obtained in the previous step in 250 ml of THF is cooled to –50° C., 190 ml of a 1.5M solution of lithium diisopropylamide in cyclohexane are added dropwise and the mixture is stirred for 30 minutes at –50° C. 34 ml of benzyl bromide are then added and the reaction mixture is stirred while the temperature is allowed to rise to RT. After 3 hours at RT, it is poured into a mixture of ice and concentrated HCl, ether is added and the precipitate formed is wrung and washed with water. The precipitate is taken up with water, rendered alkaline to pH 13 by the addition of concentrated NaOH solution and extracted with ether, the organic phase is dried over $MgSO_4$ and the solvent is evaporated off under vacuum to give 31.7 g of the expected product after crystallization from pentane. M.p.= 92° C.

C) 1,4-Dibenzyl-4-carboxypiperidine 6 g of the compound obtained in the previous step are added to a solution of 25 ml of water, 25 ml of concentrated $H_2SO_4$ and 25 ml of AcOH and the reaction mixture is heated at 140° C. for 5 hours. After cooling, it is poured onto ice, the pH is brought to 6.5 by the addition of concentrated NaOH solution and the mixture is stirred until crystallization occurs. The crystalline product is wrung and washed with water. The product is taken up with MeOH, wrung and washed with ether to give 3 g of the expected product. M.p.=262° C.

D) 1,4-Dibenzyl-4-isocyanatopiperidine

A mixture of 2 g of the compound obtained in the previous step and 1.6 g of phosphorus pentachloride in 40 ml of chloroform is heated at 60° C. for 1 hour. The reaction mixture is concentrated under vacuum, the residue is taken up with 40 ml of acetone, a solution of 2 g of sodium azide in 5 ml of water is added and the mixture is stirred for 30 minutes at RT. It is concentrated under vacuum at RT, the residue is taken up with ether, the organic phase is washed with saturated $Na_2CO_3$ solution and with water and dried over $MgSO_4$ and the solvent is evaporated off under vacuum. The residue is taken up with 40 ml of toluene and refluxed for 1 hour. It is concentrated under vacuum to give 2 g of the expected product in the form of an oil.

E) 1,4-Dibenzyl-4-(pyrrolidin-1-ylcarbonylamino)piperidine 1.5 ml of pyrrolidine are added at RT to solution of 5 g of the compound obtained in the previous step in 50 ml of DCM and the reaction mixture is stirred for 2 hours at RT. It is concentrated under vacuum, the residue is taken up with pentane and the precipitate formed is wrung and washed wit pentane to give 4.5 g of the expected product after drying. M.p.=126° C.

F) 4-Benzyl-4-(pyrrolidin-1-ylcarbonylamino)piperidine p-toluenesulfonate

A mixture of 4.2 g of the compound obtained in the previous step, 2.1 g of p-toluenesulfonic acid monohydrate, 0.4 g of 10% palladium-on-charcoal and 50 ml of EtOH is hydrogenated for 48 hours at RT and at atmospheric pressure. The catalyst is filtered off Célite® and the filtrate is concentrated under vacuum. The residue is taken up with ether and the precipitate formed is wrung to give 4.99 g of the expected product. M.p.>180° C.

Preparation 2.11

4-(Methoxycarbonylamino)-4-phenylpiperidine p-toluenesulfonate hemihydrate

A solution of 6.05 g of the compound obtained in step A of Preparation 2.4 in 100 ml of MeOH is refluxed for 5 hours. 1 drop of triethylamine is added and the mixture is stirred overnight at RT. Concentrated HCl solution is then added until the pH is 1, and the reaction mixture is concentrated under vacuum The residue is taken up with 10% NaOH solution an extracted with DCM, the organic phase is washed wit 10% NaOH solution and with saturated NaCl solution an dried over $MgSO_4$ and the solvent is evaporated of under vacuum. The product obtained is dissolved in acetone, a solution of 3.57 g of p-toluenesulfonic acid monohydrate in 10 ml of acetone is added dropwise and the mixture is concentrated under vacuum. The product obtained is taken up with ether and the solvent is evaporated off under vacuum to give 7.17 g of the expected product. M.p.=159° C.

Preparation 2.12

4-(2-Amino-1,3,4-oxadiazol-5-yl)-4-phenylpiperidine p-toluenesulfonate hemihydrate A) 1-(Benzyloxycarbonyl)-4-(chloroformyl)-4-phenylpiperidine A mixture of 17.1 g of the compound obtained in step A of Preparation 2.6 and 24 g of thionyl chloride in 150 ml of 1,2-dichloroethane is refluxed for 1 hour. It is concentrated under vacuum, the residue is taken up with chloroform and the solvent is evaporated off under vacuum. The residue is taken up with an ether/pentane mixture and the solvents are evaporated off under vacuum again to give 20 g of the expected product in the form of a gum, which is used as such.

B) 1-(Benzyloxycarbonyl)-4-carbazoyl-4-phenylpiperidine

A solution of 16 g of hydrazine monohydrate in 40 ml of EtOH is cooled to −50° C., a solution of 11.44 g of the compound obtained in the previous step in 20 ml of 1,2-dimethoxyethane is added dropwise and the mixture is stirred while the temperature is allowed to rise to RT. It is concentrated under vacuum, the residue is taken up with water and extracted with DCM, the organic phase is washed with water and with saturated NaCl solution and dried over $MgSO_4$ and the solvent is evaporated off under vacuum. The residue is taken up with an EtOH/benzene mixture and the solvents are evaporated off under vacuum to give 11.2 g of the expected product in the form of a gum, which is used as such.

C) 4-(2-Amino-1,3,4-oxadiazol-5-yl)-1-(benzyloxycarbonyl)-4-phenylpiperidine

A solution of 3.39 g of cyanogen bromide in 10 ml of EtOH is added at RT to a solution of 11.2 g of the compound obtained in the previous step in 60 ml of EtOH and the reaction mixture is refluxed for 1 hour It is concentrated to 50 ml of EtOH and water is the added dropwise until the volume of the reaction mixture is 400 ml. The crystalline product formed is wrung and washed with water and then with DCM, with AcOEt and with ether to give 8 g of the expected product.

D) 4-(2-Amino-1,3,4-oxadiazol-5-yl)-4-phenylpiperidine p-toluenesulfonate hemihydrate A mixture of 7.85 g of the compound obtained in the previous step, 3.95 g of p-toluenesulfonic acid monohydrate, 0.8 g of 10% palladium-on-charcoal, 350 ml of 95° EtOH and 10 ml of water is hydrogenated at 50° C. and at atmospheric pressure. After 3 hours, the catalyst is filtered off on Célite® and the filtrate is concentrated under vacuum. The residue is taken up with acetone and the crystalline product formed is wrung and washed with acetone and then with ether to give 7.65 g of the expected product. M.p.=183°–185° C.

Preparation 2.13

4-[(Acetyl-N-methylamino)methyl]-4-phenylpiperidine p-toluenesulfonate

A) 4-(Aminomethyl)-1-benzyl-4-phenylpiperidine

A suspension of 2.8 g of lithium aluminum hydride in 50 ml of THF is cooled to 0° C. and a solution of 20 g of 1-benzyl-4-cyano-4-phenylpiperidine in 50 ml of THF is added dropwise. The reaction mixture is stirred for 1 hour at RT and then heated for 1 hour at 40° C. It is cooled in an ice bath and 3 ml of water, 3 ml of 4N NaOH solution and 12 ml of water are added successively. The mineral salts are filtered off and the filtrate is evaporated under vacuum. The residue is chromatographed on silica H using a gradient of a DCM/MeOH mixture (from 100/3; v/v to 100/10; v/v) as the eluent to give 11 g of the expected product.

B) 1-Benzyl-4-[(N-formylamino)methyl]-4-phenylpiperidine 25 ml of acetic anhydride are added dropwise at RT to a mixture of 11 g of the compound obtained in the previous step in 76 ml of formic acid and the reaction mixture is then stirred for 5 hours. It is concentrated under vacuum, the residue is taken up with water, rendered alkaline to pH 1 4 by the addition of concentrated NaOH and extracted with ether, the extract is washed with water and dried over $Na_2SO_4$ and the solvent is evaporated off under vacuum to give 12 g of the expected product.

C) 1-Benzyl-4-[(N-methylamino)methyl]-4-phenylpiperidine

A suspension of 3.9 g of lithium aluminum hydride in 50 ml of THF is heated to 40° C., a solution of 12 g of the compound obtained in the previous step in 50 ml of THF is added dropwise and the mixture is then refluxed for 3 hours. After cooling in an ice bath, 4 ml of water, 4 ml of 4N NaOH solution and 12 ml of water are added successively. The mineral salts are filtered off and the filtrate is concentrated under vacuum. The residue is extracted with ether, the extract is dried over $Na_2SO_4$ and the solvent is evaporated off under vacuum to give 10 g of the expected product.

D) 4-[(Acetyl-N-methylamino)methyl]-1-benzyl-4-phenylpiperidine 0.863 g of acetyl chloride is added to a solution of 3.3 g of the compound obtained in the previous step and 1.4 g of triethylamine in 50 ml of DCM and the reaction mixture is stirred for 2 hours at RT. It is concentrated under vacuum, the residue is taken up with water and extracted with ether, the extract is washed with water and dried over $Na_2SO_4$ and the solvent is evaporated off. The residue is chromatographed on silica H using a DCM/MeOH mixture (100/3; v/v) as the eluent to give 2.4 g of the expected product.

E) 4-[(Acetyl-N-methylamino)methyl]-4-phenylpiperidine p-toluenesulfonate

A mixture of 2.3 g of the compound obtained in the previous step, 1.2 g of p-toluenesulfonic acid monohydrate, 0.23 g of 10% palladium-on-charcoal and 100 ml of MeOH is hydrogenated at RT and at atmospheric pressure. The catalyst is filtered off and the filtrate is evaporated under vacuum to give 2.7 g of the expected product after in trituration ether and wringing.

Preparation 2.14

4-[(Ethoxycarbonyl-N-methylamino)methyl]-4-phenylpiperidine p-toluenesulfonate

A) 1-Benzyl-4-[(ethoxycarbonyl-N-methylamino)methyl]-4-phenylpiperidine

A solution of 0.85 g of ethyl chloroformate in 10 ml of DCM is added dropwise at RT to a solution of 2.3 g of the compound obtained in step C of Preparation 2.13 and 1.03 g of triethylamine in 50 ml of DCM and the reaction mixture is stirred for 30 minutes at RT. It is concentrated under vacuum, the residue is taken up with water and extracted with ether, the organic phase is washed with water and with saturated NaCl solution and dried over $Na_2SO_4$ and the solvent is evaporated off under vacuum. The residue is chromatographed on silica H using a DCM/MeOH mixture (100/3; v/v) as the eluent to give 2.3 g of the expected product.

B) 4-[(Ethoxycarbonyl-N-methylamino)methyl]-4-phenylpiperidine p-toluenesulfonate A mixture of 2.3 g of the compound obtained in the previous step, 1.19 g of p-toluenesulfonic acid monohydrate, 0.7 g of 5% palladium-on-charcoal and 50 ml of DCM is hydrogenated at 40° C. and at atmospheric pressure. The catalyst is filtered off on Célite® and the filtrate is concentrated under vacuum to give 2.7 g of the expected product.

Preparation 2.15

4-[(N',N'-Dimethyl-N-methylureido)methyl]-4-phenylpiperidine p-toluenesulfonate

A) 1-Benzyl-4-[(N',N'-dimethyl-N-methylureido)methyl]-4-phenylpiperidine

A solution of 0.92 g of N,N-dimethylcarbamoyl chloride in 20 ml of DCM is added dropwise at RT to a solution of 2.5 g of the compound obtained in step C of Preparation 2.13 and 1.11 g of triethylamine in 50 ml of DCM and the reaction mixture is then refluxed for 3 hours. It is concentrated under vacuum, the residue is taken up with water and extracted with ether, the organic phase is washed with water and with saturated NaCl solution and dried over $Na_2SO_4$ and the solvent is evaporated off under vacuum. The residue is chromatographed on silica H using a DCM/MeOH mixture (100/3; v/v) as the eluent to give 2.92 g of the expected product.

B) 4-[(N',N'-Dimethyl-N-methylureido)methyl]-4-phenylpiperidine p-toluenesulfonate A mixture of 2.92 g of the compound obtained in the previous step, 1.52 g of p-toluenesulfonic acid monohydrate, 0.3 g of 10% palladium-on-charcoal and 50 ml of MeOH is hydrogenated at 40° C. and at atmospheric pressure. The catalyst is filtered off on Célite® and the filtrate is concentrated under vacuum to give 2.6 g of the expected product after trituration of the residue in a pentane/iso ether mixture, followed by wringing.

Preparation 2.16

4-Carbamoyl-4-(piperid-1-yl)piperidine dihydrochloride

A) 1-Benzyl-4-cyano-4-(piperid-1-yl)piperidine

A solution of 5.3 g of sodium cyanide in 20 ml of water is added dropwise at RT to a solution of 18.9 g of 1-benzylpiperid-4-one and 12.16 g of piperidine hydrochloride in 25 ml of MeOH and 25 ml of water and the mixture is stirred for 48 hours at RT. The precipitate formed is wrung, washed with water and dried under vacuum to give 27 g of the expected product.

B) 1-Benzyl-4-carbamoyl-4-(piperid-1-yl)piperidine 10 g of the compound obtained in the previous step are added to 50 ml of 95% sulfuric acid and the reaction mixture is heated at 100° C. for 45 minutes. After cooling to RT, it is poured onto 100 g of ice, 250 ml of DCM are added, with cooling, the organic phase is decanted and dried over $MgSO_4$ and the solvent is evaporated off under vacuum. The solid product obtained is recrystallized from 300 ml of an acetonitrile/toluene mixture (65/35; v/v) to give 9.7 g of the expected product. M.p.=150°–160° C.

C) 4-Carbamoyl-4-(piperid-1-yl)piperidine dihydrochloride 10 g of ammonium formate and 2.5 g of 5% palladium-on-charcoal are added to a solution of 9.7 g of the compound obtained in the previous step in 200 ml of MeOH and the mixture is stirred for 2 hours at RT. It is filtered on Célite® and the filtrate is evaporated under vacuum. The residue is dissolved in 2N HCl solution, rendered alkaline to pH 13 by the addition of 40% NaOH solution and extracted with chloroform, the organic phase is dried over $MgSO_4$ and the solvent is evaporated off under vacuum. The product obtained is dissolved in an MeOH/DCM mixture, acidified to pH 1 by the addition of a saturated solution of hydrochloric acid in ether and evaporated under vacuum to give 5 g of the expected product. M.p.=185° C.

Preparation 2.17

4-Phenyl-4-ureidopiperidine benzenesulfonate

A) 1-(Benzyloxycarbonyl)-4-isocyanato-4-phenylpiperidine

A mixture of 50.89 g of the compound obtained in step A) of Preparation 2.6 and 71.4 g of thionyl chloride in 400 ml of 1,2-dichloroethane is refluxed for 1 hour. The reaction mixture is concentrated under vacuum, the residue is taken up with acetone and the solvent is evaporated off under vacuum. The residue is dissolved in 200 ml of acetone and cooled to 5° C., a solution of 19.5 g of sodium azide in 50 ml of water is added dropwise and the mixture is stirred for 2 hours at RT. The acetone is evaporated off under vacuum at RT, saturated $NaHCO_3$ solution is added to the remaining solution, the mixture is extracted with toluene, the organic phase is washed with water and with saturated NaCl solution and dried over $Na_2SO_4$ and 50% by volume of the solvent is evaporated off. The remaining toluene solution is refluxed for 1 hour and then concentrated under vacuum to give 54 g of the expected product in the form of an orange oil, which crystallizes.

B) 1-(Benzyloxycarbonyl)-4-phenyl-4-ureidopiperidine

Excess ammonia gas is bubbled at RT into a solution of 29 g of the compound obtained in the previous step in 300 ml of ether and 300 ml of DCM and the reaction mixture is then stirred overnight at RT. It is concentrated under vacuum, the residue is taken up with hot acetone and the temperature is allowed to drop to RT. As soon as the product crystallizes, an ether/AcOEt mixture is added and the crystals formed are then wrung to give 26.4 g of the expected product.

C) 4-Phenyl-4-ureidopiperidine benzenesulfonate

A mixture of 25 g of the compound obtained in the previous step, 11.2 g of benzenesulfonic acid, 3 g of 5% palladium-on-charcoal and 300 ml of EtOH is hydrogenated at 40° C. and at atmospheric pressure. The reaction mixture is diluted by the addition of water and MeOH, the catalyst is filtered off on Célite® and the filtrate is concentrated under vacuum to give 26.45 g of the expected product after crystallization from acetone. M.p.=235° C.

Preparation 2.18

4-(N'-Methylureido)-4-phenylpiperidine benzenesulfonate

A) 1-(Benzyloxycarbonyl)-4-(N'-methylureido)-4-phenylpiperidine

A solution of 25 g of the compound obtained in step A of Preparation 2.17 in 300 ml of ether is cooled to 5° C. and excess gaseous methylamine is bubbled in. The reaction mixture is diluted by the addition of 15 ml of DCM and stirred overnight at RT. It is concentrated under vacuum, the residue is taken up with hot AcOEt and the temperature is allowed to return to RT. Ether is added until precipitation occurs, and the precipitate formed is wrung to give 24 g of the expected product.

B) 4-(N'-Methylureido)-4-phenylpiperidine benzenesulfonate

A mixture of 23 g of the compound obtained in the previous step, 9.9 g of benzenesulfonic acid, 3 g of 5% palladium-on-charcoal and 300 ml of 95° EtOH is hydrogenated at 40° C. and at atmospheric pressure. The catalyst is filtered off on Célite® and the filtrate concentrated under vacuum. The residue is taken up with acetone and the precipitate formed is wrung to give 22.36 g of the expected product. M.p.=227° C.

Preparation 2.19

4-(3,3-Dimethylcarbazoyl)-4-phenylpiperidine p-toluenesulfonate

A) 1-(Benzyloxycarbonyl)-4-(3,3- dimethylcarbazoyl)-4-phenylpiperidine p-toluenesulfonate A solution of 7.15 g of the compound obtained in step A of Preparation 2.12 in 60 ml of DCM is cooled to 5° C., a solution of 1.44 g of 1,1-dimethylhydrazine and 4.04 g of triethylamine in 20 ml of DCM is added dropwise and the reaction mixture is stirred overnight at RT. It is concentrated under vacuum, the residue is taken up with water and extracted with AcOEt, the organic phase is washed with saturated NaCl solution and dried over $Na_2SO_4$ and the solvent is evaporated off under vacuum. The product obtained is dissolved in 100 ml of acetone, a solution of 3.59 g of p-toluenesulfonic acid monohydrate in 10 ml of acetone is added rapidly and the mixture is concentrated under vacuum. The residue is taken up with an ether/DCM mixture and the precipitate formed is wrung to give 9.65 g of the expected product.

B) 4-(3,3-Dimethylcarbazoyl)-4-phenylpiperidine p-toluenesulfonate

A mixture of 9.5 g of the compound obtained in the previous step and 0.9 g of 10% palladium-on-charcoal in 100 ml of 95° EtOH is hydrogenated at 30° C. and at atmospheric pressure. The catalyst is filtered off on Célite® and the filtrate is concentrated under vacuum. The residue is taken up with 100 ml of acetone and the crystalline product formed is wrung and washed with ether to give 7 g of the expected product.

M.p.=210°–212° C.

Preparation 2.20

4-[(Ethylaminocarbonyloxy)methyl]-4-phenylpiperidine hydrochloride

A) 4-Methoxycarbonyl-4-phenylpiperidine p-toluenesulfonate 1 g of p-toluenesulfonic acid monohydrate is added to a solution of 10 g of 4-carboxy-4-phenylpiperidine p-toluenesulfonate in 300 ml of MeOH and the reaction mixture is refluxed for 3 days. It is concentrated under vacuum, the residue is taken up with acetone, and ether is added until precipitation occurs. 9.34 g of the expected product are obtained after wringing of the precipitate formed.

B) 4-Hydroxymethyl-4-phenylpiperidine

A suspension of 1.16 g of lithium aluminum hydride in 50 ml of THF is cooled to −20° C., 4 g of the compound obtained in the previous step are added and the mixture is stirred overnight while the temperature is allowed to rise to RT. It is hydrolyzed by the addition of 1.2 ml of water and then 2.5 ml of 10% NaOH solution and 2.5 ml of water. The mixture is diluted with ether, the mineral salts are filtered off and the filtrate is evaporated under vacuum to give 1.8 g of the expected product.

C) 1-tert-Butoxycarbonyl-4-(hydroxymethyl)-4-phenylpiperidine 26.05 g of di-tert-butyl dicarbonate are added to a solution of 22.8 g of the compound obtained in the previous step in 250 ml of 1,2-dimethoxyethane and the reaction mixture is refluxed for 2 hours. It is concentrated under vacuum, the residue is taken up with DCM, the organic phase is washed with a buffer solution of pH 2 and with saturated NaCl solution and dried over $MgSO_4$ and the solvent is evaporated off under vacuum to give 17.86 g of the expected product after crystallization from ether. M.p.=134° C.

D) 1-tert-Butoxycarbonyl-4-[(ethylaminocarbonyloxy)methyl]-4-phenylpiperidine

A mixture of 2.91 g of the compound obtained in the previous step, 2.4 g of ethyl isocyanate and 2 drops of triethylamine in 30 ml of toluene is stirred overnight at RT. The reaction mixture is then heated at 100° C. for 24 hours and concentrated under vacuum. The residue is taken up with ether, the organic phase is washed with a buffer solution of pH 2 and with saturated NaCl solution and dried over $MgSO_4$ and the solvent is evaporated off under vacuum to give 3.85 g of the expected product in the form of an oil.

E) 4-[(Ethylaminocarbonyloxy)methyl]-4-phenylpiperidine hydrochloride 10 ml of concentrated HCl are added to a solution of 3.85 g of the compound obtained in the previous step in 50 ml of MeOH and the mixture is heated at 60° C. for 2 hours. It is concentrated under vacuum, the residue is taken up with acetone and the solvent is evaporated off under vacuum to give 2.6 g of the expected product after crystallization from an AcOEt/ether mixture. M.p.=240°–242° C.

Preparation 2.21

4-(Acetoxymethyl)-4-phenylpiperidine 0.785 g of acetyl chloride is added at RT to a solution of 2.91 g of the compound obtained in step C of Preparation 2.20 and 1.31 g of triethylamine in 50 ml of DCM and the mixture is stirred for 30 minutes at RT. It is concentrated under vacuum, the residue is taken up with water and extracted with AcOEt, the organic phase is washed twice with water and with saturated NaCl solution and dried over $MgSO_4$ and the solvent is evaporated off under vacuum. The oily residue is taken up with 20 ml of trifluoroacetic acid and the mixture is stirred for 10 minutes at RT. It is concentrated under vacuum, the residue is taken up with water, the aqueous phase is rendered alkaline to pH 1 1 by the addition of concentrated NaOH solution and extracted with DCM, the organic phase is washed 5 times with water and with saturated NaCl solution and dried over $MgSO_4$ and the solvent is evaporated off under vacuum to give 1.6 g of the expected product.

Preparation 2.22

4-Benzyl-4-[(ethoxycarbonyl-N-methylamino) methyl]piperidine benzenesulfonate

A) 1-Benzyl-4-carbamoylpiperidine 85.5 g of benzyl bromide are added dropwise at RT to a mixture of 58.2 g of isonipecotamide and 69 g of $K_2CO_3$ in 275 ml of DMF and the reaction mixture is stirred for 2 hours at 50° C. It is concentrated under vacuum, the residue is taken up with water and extracted with DCM, the organic phase is washed with water and dried over $Na_2SO_4$ and the solvent is evaporated off under vacuum to give 62 g of the expected product after crystallization from 300 ml of water and drying under vacuum.

B) 1-Benzyl-4-cyanopiperidine

A mixture of 62 g of the compound obtained in the previous step and 200 ml of $POCl_3$ is refluxed for 2 hours. It is concentrated under vacuum, the residue is taken up with water, rendered alkaline to pH 13 by the addition of concentrated NaOH solution and extracted with DCM, the organic phase is washed with water and dried over $Na_2SO_4$ and the solvent is evaporated off under vacuum. The oil obtained is distilled under reduced pressure to give 52 g of the expected product.

B.p.=120° C. under 10 Pa.

C) 1,4-Dibenzyl-4-cyanopiperidine 200 ml of a 1.5M solution of lithium diisopropylamide in cyclohexane, diluted in 100 ml of THF, are cooled to −50° C., a solution of 52 g of the compound obtained in the previous step in 100 ml of THF is added dropwise and the mixture is stirred for 30 minutes at −50° C. A solution of 51.3 g of benzyl bromide in 100 ml of THF is then added dropwise at a temperature between −30° C. and −25° C. and the mixture is stirred while the temperature is allowed to rise to RT. It is concentrated under vacuum, the residue is taken up with water and extracted with ether, the organic phase is washed with water and dried over $Na_2SO_4$ and the solvent is evaporated off under vacuum to give 64 g of the expected product after crystallization from pentane.

D) 4-(Aminomethyl)-1,4-dibenzylpiperidine

A solution of 14.5 g of the compound obtained in the previous step in 50 ml of THF is added dropwise at RT to a suspension of 1.95 g of lithium aluminum hydride in 50 ml of THF and the mixture is then refluxed for 6 hours. After cooling to RT, 2 ml of water, 2 ml of 4N NaOH solution and 6 ml of water are added. The mineral salts are filtered off on Célite®, the filtrate is decanted, the organic phase is dried over $Na_2SO_4$ and the solvent is evaporated off under vacuum to give 14.7 g of the expected product.

E) 1,4-Dibenzyl-4-[(formylamino)methyl]piperidine 42 ml of acetic anhydride are added dropwise at RT to a solution of 14.7 g of the compound obtained in the previous step in 126 ml of formic acid and the mixture is stirred for 3 hours at RT. It is concentrated under vacuum, the residue is taken up with water, rendered alkaline to pH 13 by the addition of concentrated NaOH solution and extracted with AcOEt, the organic phase is washed with water and dried over $Na_2SO_4$ and the solvent is evaporated off under vacuum to give 14.5 g of the expected product.

F) 1,4-Dibenzyl-4-[(methylamino)methyl]piperidine

A solution of 14.5 g of the compound obtained in the previous step in 100 ml of THF is added dropwise at 40° C. to a suspension of 5 g of lithium aluminum hydride in 100 ml of THF and the mixture is then refluxed for 4 hours. After cooling to RT, 5 ml of water, 5 ml of 4N NaOH solution and 15 ml of water are added. The mineral salts are filtered off on Célite®, the filtrate is decanted, the organic phase is dried over $Na_2SO_4$ and the solvent is evaporated off under vacuum to give 12.8 g of the expected product.

G) 1,4-Dibenzyl-4-[(ethoxycarbonyl-N-methylamino) methyl]piperidine 1.26 g of ethyl chloroformate are added dropwise at RT to a solution of 3 g of the compound obtained in the previous step and 1.18 g of triethylamine in 50 ml of 1,2-dichloroethane and the mixture is stirred for 1 hour at RT. It is concentrated under vacuum, the residue is taken up with water and extracted with ether, the organic phase is dried over $Na_2SO_4$ and the solvent is evaporated off under vacuum. The residue is chromatographed on silica H using a DCM/MeOH mixture (100/3; v/v) as the eluent to give 1.6 g of the expected product.

H) 4-Benzyl-4-[(ethoxycarbonyl-N-methylamino)methyl] piperidine benzenesulfonate A mixture of 1.6 g of the compound obtained in the previous step, 0.66 g of benzenesulfonic acid, 0.2 g of 10% palladium-on-charcoal and 30 ml of MeOH is hydrogenated at 27° C. and at atmospheric pressure. The catalyst is filtered off on Célite® and the filtrate is concentrated under vacuum to give 1.44 g of the expected product.

Preparation 2.23

4-Benzyl-4-[(methanesulfonyl-N-methylamino) methyl]piperidine benzenesulfonate

A) 1,4-Dibenzyl-4-[(methanesulfonyl-N-methylamino) methyl]piperidine 1.26 g of methanesulfonyl chloride are added dropwise at RT to a solution of 3.2 g of the compound obtained in step F of Preparation 2.22 and 1.26 g of triethylamine in 50 ml of 1,2-dichloroethane and the mixture is stirred for 1 hour at RT. It is concentrated under vacuum, the residue is taken up with water and extracted with AcOEt, the organic phase is dried over $Na_2SO_4$ and the solvent is evaporated off under vacuum to give 3.8 g of the expected product.

B) 4-Benzyl-4-[(methanesulfonyl-N-methylamino)methyl] piperidine benzenesulfonate A mixture of 3.8 g of the compound obtained in the previous step, 1.58 g of benzenesulfonic acid, 0.8 g of 10% palladium-on-charcoal and 30; ml of MeOH is hydrogenated at RT and at atmospheric pressure. The catalyst is filtered off on Célite® and the filtrate is concentrated under vacuum to give 4.6 g of the expected product after crystallization from a DCM/ether mixture.

Preparation 2.24

4-Benzyl-4-[(N',N'-dimethyl-N-methylureido) methyl]piperidine hydrochloride

A) 1,4-Dibenzyl-4-[(N',N'-dimethyl-N-methylureido) methyl]piperidine 1.12 g of N,N-dimethylcarbamoyl chloride are added dropwise at RT to a solution of 3.2 g of the compound obtained in step F of Preparation 2.22 and 1.2 g of triethylamine in 40 ml of 1,2-dichloroethane and the mixture is refluxed for 4 hours. It is concentrated under vacuum, the residue is taken up with water and extracted with ether, the organic phase is dried over $Na_2SO_4$ and the solvent is evaporated off under vacuum to give 3.6 g of the expected product.

B) 4-Benzyl-4-[(N',N'-dimethyl-N-methylureido)methyl] piperidine hydrochloride

A mixture of 3.6 g of the compound obtained in the previous step, 3.1 g of ammonium formate and 0.8 g of 5% palladium-on-charcoal in 50 ml of MeOH is stirred for 1 hour 30 minutes. The catalyst is filtered off and the solvent is evaporated off under vacuum. The residue is dissolved in DCM, a saturated solution of hydrochloric acid in ether is added until the pH is 1, and the solvents are evaporated off under vacuum to give 3.2 g of the expected product.

Preparation 2.25

4-Carbamoyl-4-(morpholin-4-yl)piperidine

A) 1-Benzyl-4-cyano-4-(morpholin-4-yl)piperidine 2.5 ml of morpholine and then 5.1 g of $Na_2S_2O_5$ are added to a mixture of 5 g of 1-benzylpiperid-4-one and 1.9 g of potassium cyanide in 50 ml of an EtOH/water mixture (50/50; v/v) and the mixture is heated at 60° C. for 2 hours. A further 2.5 ml of morpholine are added and the reaction mixture is stirred overnight at RT. Water is added and the crystalline product formed is wrung to give 5.5 g of of the expected product.

B) 1-Benzyl-4-carbamoyl-4-(morpholin-4-yl)piperidine

A mixture of 14 g of the compound obtained in the previous step and 50 ml of 95% sulfuric acid is heated at 100° C. for 2 hours. After cooling to RT, the reaction mixture is poured onto 100 g of ice, brought to pH 7 by the addition of concentrated $NH_4OH$ solution and extracted with DCM, the organic phase is washed with water and dried over $Na_2SO_4$ and the solvent is evaporated off under vacuum. The residue is chromatographed on silica H using a DCM/MeOH mixture (100/5; v/v to 100/10; v/v) as the eluent to give 3.4 g of the expected product after crystallization from iso ether.

C) 4-Carbamoyl-4-(morpholin-4-yl)piperidine 3.1 g of ammonium formate and 0.8 g of 5% palladium-on-charcoal are added to a solution of 3.4 g of the compound obtained in the previous step in 50 ml of MeOH and the mixture is stirred for 2 hours at RT. The catalyst is filtered off on Célite® and the filtrate is evaporated under vacuum to give 2.2 g of the expected product after crystallization from propan-2-ol.

EXAMPLE 1

3-Benzyl-5-[2-(4-benzylpiperid-1-yl)ethyl]-5-(3,4-dichlorophenyl)tetrahydro-2H-1,3-oxazin-2-one hydrochloride monohydrate A) 3-Benzyl-5-(3,4-dichlorophenyl)-5-[2-(tetrahydropyran-2-yloxy)ethyl]tetrahydro-2H-1,3-oxazin-2-one A solution of 4 g of the compound obtained in Preparation 1.1 in 60 ml of THF is cooled to +5° C., 1.37 g of potassium tert-butylate are added and a solution of 1.92 g of benzyl bromide in 15 ml of THF is then added dropwise. The reaction mixture is stirred while the temperature is allowed to rise to RT, and concentrated under vacuum. The residue is extracted with AcOEt, the organic phase is washed three times with water and twice with saturated NaCl solution and dried over $MgSO_4$ and the solvent is evaporated off under vacuum to give 4.2 g of the expected product, which is used as such.

B) 3-Benzyl-5-(3,4-dichlorophenyl)-5-(2-hydroxyethyl) tetrahydro-2H-1,3-oxazin-2-one 0.25 hydrate A saturated solution of gaseous HCl in ether is added to a solution of 4.2 g of the compound obtained in the previous step in 40 ml of MeOH until the pH is 1, and the reaction mixture is stirred for 48 hours at RT. It is concentrated under vacuum, the residue is taken up with a saturated solution of gaseous HCl in MeOH and the solvent is evaporated off under vacuum. The residue is taken up with ether and the precipitate formed is wrung to give 3.44 g of the expected product. M.p.=143° C.

C) 3-Benzyl-5-(3,4-dichlorophenyl)-5-[2-(methanesulfonyloxy)ethyl]tetrahydro-2H-1,3-oxazin-2-one A solution of 1.4 g of the compound obtained in the previous step and 0.45 g of triethylamine in 50 ml of DCM is cooled to +5° C. and a solution of 0.46 g of methanesulfonyl chloride in 5 ml of DCM is added dropwise. After the addition, the reaction mixture is concentrated under vacuum, the residue is taken up with water and extracted with AcOEt, the organic phase is washed twice with water and with saturated NaCl solution and dried over $MgSO_4$ and the solvent is evaporated off under vacuum to give 1.7 g of the expected product.

Proton NMR spectrum at 200 MHz in DMSO-$d_6$

| | |
|---|---|
| δ: | 2.03 ppm : t : 2H |
| | 2.98 ppm : s : 3H |
| | 3.78 ppm : AB system : 2H |
| | 3.83 ppm : t : 2H |
| | 4.1 to 4.8 ppm : u : 4H |
| | 7.0 to 7.6 ppm : u : 8H |

D) 3-Benzyl-5-[2-(4-benzylpiperid-1-yl)ethyl]-5-(3,4-dichlorophenyl)tetrahydro-2H-1,3-oxazin-2-one hydrochloride monohydrate A mixture of 1.6 g of 4-benzylpiperidine, 1.7 g of the compound obtained in the previous step and 0.6 g of potassium iodide in 10 ml of DMF is heated at 60° C. for 2 hours 30 minutes. After cooling to RT, the reaction mixture is poured into water and extracted with AcOEt, the organic phase is washed twice with water and with saturated NaCl solution and dried over $MgSO_4$ and the solvent is evaporated off under vacuum. The residue is chromatographed on silica H using DCM as the eluent. The product obtained is taken up with a saturated solution of gaseous HCl in ether and the precipitate formed is wrung to give 0.9 g of the expected product. M.p.=122° C.

EXAMPLE 2

3-Benzyl-5-(3,4-dichlorophenyl)-5-[2-(4-hydroxy-4-phenylpiperid-1-yl)ethyl]tetrahydro-2H-1,3-oxazin-2-one hydrochloride This compound is prepared by the procedure described in step D of EXAMPLE 1 from 1.32 g of 4-hydroxy-4-phenylpiperidine, 1.55 g of the compound obtained in step C of EXAMPLE 1 and 0.56 g of potassium iodide in 10 ml of DMF. The residue is chromatographed on silica H using DCM and then a DCM/MeOH mixture (96/4; v/v) as the eluent. The product obtained is dissolved in DCM and acidified to pH 1 by the addition of a saturated solution of gaseous HCl in ether and the solvents are evaporated off under vacuum to give 0.72 g of the expected compound after crystallization from ether. M.p.=172° C.

EXAMPLE 3

5-[2-(4-Acetamido-4-phenylpiperid-1-yl)ethyl]-3-benzyl-5-(3,4-dichlorophenyl)tetrahydro-2H-1,3-oxazin-2-one hydrochloride 1.5 hydrate This compound is prepared by the procedure described in step D of EXAMPLE 1 from 2.77 g of 4-acetamido-4-phenylpiperidine, 1.7 g of the compound obtained in step C of EXAMPLE 1 and 0.61 g of potassium iodide in 10 ml of DMF. The residue is chromatographed on silica H using DCM and then a DCM/MeOH mixture (97/3; v/v) as the eluent. The residue is taken up with a saturated solution of gaseous HCl in ether and the solvent is evaporated off under vacuum to give 0.6 g of the expected product after crystallization from AcOEt. M.p.=168° C.

EXAMPLE 4

3-[3,5-Bis(trifluoromethyl)benzyl]-5-(3,4-dichlorophenyl)-5-[2-(4-phenylpiperid-1-yl)ethyl] tetrahydro-2H-1,3-oxazin-2-one hydrochloride hemihydrate A) 3-[3,5-Bis(trifluoromethyl)benzyl]-5-(3,4-dichlorophenyl)-5-[2-(tetrahydropyran-2-yloxy)ethyl] tetrahydro-2H-1,3-oxazin-2-one A solution of 3.7 g of the compound obtained Preparation 1.1 in 60 ml of THF is cooled to +5° C., 1.27 g of potassium tert-butylate are added and a solution of 2.72 g of 3,5-bis (trifluoromethyl)benzyl chloride in 15 ml of THF is then added dropwise. The reaction mixture is stirred while the temperature is allowed to rise to RT, and concentrated under vacuum. The residue is taken up with water and extracted with AcOEt, the organic phase is washed with water and with saturated NaCl solution and dried over $MgSO_4$ and the solvent is evaporated off under vacuum to give 5.9 g of the expected product, which is used as such.

B) 3-[3,5-Bis(trifluoromethyl)benzyl]-5-(3,4-dichlorophenyl)-5-(2-hydroxyethyl)tetrahydro-2H-1,3-oxazin-2-one A saturated solution of gaseous HCl in ether is added to a solution of 5.9 g of the compound obtained in the previous step in 50 ml of MeOH until the pH is 1, and the reaction mixture is stirred for 15 minutes at RT. It is concentrated under vacuum, the residue is taken up twice with a saturated solution of gaseous HCl in MeOH and the solvent is evaporated off under vacuum. The residue is taken up with hexane and the precipitate formed is wrung to give 3.9 g of the expected product.

Proton NMR spectrum at 200 MHz in DMSO-$d_6$

| | |
|---|---|
| δ: | 1.9 ppm : t : 2H |
| | 2.9 to 3.6 ppm : u : 4H |
| | 3.8 ppm : AB system : 2H |
| | 4.35 ppm : s : 2H |
| | 5.45 ppm : bs : 1H |
| | 7.1 to 7.8 ppm : u : 3H |
| | 8.0 to 8.5 ppm : u : 3H |
| | 8.9 ppm : bs : 1H |

C) 3-[3,5-Bis(trifluoromethyl)benzyl]-5-(3,4-dichlorophenyl)-5-[2-(methanesulfonyloxy)ethyl] tetrahydro-2H-1,3-oxazin-2-one A solution of 3 g of the compound obtained in the previous step and 0.7 g of triethylamine in 50 ml of DCM is cooled to +5° C., a solution of 0.66 g of methanesulfonyl chloride in 6 ml of DCM is added dropwise and the reaction mixture is stirred while the temperature is allowed to rise to RT. It is concentrated under vacuum, the residue is taken up with water and extracted with AcOEt, the organic phase is washed with water, with 2N HCl solution, with water, with 5% $NaHCO_3$ solution, with water and with saturated NaCl solution and dried over $MgSO_4$ and the solvent is evaporated off under vacuum to give 3.4 g of the expected product.

D) 3-[3,5-Bis(trifluoromethyl)benzyl]-5-(3,4-dichlorophenyl)-5-[2-(4-phenylpiperid-1-yl)ethyl] tetrahydro-2H-1,3-oxazin-2-one hydrochloride hemihydrate A mixture of 0.32 g of 4-phenylpiperidine, 1 g of the compound obtained in the previous step and 0.28 g of potassium iodide in 5 ml of DMF is heated at 60° C. for 3 hours. After cooling, the reaction mixture is poured into water and extracted with AcOEt, the organic phase is washed with water and with saturated NaCl solution and dried over $MgSO_4$ and the solvent is evaporated off under vacuum. The residue is chromatographed on silica H using DCM and then a DCM/MeOH mixture (98/2; v/v) as the eluent. The product obtained is taken up with a saturated solution of gaseous HCl in ether and the precipitate formed is wrung to give 0.22 g of the expected product. M.p.=174° C.

EXAMPLE 5

5-[2-(4-Benzylpiperid-1-yl)ethyl]-3-[3,5-bis (trifluoromethyl)benzyl]-5-(3,4-dichlorophenyl) tetrahydro-2H-1,3-oxazin-2-one hydrochloride 1.5 hydrate This compound is prepared by the procedure described in step D of EXAMPLE 4 from 0.3 g of 4-benzylpiperidine, 0.8 g of the compound obtained in step C of EXAMPLE 4, 0.24 g of potassium iodide and 5 ml of DMF. The residue is chromatographed on silica H using DCM and then a DCM/MeOH mixture (96/4; v/v) as the eluent. The product obtained is taken up with a saturated solution of gaseous HCl in ether and the precipitate formed is wrung to give 0.13 g of the expected product. M.p.=124° C.

EXAMPLE 6

5-[2-(4-Anilinopiperid-1-yl)ethyl]-3-[3,5-bis (trifluoromethyl)benzyl]-5-(3,4-dichlorophenyl) tetrahydro-2H-1,3-oxazin-2-one dihydrochloride monohydrate A mixture of 0.3 g of 4-anilinopiperidine, 0.8 g of the compound obtained in step C of EXAMPLE 4 and 0.69 g of potassium carbonate in 5 ml of acetonitrile is heated at 5°–60° C. for 5 hours. The reaction mixture is poured into water and extracted with AcOEt, the organic phase is washed twice with water and with saturated NaCl solution and dried over $MgSO_4$ and the solvent is evaporated off under vacuum. The residue is chromatographed on silica H using DCM and then a DCM/MeOH mixture (96/4; v/v) as the eluent. The product obtained is taken up with a saturated solution of gaseous HCl in ether and the precipitate formed is wrung to give 0.12 g of the expected product. M.p.=158° C.

EXAMPLE 7

5-(3,4-Dichlorophenyl)-5-[2-[4-phenyl-1-azoniabicyclo [2.2.2]oct-1-yl]ethyl]-3-[3,5-bis(trifluoromethyl)benzyl] tetrahydro-2H-1,3-oxazin-2-one chloride 2.5 hydrate A mixture of 0.53 g of 4-phenyl-1-azabicyclo[2.2.2] octane and 1.4 g of the compound obtained in step C of EXAMPLE 4 in 5 ml of DMF is heated at 60° C. for 5 hours. After cooling to RT, the reaction mixture is poured into water and extracted with DCM, the organic phase is washed twice with 2N HCl solution and three times with saturated NaCl solution and dried over $MgSO_4$ and the solvent is evaporated off under vacuum. The residue is chromatographed on silica using DCM and then a DCM/MeOH mixture (92/8; v/v) as the eluent. The product obtained is taken up with ether and the precipitate formed is wrung to give 0.21 g of the expected product. M.p.=138° C.

EXAMPLE 8

3-Benzyl-5-[3-(4-benzylpiperid-1-yl)propyl]-5-(3,4-dichlorophenyl)tetrahydro-2H-1,3-oxazin-2-one hydrochloride A) 3-Benzyl-5-(3,4-dichlorophenyl)-5-[3-(tetrahydropyran-2-yloxy)propyl]tetrahydro-2H-1,3-oxazin-2-one A solution of 12.5 g of the compound obtained in Preparation 1.2 in 150 ml of THF is cooled to +5° C., 4.13 g of potassium tert-butylate are added and a solution of 5.78 g of benzyl bromide in 30 ml of THF is then added dropwise. The mixture is stirred for 1 hour at RT and concentrated under vacuum. The residue is taken up with water and extracted with AcOEt, the organic phase is washed twice with water and with saturated NaCl solution and dried over $MgSO_4$ and the solvent is evaporated off under vacuum to give the expected product, which is used as such.

B) 3-Benzyl-5-(3,4-dichlorophenyl)-5-(3-hydroxypropyl) tetrahydro-2H-1,3-oxazin-2-one The compound obtained in the previous step is taken up with a saturated solution of gaseous HCl in MeOH and the reaction mixture is stirred for 2 hours at RT. It is concentrated under vacuum, the residue is taken up twice with a saturated solution of gaseous HCl in MeOH and the solvent is evaporated off under vacuum. The residue is chromatographed on silica using DCM and then a DCM/MeOH mixture (96/4; v/v) as the eluent to give 10.6 g of the expected product, which is used as such.

C) 3-Benzyl-5-(3,4-dichlorophenyl)-5-[3-(methanesulfonyloxy)propyl]tetrahydro-2H-1,3-oxazin-2-one A solution of 10 g of the compound obtained in the previous step and 3.07 g of triethylamine in 350 ml of DCM is cooled to +5° C. and a solution of 3.19 g of methanesulfonyl chloride in 35 ml of DCM is added dropwise. After the addition, the reaction mixture is concentrated under vacuum, the residue is taken up with water and extracted with AcOEt, the organic phase is washed twice with water and with saturated NaCl solution and dried over $MgSO_4$ and the solvent is evaporated off under vacuum to give 11 g of the expected product, which is used as such.

D) 3-Benzyl-5-[3-(4-benzylpiperid-1-yl)propyl]-5-(3,4-dichlorophenyl)tetrahydro-2H-1,3-oxazin-2-one hydrochloride A mixture of 1.86 g of 4-benzylpiperidine, 2 g of the compound obtained in the previous step and 0.7 g of potassium iodide in 10 ml of DMF is heated at 50° C. for 2 hours. After cooling to RT, the reaction mixture is poured into water and extracted with AcOEt, the organic phase is washed twice with water and with saturated NaCl solution and dried over $MgSO_4$ and the solvent is evaporated off under vacuum. The residue is chromatographed on silica H using DCM and then a DCM/MeOH mixture (98/2; v/v) as the eluent. The product obtained is taken up with a saturated solution of gaseous HCl in ether and the solvent is evaporated off under vacuum to give 1.4 g of the expected product after crystallization from AcOEt. M.p.=219° C.

EXAMPLE 9

3-Benzyl-5-(3,4-dichlorophenyl)-5-[3-(4-hydroxy-4-phenylpiperid-1-yl)propyl]tetrahydro-2H-1,3-oxazin-2-one hydrochloride hemihydrate This compound is prepared by the procedure described in step D of EXAMPLE 8 from 1.6 g of 4-hydroxy-4-phenylpiperidine, 2 g of the compound obtained in step C of EXAMPLE 8 and 0.75 g of potassium iodide in 10 ml of DMF. The residue is chromatographed on silica H using DCM and then a DCM/MeOH mixture (96/4; v/v) as the eluent. The product obtained is taken up with a saturated solution of gaseous HCl in ether and the precipitate formed is wrung to give 1.34 g of the expected product. M.p=125° C.

EXAMPLE 10

5-[3-(4-Acetamido-4-phenylpiperid-1-yl)propyl]-3-benzyl-5-(3,4-dichlorophenyl)tetrahydro-2H-1,3-oxazin-2-one hydrochloride 1.5 hydrate 2.02 g of 4-acetamido-4-phenylpiperidine hydrochloride are dissolved in 5 ml of water, rendered alkaline to pH 13 by the addition of concentrated NaOH and extracted with DCM, the organic phase is dried over $MgSO_4$ and the solvent is evaporated off under vacuum. The residue is taken up with 10 ml of DMF, 1.5 g of the compound obtained in step C of EXAMPLE 8 and 0.53 g of potassium iodide are added and the reaction mixture is heated at 50° C. for 2 hours 30 minutes. It is poured into water and extracted with AcOEt, the organic phase is washed three times with water and with saturated NaCl solution and dried over $MgSO_4$ and the solvent is evaporated off under vacuum. The residue is chromatographed on silica using DCM and then a DCM/MeOH mixture (96/4; v/v) as the eluent. The product obtained is taken up with a saturated solution of gaseous HCl in ether and the solvent is evaporated off under vacuum to give 1.34 g of the expected product after crystallization from AcOEt. M.p.=145° C.

EXAMPLE 11

3-Benzyl-5-(3,4-dichlorophenyl)-5-[3-[4-(N-phenylacetamido)piperid-1-yl]propyl]tetrahydro-2H-1,3-oxazin-2-one hydrochloride A mixture of 1.76 g of 4-anilinopiperidine, 2 g of the compound obtained in step C of EXAMPLE 8 and 0.75 g of potassium iodide in 10 ml of DMF is heated at 50° C. for 1 hour 30 minutes. The reaction mixture is poured into water and extracted with AcOEt, the organic phase is washed three times with water and with saturated NaCl solution and dried over $MgSO_4$ and the solvent is evaporated off under vacuum. The residue is chromatographed on silica H using DCM and then a DCM/MeOH mixture (96/4; v/v) as the eluent. The product obtained is taken up with 10 ml of acetic anhydride and the reaction mixture is stirred for 48 hours at RT. It is concentrated under vacuum, the residue is extracted with AcOEt, the organic phase is washed twice with 20% aqueous ammonia solution, twice with water and with saturated NaCl solution and dried over $MgSO_4$ and the solvent is evaporated off under vacuum. The product obtained is taken up with a saturated solution of gaseous HCl in ether and the solvent is evaporated off under vacuum to give 1.4 g of the expected product after crystallization from AcOEt. M.p.=195° C.

EXAMPLE 12

3-Benzyl-5-(3,4-dichlorophenyl)-5-[3-[4-phenyl-1-azoniabicyclo[2.2.2]oct-1-yl]propyl]tetrahydro-2H-1,3-oxazin-2-one chloride hemihydrate A mixture of 1.2 g of 4-phenyl-1-azabicyclo[2.2.2]octane and 2 g of the compound obtained in step C of EXAMPLE 8 in 10 ml of DMF is heated at 50° C. for 3 hours. After cooling to RT, the reaction mixture is poured into water and extracted with DCM, the organic phase is washed with water, with saturated NaCl solution, twice with 2N HCl solution, twice with water and with saturated NaCl solution and dried over $MgSO_4$ and the solvent is evaporated off under vacuum. The residue is taken up with AcOEt and the precipitate formed is wrung to give 1.56 g of the expected product.

M.p.=235° C.

EXAMPLE 13

3-Benzyl-5-(3,4-dichlorophenyl)-5-[3-(4-benzyl-pyridinio-1)propyl]tetrahydro-2H-1,3-oxazin-2-one chloride dihydrate A mixture of 1.07 g of 4-benzylpyridine and 2 g of the compound obtained in step C of EXAMPLE 8 in 10 ml of DMF is heated at 90° C. for 6 hours. After cooling to RT, the reaction mixture is poured into water and extracted with DCM, the organic phase is washed with water and three times with saturated NaCl solution and dried over $MgSO_4$ and the solvent is evaporated off under vacuum. The residue is chromatographed on silica using DCM and then a DCM/MeOH mixture (90/10; v/v) as the eluent. The product obtained is dissolved in the minimum amount of acetone, ether is added until precipitation occurs, and the precipitate formed is wrung to give 0.8 g of the expected product. M.p.=84° C.

EXAMPLE 14

4-Benzyl-6-(3,4-dichlorophenyl)-6-[2-(4-hydroxy-4-phenylpiperid-1-yl)ethyl]morpholin-3-one hydrochloride hemihydrate A) 4-Benzyl-6-(3,4-dichlorophenyl)-6-(2-hydroxyethyl) morpholin-3-one 0.51 g of potassium tert-butylate is added at RT to a solution of 1.7 g of the compound obtained in Preparation 1.3 in 30 ml of THF, 0.77 g of benzyl bromide is then added slowly and the reaction mixture is heated for 2 hours at 50° C. It is concentrated under vacuum, the residue is taken up with water and extracted with ether, the organic phase is washed with water and dried over $Na_2SO_4$ and the solvent is evaporated off under vacuum. The residue is chromatographed on silica H using a DCM/MeOH mixture (100/0.5; v/v) as the eluent. The product obtained (1 g) is dissolved in 10 ml of MeOH and acidified to pH 1 by the addition of a saturated solution of gaseous HCl in ether and the solvents are evaporated off under vacuum. The residue is extracted with ether, the organic phase is washed with water and dried over $Na_2SO_4$ and the solvent is evaporated off under vacuum to give 0.65 g of the expected product.

Proton NMR spectrum at 200 MHz in DMSO-$d_6$

| | |
|---|---|
| δ: | 1.9 ppm : mt : 2H |
| | 2.7 to 3.3 ppm : mt : 2H |
| | 3.65 ppm : AB system : 2H |
| | 4.0 ppm : AB system : 2H |
| | 4.3 ppm : t : 1H |
| | 4.45 ppm : AB system : 2H |
| | 7.0 to 7.6 : u : 11H |

This compound can also be obtained using the method described below.

A') 4-Benzyl-6-(3,4-dichlorophenyl)-6-(2-hydroxyethyl) morpholin-3-one

A mixture of 6 g of the compound obtained in Preparation 1.4 and 1.87 g of potassium tert-butylate in 100 ml of THF is stirred for two hours at RT, 2.85 g of benzyl bromide are then added slowly and the reaction mixture is refluxed for 3 hours. It is concentrated under vacuum, the residue is taken up with a buffer solution of pH 2 and extracted with ether, the organic phase is washed with water and dried over $Na_2SO_4$ and the solvent is evaporated off under vacuum. The product obtained is dissolved in MeOH, 1.3 g of lithium hydroxide monohydrate are added and the reaction mixture is stirred for 30 minutes at RT. It is concentrated under vacuum, the residue is extracted with ether, the organic phase is washed with water and dried over $Na_2SO_4$ and the solvent is evaporated off under vacuum. The residue is chromatographed on silica H using a DCM/MeOH mixture (100/1; v/v) as the eluent to give 4.6 g of the expected product.

B) 4-Benzyl-6-(3,4-dichlorophenyl)-6-[2-(methanesulfonyloxy)ethyl]morpholin-3-one A solution of 0.65 g of the compound obtained in the previous step and 0.34 g of triethylamine in 30 ml of DCM is cooled to 0° C. and 0.25 g of methanesulfonyl chloride is added. After the addition, the reaction mixture is concentrated under vacuum, the residue is extracted with AcOEt, the organic phase is washed with water and dried over $Na_2SO_4$ and the solvent is evaporated off under vacuum to give 0.71 g of the expected product, which is used as such.

C) 4-Benzyl-6-(3,4-dichlorophenyl)-6-[2-(4-hydroxy-4-phenylpiperid-1-yl)ethyl]morpholin-3-one hydrochloride hemihydrate A mixture of 0.7 g of the compound obtained in the previous step, 0.378 g of 4-hydroxy-4-phenylpiperidine and 0.8 g of $K_2CO_3$ in 5 ml of acetonitrile is refluxed for 4 hours. After cooling to RT, the reaction mixture is poured into water and extracted with AcOEt, the organic phase is washed with water and dried over $Na_2SO_4$ and the solvent is evaporated off under vacuum. The residue is chromatographed on silica H using a DCM/MeOH mixture (100/3; v/v) as the eluent. The product obtained is dissolved in the minimum amount of DCM and acidified to pH 1 by the addition of a saturated solution of gaseous HCl in ether and the precipitate formed is wrung to give 0.43 g of the expected product. M.p.=160°–162° C.

EXAMPLE 15

6-(3,4-Dichlorophenyl)-6-[2-(4-hydroxy-4-phenylpiperid-1-yl)ethyl]-4-(4-phenylbenzyl) morpholin-3-one hydrochloride monohydrate A) 6-[2-(Benzoyloxy)ethyl]-6-(3,4-dichlorophenyl)-4-(4-phenylbenzyl)morpholin-3-one A mixture of 1.3 g of the compound obtained in Preparation 1.4 and 0.36 g of potassium tert-butylate in 30 ml of THF is stirred for 30 minutes at RT, 0.79 g of 4-(bromomethyl)biphenyl is added and the reaction mixture is refluxed for 2 hours. It is concentrated under vacuum, the residue is extracted with ether, the organic phase is washed with water and dried over $Na_2SO_4$ and the solvent is evaporated off under vacuum. The residue is chromatographed on silica H using DCM and then a DCM/MeOH mixture (100/0.5; v/v) as the eluent to give 1.1 g of the expected product.

Proton NMR spectrum at 200 MHz in DMSO-$d_6$

| | |
|---|---|
| δ: | 2.3 ppm : mt : 2H |
| | 3.55 ppm : AB system : 2H |
| | 3.9 to 4.4 ppm : u : 4H |
| | 4.5 ppm : s : 2H |
| | 7.0 to 7.8 ppm : u : 17H |

B) 6-(3,4-Dichlorophenyl)-6-(2-hydroxyethyl)-4-(4-phenylbenzyl)morpholin-3-one

A mixture of 1.1 g of the compound obtained in the previous step and 2 ml of concentrated NaOH solution in 20 ml of MeOH is stirred for 30 minutes at RT. The reaction mixture is concentrated under vacuum, the residue is extracted with ether, the organic phase is washed with water and dried over $Na_2SO_4$ and the solvent is evaporated off under vacuum to give 0.84 g of the expected product.

Proton NMR spectrum at 200 MHz in DMSO-$d_6$

| | |
|---|---|
| δ: | 1.85 ppm : mt : 2H |
| | 2.7 to 3.3 ppm : mt : 2H |
| | 3.5 ppm : AB system : 2H |
| | 3.95 ppm : AB system : 2H |
| | 4.35 ppm : t : 1H |
| | 4.4 ppm : AB system : 2H |
| | 7.0 to 7.6 ppm : u : 12H |

C) 6-(3,4-Dichlorophenyl)-6-[2-(methanesulfonyloxy)ethyl]-4-(4-phenylbenzyl)morpholin-3-one 0.252 g of methanesulfonyl chloride is added at RT to a solution of 0.84 g of the compound obtained in the previous step and 0.223 g of triethylamine in 30 ml of DCM and the mixture is stirred for 30 minutes at RT. It is concentrated under vacuum, the residue is extracted with ether, the organic phase is washed with water and dried over $Na_2SO_4$ and the solvent is evaporated off under vacuum to give 0.89 g of the expected product, which is used as such.

D) 6-(3,4-Dichlorophenyl)-6-[2-(4-hydroxy-4-phenylpiperid-1-yl)ethyl]-4-(4-phenylbenzyl)morpholin-3-one hydrochloride monohydrate A mixture of 0.89 g of the compound obtained in the previous step, 0.875 g of 4-hydroxy-4-phenylpiperidine p-toluenesulfonate and 0.483 g of $K_2CO_3$ in 2 ml of DMF is heated at 80°–100° C. for 1 hour. After cooling to RT, the reaction mixture is poured into water and extracted with ether, the organic phase is washed with water and dried over $Na_2SO_4$ and the solvent is evaporated off under vacuum. The residue is chromatographed on silica H using a gradient of a DCM/MeOH mixture (from 100/2; v/v to 100/5; v/v) as the eluent. The product obtained is dissolved in the minimum amount of DCM and acidified to pH 1 by the addition of a saturated solution of gaseous HCl in ether and the precipitate formed is wrung to give 0.45 g of the expected product. M.p.=143°–150° C.

EXAMPLE 16

6-(3,4-Dichlorophenyl)-6-[2-[4-phenyl-1-azoniabicyclo[2.2.2]oct-1-yl]ethyl]-4-[3,5-bis(trifluoromethyl)benzyl]morpholin-3-one chloride monohydrate A) 6-[2-(Benzoyloxy)ethyl]-6-(3,4-dichlorophenyl)-4-[3,5-bis(trifluoromethyl)benzyl]morpholin-3-one A mixture of 2.1 g of the compound obtained in Preparation 1.4 and 0.616 g of potassium tert-butylate in 50 ml of THF is stirred for 30 minutes at RT, 1.44 g of 3,5-bis(trifluoromethyl)benzyl chloride are added and the reaction mixture is refluxed for 1 hour. It is concentrated under vacuum, the residue is taken up with a buffer solution of pH 4 and extracted with ether, the organic phase is washed with water and dried over $Na_2SO_4$ and the solvent is evaporated off under vacuum. The residue is chromatographed on silica H using a DCM/ MeOH mixture (100/0.5; v/v) as the eluent to give 1.8 g of the expected product.

Proton NMR spectrum at 200 MHz in DMSO-$d_6$

| | |
|---|---|
| δ: | 2.4 ppm : mt : 2H |
| | 4.05 ppm : AB system : 2H |
| | 4.15 to 4.6 ppm : u : 4H |
| | 4.75 ppm : AB system : 2H |
| | 7.3 to 8.2 ppm : u : 11H |

B) 6-(3,4-Dichlorophenyl)-6-(2-hydroxyethyl)-4-[3,5-bis(trifluoromethyl)benzyl]morpholin-3-one A mixture of 1.8 g of the compound obtained in the previous step and 4 ml of concentrated NaOH solution in 30 ml of MeOH is stirred for 30 minutes at 0° C. and stirring is then continued for 1 hour at RT. The reaction mixture is concentrated under vacuum, the residue is extracted with ether, the organic phase is washed with water and dried over $Na_2SO_4$ and the solvent is evaporated off under vacuum to give 1.1 g of the expected product.

Proton NMR spectrum at 200 MHz in DMSO-$d_6$

| | |
|---|---|
| δ: | 2.0 ppm : t : 2H |
| | 2.9 to 3.45 ppm : mt : 2H |
| | 3.9 ppm : AB system : 2H |
| | 4.2 ppm : AB system : 2H |
| | 4.45 ppm : t : 1H |
| | 4.7 ppm : AB system : 2H |
| | 7.1 to 8.2 ppm : u : 6H |

C) 6-(3,4-Dichlorophenyl)-6-[2-(methanesulfonyloxy)ethyl]-4-[3,5-bis(trifluoromethyl)benzyl]morpholin-3-one 0.25 g of methanesulfonyl chloride is added at RT to a solution of 1.1 g of the compound obtained in the previous step and 0.22 g of triethylamine in 30 ml of DCM and the reaction mixture is stirred for 1 hour. It is concentrated under vacuum, the residue is extracted with AcOEt, the organic phase is washed with water and dried over $Na_2SO_4$ and the solvent is evaporated off under vacuum to give 1.2 g of the expected product, which is used as such.

D) 6-(3,4-Dichlorophenyl)-6-[2-[4-phenyl-1-azoniabicyclo[2.2.2]oct-1-yl]ethyl]-4-[3,5-bis(trifluoromethyl)benzyl]morpholin-3-one chloride monohydrate A mixture of 1.2 g of the compound obtained in the previous step and 0.45 g of 4-phenyl-1-azabicyclo[2.2.2]octane in 4 ml of DMF is heated at 100° C. for 1 hour. After cooling to RT, the reaction mixture is poured into water and extracted with DCM, the organic phase is washed with 2N HCl solution, with saturated NaCl solution and with water and dried over $Na_2SO_4$ and the solvent is evaporated off under vacuum to give 0.9 g of the expected product after crystallization from a DCM/iso ether/pentane mixture. M.p.=160° C.

EXAMPLE 17

2-[2-(4-Acetamido-4-phenylpiperid-1-yl)ethyl]-4-benzoyl-2-(3,4-dichlorophenyl)morpholine hydrochloride monohydrate A) 4-Benzoyl-2-(3,4-dichlorophenyl)-2-(2-hydroxyethyl)morpholine A solution of 3.6 g of the compound obtained in Preparation 1.5 and 2.9 g of triethylamine in 50 ml of DCM is cooled to −60° C., a solution of 1.83 g of benzoyl chloride in 20 ml of DCM is added dropwise and the reaction mixture is stirred for 30 minutes. It is concentrated under vacuum, the residue is extracted with ether, the organic phase is washed with water and with 10% NaOH solution and dried over $Na_2SO_4$ and the solvent is evaporated off under vacuum. The residue is chromatographed on silica H using a gradient of a DCM/MeOH mixture (from 100/1; v/v to 100/5; v/v) as the eluent to give 1.2 g of the expected product.

Proton NMR spectrum at 200 MHz in DMSO-$d_6$

| | |
|---|---|
| δ: | 1.95 ppm : mt : 2H |
| | 2.8 to 4.8 ppm : u : 9H |
| | 6.8 to 7.9 ppm : u : 8H |

B) 4-Benzoyl-2-(3,4-dichlorophenyl)-2-[2-(methanesulfonyloxy)ethyl]morpholine

A solution of 1.2 g of the compound obtained in the previous step and 0.637 g of triethylamine in 50 ml of DCM is heated to 60° C., a solution of 0.414 g of methanesulfonyl chloride in 10 ml of DCM is added dropwise and the reaction mixture is stirred for 1 hour at 60° C. It is concentrated under vacuum, the residue is extracted with an AcOEt/ether mixture (50/50; v/v), the organic phase is washed with water and with saturated $NaHCO_3$ solution and dried over $Na_2SO_4$ and the solvent is evaporated off under vacuum to give 1 g of the expected product, which is used as such.

C) 2-[2-(4-Acetamido-4-phenylpiperid-1-yl)ethyl]-4-benzoyl-2-(3,4-dichlorophenyl)morpholine hydrochloride monohydrate A mixture of 1 g of the compound obtained in the previous step, 1 g of 4-acetamido-4-phenylpiperidine p-toluenesulfonate and 1 g of $K_2CO_3$ in 10 ml of acetonitrile and 5 ml of DMF is refluxed for 4 hours. The reaction mixture is concentrated under vacuum, the residue is extracted with AcOEt, the organic phase is washed with water and dried over $Na_2SO_4$ and the solvent is evaporated off under vacuum. The residue is chromatographed on silica H using a DCM/MeOH mixture (100/3; v/v) as the eluent. The product obtained is dissolved in the minimum amount of DCM and acidified to pH 1 by the addition of a saturated solution of gaseous HCl in ether and the precipitate formed is wrung to give 0.4 g of the expected product. M.p.=184°–187° C.

EXAMPLE 18

2-(3,4-Dichlorophenyl)-4-[(3-isopropoxyphenyl)acetyl]-2-[2-[4-phenyl-1-azoniabicyclo[2.2.2]oct-1-yl]ethyl]morpholine chloride monohydrate A) 2-(3,4-Dichlorophenyl)-2-(2-hydroxyethyl)-4-[(3-isopropoxyphenyl)acetyl]morpholine A solution of 1.2 g of the compound obtained in Preparation 1.5, 0.83 g of 3-isopropoxyphenylacetic acid and 0.86 g of triethylamine in 15 ml of DCM is cooled to 0° C., 2 g of BOP are added and the reaction mixture is stirred for 30 minutes. It is concentrated under vacuum, the residue is extracted with DCM, the organic phase is washed with water, with a buffer solution of pH 2 and with water and dried over $Na_2SO_4$ and the solvent is evaporated off under vacuum. The residue is chromatographed on silica H using a gradient of a DCM/MeOH mixture (from 100/0.5; v/v to 100/2; v/v) as the eluent to give 0.25 g of the expected product.

Proton NMR spectrum at 200 MHz in DMSO-$d_6$

| | |
|---|---|
| δ: | 1.2 ppm : d : 6H |
| | 1.8 ppm : t : 2H |
| | 2.8 to 4.8 ppm : u : 11H |
| | 6.4 to 7.8 ppm : u : 7H |

B) 2-(3,4-Dichlorophenyl)-4-[(3-isopropoxyphenyl)acetyl]-2-[2-(methanesulfonyloxy)ethyl]morpholine 0.069 g of methanesulfonyl chloride is added at RT to a solution of 0.25 g of the compound obtained in the previous step and 0.061 g of triethylamine in 10 ml of DCM and the reaction mixture is stirred for 30 minutes. It is concentrated under vacuum, the residue is extracted with AcOEt, the organic phase is washed with water and with saturated NaCl solution and dried over $Na_2SO_4$ and the solvent is evaporated off under vacuum to give 0.285 g of the expected product, which is used as such.

C) 2-(3,4-Dichlorophenyl)-4-[(3-isopropoxyphenyl)acetyl]-2-[2-[4-phenyl-1-azoniabicyclo[2.2.2]oct-1-yl]ethyl]morpholine chloride monohydrate A mixture of 0.28 g of the compound obtained in the previous step and 0.15 g of 4-phenyl-1-azabicyclo[2.2.2]octane in 2 ml of DMF is heated at 100° C. for 1 hour. The reaction mixture is concentrated under vacuum, the residue is extracted with DCM, the organic phase is washed with water, with 10% HCl solution and with saturated NaCl solution and dried over $Na_2SO_4$ and the solvent is evaporated off under vacuum to give 0.17 g of the expected product after crystallization from an acetone/ether mixture. M.p.=125°–130° C.

EXAMPLE 19

2-[3-(4-Acetamido-4-phenylpiperid-1-yl)propyl]-4-benzoyl-2-(3,4-dichlorophenyl)morpholine hydrochloride monohydrate A) 4-Benzoyl-2-(3,4-dichlorophenyl)-2-(3-hydroxypropyl)morpholine A solution of 2 g of the compound obtained in Preparation 1.6 and 0.83 g of triethylamine in 30 ml of DCM is cooled to −10° C., a solution of 0.97 g of benzoyl chloride in 10 ml of DCM is added dropwise and the reaction mixture is stirred for 30 minutes. It is concentrated under vacuum, the residue is extracted with AcOEt, the organic phase is washed with water and with 10% NaOH solution and dried over $Na_2SO_4$ and the solvent is evaporated off under vacuum. The residue is chromatographed on silica H using a DCM/MeOH mixture (100/1; v/v) as the eluent to give 1.7 g of the expected product.

Proton NMR spectrum at 200 MHz in DMSO-$d_6$

| | |
|---|---|
| δ: | 1.9 to 2.2 ppm : u : 4H |
| | 3.1 to 4.6 ppm : u : 9H |
| | 7.0 to 7.9 ppm : u : 8H |

B) 4-Benzoyl-2-(3,4-dichlorophenyl)-2-[3-(methanesulfonyloxy)propyl]morpholine

A solution of 1.7 g of the compound obtained in the previous step and 0.52 g of triethylamine in 30 ml of DCM is cooled to 0° C., 0.6 g of methanesulfonyl chloride is added and the mixture is stirred for 30 minutes. It is concentrated under vacuum, the residue is extracted with AcOEt, the organic phase is washed with water and dried over $Na_2SO_4$ and the solvent is evaporated off under vacuum to give 1.7 g of the expected product, which is used as such.

C) 2-[3-(4-Acetamido-4-phenylpiperid-1-yl)propyl]-4-benzoyl-2-(3,4-dichlorophenyl)morpholine hydrochloride monohydrate A mixture of 1.7 g of the compound obtained in the previous step, 2.18 g of 4-acetamido-4-phenylpiperidine p-toluenesulfonate and 2.5 g of $K_2CO_3$ in 10 ml of DMF and 10 ml of acetonitrile is refluxed for 3 hours. The reaction mixture is concentrated under vacuum, the residue is taken up with water and extracted with ether, the organic phase is washed with water and dried over $Na_2SO_4$ and the solvent is evaporated off under vacuum. The residue is chromatographed on silica H using a DCM/MeOH mixture (100/3; v/v) as the eluent. The product obtained is dissolved in the minimum amount of DCM, a saturated solution of gaseous HCl in ether is added until the pH is 1, and the precipitate formed is wrung to give 1 g of the expected product.

M.p.=170°–173° C.

EXAMPLE 20

3-Benzyl-5-(3,4-dichlorophenyl)-5-[2-(4-hydroxy-4-phenylpiperid-1-yl)ethyl]oxazolidin-2-one hydrochloride A) 5-[2-(Benzoyloxy)ethyl]-3-benzyl-5-(3,4-dichlorophenyl)oxazolidin-2-one 0.44 g of potassium tert-butylate is added at RT to a solution of 1.5 g of the compound obtained in Preparation 1.7 in 30 ml of THF and the mixture is stirred for 1 hour at RT. 0.667 g of benzyl bromide is then added dropwise and the reaction mixture is refluxed for 3 hours. It is concentrated under vacuum, the residue is extracted with ether, the organic phase is washed with a buffer solution of pH 2 and with water and dried over $Na_2SO_4$ and the solvent is evaporated off under vacuum. The residue is chromatographed on silica H using DCM and then a DCM/MeOH mixture (99.5/0.5; v/v) as the eluent to give 0.9 g of the expected product.

Proton NMR spectrum at 200 MHz in DMSO-$d_6$

| | |
|---|---|
| δ: | 2.6 ppm : mt : 2H |
| | 3.5 to 4.0 ppm : AB system : 2H |
| | 4.2 to 4.7 ppm : u : 4H |
| | 7.2 to 8.0 ppm : u : 13H |

B) 3-Benzyl-5-(3,4-dichlorophenyl)-5-(2-hydroxyethyl)oxazolidin-2-one

A mixture of 0.9 g of the compound obtained in the previous step and 0.5 ml of concentrated NaOH solution in 30 ml of MeOH and 15 ml of DCM is stirred for 30 minutes at RT. The reaction mixture is concentrated under vacuum, the residue is extracted with ether, the organic phase is washed with water and dried over $Na_2SO_4$ and the solvent is evaporated off under vacuum to give 0.7 g of the expected product, which is used as such.

C) 3-Benzyl-5-(3,4-dichlorophenyl)-5-[2-(methanesulfonyloxy)ethyl]oxazolidin-2-one 0.24 g of methanesulfonyl chloride is added at RT to a solution of 0.7 g of the compound obtained in the previous step and 0.21 g of triethylamine in 20 ml of DCM and the reaction mixture is stirred for 1 hour at RT. It is concentrated under vacuum, the residue is extracted with AcOEt, the organic phase is washed with water and dried over $Na_2SO_4$ and the solvent is evaporated off under vacuum to give 0.76 g of the expected product, which is used as such.

D) 3-Benzyl-5-(3,4-dichlorophenyl)-5-[2-(4-hydroxy-4-phenylpiperid-1-yl)ethyl]oxazolidin-2-one hydrochloride A mixture of 0.76 g of 4-hydroxy-4-phenylpiperidine and 0.282 g of potassium iodide in 2 ml of DMF is heated at 50°–60° C. for 3 hours. After cooling to RT, the reaction mixture is poured into water and extracted with AcOEt, the organic phase is washed with water and dried over $Na_2SO_4$ and the solvent is evaporated off under vacuum. The residue is chromatographed on silica H using a gradient of a DCM/MeOH mixture (from 100/2; v/v to 100/3; v/v) as the eluent. The product obtained is dissolved in the minimum amount of DCM and acidified to pH 1 by the addition of a saturated solution of gaseous HCl in ether and the precipitate formed is wrung to give 0.36 g of the expected product. M.p.=223°–225° C.

EXAMPLE 21

5-(3,4-Dichlorophenyl)-5-[2-[4-phenyl-1-azoniabicyclo[2.2.2]oct-1-yl]ethyl]-3-[3,5-bis(trifluoromethyl)benzyl]oxazolidin-2-one chloride dihydrate A) 5-(3,4-Dichlorophenyl)-5-(2-hydroxyethyl)-3-[3,5-bis(trifluoromethyl)benzyl]oxazolidin-2-one A mixture of 1.4 g of the compound obtained in Preparation 1.7 and 0.45 g of potassium tert-butylate in 30 ml of THF is stirred for 30 minutes at RT, 1.05 g of 3,5-bis(trifluoromethyl)benzyl chloride are added and the mixture is refluxed for 5 hours. It is concentrated under vacuum, the residue is extracted with ether, the organic phase is washed with water and dried over $MgSO_4$ and the solvent is evaporated off under vacuum. The product obtained is taken up with 30 ml of MeOH, 0.18 g of lithium hydroxide monohydrate and 1 ml of water are added and the mixture is stirred for 2 hours at RT. It is concentrated under vacuum, the residue is extracted with ether, the organic phase is washed with water and dried over $MgSO_4$ and the solvent is evaporated off under vacuum. The residue is chromatographed on silica H using a DCM/MeOH mixture (100/0.5; v/v) as the eluent to give 0.96 g of the expected product.

Proton NMR spectrum at 200 MHz in DMSO-$d_6$

| | |
|---|---|
| δ: | 2.2 ppm : mt : 2H |
| | 3.0 to 3.55 ppm : mt : 2H |
| | 3.57 to 3.9 ppm : AB system : 2H |
| | 4.35 to 4.7 ppm : u : 3H |
| | 7.2 to 8.1 ppm : u : 6H |

B) 5-(3,4-Dichlorophenyl)-5-[2-(methanesulfonyloxy)ethyl]-3-[3,5-bis(trifluoromethyl)benzyl]oxazolidin-2-one 0.24 g of methanesulfonyl chloride is added at RT to a solution of 0.95 g of the compound obtained in the previous step and 0.21 g of triethylamine in 20 ml of DCM and the reaction mixture is stirred for 1 hour at RT. It is concentrated under vacuum, the residue is extracted with AcOEt, the organic phase is washed with water and dried over $Na_2SO_4$ and the solvent is evaporated off under vacuum to give 1.1 g of the expected product, which is used as such.

C) 5-(3,4-Dichlorophenyl)-5-[2-[4-phenyl-1-azoniabicyclo[2.2.2]oct-1-yl]ethyl]-3-[3,5-bis(trifluoromethyl)benzyl]oxazolidin-2-one chloride dihydrate A mixture of 0.46 g of 4-phenyl-1-azabicyclo[2.2.2]octane and 1.1 g of the compound obtained in the previous step in 2 ml of DMF is heated at 60° C. for 5 hours. After cooling to RT, the reaction mixture is poured into water and extracted with DCM, the organic phase is washed with water, with saturated NaCl solution, with 2N HCl solution and with water and dried over $MgSO_4$ and the solvent is evaporated off under vacuum to give 0.6 g of the expected product after crystallization from a DCM/pentane mixture. M.p.=127°–130° C. (dec.).

EXAMPLE 22

5-[2-(4-Acetamido-4-phenylpiperid-1-yl)ethyl]-1-benzyl-5-(3,4-dichlorophenyl)-4-methylpiperazine-2,3-dione hydrochloride A) 1-Benzyl-5-(3,4-dichlorophenyl)-4-methyl-5-[2-(tetrahydropyran-2-yloxy)ethyl]piperazine-2,3-dione 0.2 g of potassium tert-butylate is added to a solution of 0.6 g of the compound obtained in Preparation 1.8 in 10 ml of THF and the mixture is stirred for 1 hour at RT. 0.21 ml of benzyl bromide is then added and the reaction mixture is heated at 40° C. for 2 hours. It is concentrated under vacuum, the residue is extracted with DCM, the organic phase is washed with water and dried over $MgSO_4$ and the solvent is evaporated off under vacuum to give 0.58 g of the expected product after crystallization from ether. M.p.=178° C.

B) 1-Benzyl-5-(3,4-dichlorophenyl)-5-(2-hydroxyethyl)-4-methylpiperazine-2,3-dione A mixture of 0.56 g of the compound obtained in the previous step, 10 ml of MeOH and 1 ml of a saturated solution of gaseous HCl in ether is stirred for 1 hour. The reaction mixture is concentrated under vacuum, the residue is taken up with iso ether and the precipitate formed is wrung to give 0.45 g of the expected product. M.p.=198° C.

C) 1-Benzyl-5-(3,4-dichlorophenyl)-5-[2-(methanesulfonyloxy)ethyl]-4-methylpiperazine-2,3-dione A solution of 0.44 g of the compound obtained in the previous step and 0.24 ml of triethylamine in 10 ml of DCM is cooled to 0° C., 0.12 ml of methanesulfonyl chloride is added slowly and the reaction mixture is stirred for 15 minutes. It is washed twice with water, the organic phase is dried over $MgSO_4$ and the solvent is evaporated off under vacuum to give 0.5 g of the expected product, which is used as such.

D) 5-[2-(4-Acetamido-4-phenylpiperid-1-yl)ethyl]-1-benzyl-5-(3,4-dichlorophenyl)-4-methylpiperazine-2,3-dione hydrochloride A mixture of 0.5 g of the compound obtained in the previous step, 0.85 g of 4-acetamido-4-phenylpiperidine p-toluenesulfonate and 0.6 g of $K_2CO_3$ in 5 ml of DMF is heated at 80° C. for 8 hours 30 minutes . After cooling to RT, the reaction mixture is poured into water and the precipitate formed is wrung and washed with water. The precipitate is dissolved in DCM, the organic phase is dried over $MgSO_4$ and the solvent is evaporated off under vacuum. The residue is chromatographed on silica H using DCM and then a DCM/MeOH mixture (93/7; v/v) as the eluent. The product obtained is dissolved in DCM, acidified to pH 1 by the addition of a saturated solution of gaseous HCl ether and concentrated under vacuum to give 0.105 g the expected product after crystallization from ether.

M.p.=220° C. (dec.).

EXAMPLE 23

3-[2-(4-Acetamido-4-phenylpiperid-1-yl)ethyl]-1-benzoyl-3-(3,4-dichlorophenyl)-4-methylpiperazine dihydrochloride hemihydrate A) 1-Benzoyl-3-(3,4-dichlorophenyl)-4-methyl-3-[2-(tetrahydropyran-2-yloxy)ethyl]piperazine 0.45 ml of triethylamine is added to a solution of 1 g of the compound obtained in Preparation 1.9 in 15 ml of DCM, the reaction mixture is then cooled to 0° C. and 0.32 ml of benzoyl chloride is added dropwise. The reaction mixture is then washed with water and with 1N NaOH solution, the organic phase is dried over $MgSO_4$ and the solvent is evaporated off under vacuum. The residue is chromatographed on silica using heptane and then a heptane/AcOEt mixture (50/50; v/v) as the eluent to give 0.95 g of the expected product, which is used as such.

B) 1-Benzoyl-3-(3,4-dichlorophenyl)-3-(2-hydroxyethyl)-4-methylpiperazine hydrochloride A saturated solution of gaseous HCl in ether is added to a solution of 0.95 g of the compound obtained in the previous step in 15 ml of MeOH until the pH is 1, and the mixture is left to stand for 2 hours at RT. It is concentrated under vacuum, the residue is taken up with ether and the precipitate formed is wrung and dried to give 0.8 g of the expected compound.

Proton NMR spectrum at 200 MHz in DMSO-$d_6$

| | |
|---|---|
| δ: | 1.1 to 1.9 ppm : u : 2H<br>2.1 to 5.1 ppm : u : 12H<br>7.1 to 8.5 ppm : u : 8H |

C) 3-[2-(4-Acetamido-4-phenylpiperid-1-yl)ethyl]-1-benzoyl-3-(3,4-dichlorophenyl)-4-methylpiperazine dihydrochloride hemihydrate 0.78 ml of triethylamine is added to a solution of 0.8 g of the compound obtained in the previous step in 15 ml of DCM, the mixture is then cooled to –20° C. and 0.25 ml of methanesulfonyl chloride is added dropwise. The reaction mixture is stirred for 10 minutes and then washed with water and with 10% $Na_2CO_4$ solution and the organic phase is dried over $MgSO_4$ and filtered. 1.5 g of 4-acetamido-4-phenylpiperidine p-toluenesulfonate are added to the filtrate and the mixture is concentrated under vacuum. The residue is taken up with 10 ml of DMF, 1.5 g of $K_2CO_3$ are added and the reaction mixture is heated at 80° C. for 2 hours 30 minutes. After cooling, it is poured into iced water and extracted with AcOEt, the organic phase is washed with 1N NaOH solution and with water and dried over $MgSO_4$ and the solvent is evaporated off under vacuum. The residue is chromatographed on silica H using DCM and then a DCM/MeOH mixture (93/7; v/v) as the eluent. The product obtained is taken up with a saturated solution of gaseous HCl in ether and the precipitate formed is wrung to give 0.86 g of the expected product.

M.p.=210° C. (dec.).

EXAMPLE 24

3-(3,4-Dichlorophenyl)-1-[(3-isopropoxyphenyl)acetyl]-4-methyl-3-[2-[4-phenyl-1-azoniabicyclo[2.2.2]oct-1-yl]ethyl]piperazine chloride hydrochloride A) 3-(3,4-Dichlorophenyl)-1-[(3-isopropoxyphenyl)acetyl]-4-methyl-3-[2-(tetrahydropyran-2-yloxy)ethyl]piperazine 0.57 ml of triethylamine and then 0.52 g of 3-isopropoxyphenylacetic acid and 1.3 g of BOP are added to a solution of 1 g of the compound obtained in Preparation 1.9 in 15 ml of DCM. The mixture is stirred for 15 minutes at RT and concentrated under vacuum. The residue is extracted with AcOEt, the organic phase is washed with water, with 1N NaOH solution and with saturated NaCl solution and dried over $MgSO_4$ and the solvent is evaporated off under vacuum. The residue is chromatographed on silica using heptane and then a heptane/AcOEt mixture (50/50; v/v) as the eluent to give 1.1 g of the expected product, which is used as such.

B) 3-(3,4-Dichlorophenyl)-3-(2-hydroxyethyl)-1-[(3-isopropoxyphenyl)acetyl]-4-methylpiperazine hydrochloride A saturated solution of gaseous HCl in ether is added to a solution of 1.1 g of the compound obtained in the previous step in 15 ml of MeOH until the pH is 1, and the reaction mixture is left to stand for 2 hours 30 minutes at RT. It is concentrated under vacuum, the residue is taken up with ether and the precipitate formed is wrung and dried to give 1.05 g of the expected product.

C) 3-(3,4-Dichlorophenyl)-1-[(3-isopropoxyphenyl)acetyl]-4-methyl-3-[2-[4-phenyl-1-azoniabicyclo[2.2.2]oct-1-yl]ethyl]piperazine chloride hydrochloride 0.8 ml of triethylamine is added to a solution of 1.05 g of the compound obtained in the previous step in 15 ml of DCM, the mixture is then cooled to −20° C. and 0.22 ml of methanesulfonyl chloride is added dropwise. After 5 minutes, the reaction mixture is washed with water and with 10% $Na_2CO_3$ solution and the organic phase is dried over $MgSO_4$ and filtered. 1 g of 4-phenylquinuclidine is then added to the filtrate and the mixture is concentrated under vacuum. The residue is taken up with 1 ml of DMF and heated at 80° C. for 1 hour. After cooling to RT, the reaction mixture 1 diluted with DCM and washed twice with 2N HCl solution and with saturated NaCl solution, the organic phase dried over $MgSO_4$ and the solvent is evaporated off under vacuum. The residue is chromatographed on silica H using DCM and then a DCM/MeOH mixture (90/10; v/v) as the eluent. The product obtained is taken up with iso ether and the precipitate formed is wrung to give 1.05 g of the expected product. M.p.=168° C. (dec.).

EXAMPLE 25

6-[2-(4-Acetamido-4-phenylpiperid-1-yl)ethyl]-4-benzyl-6-(3,4-difluorophenyl)morpholin-3-one hydrochloride hemihydrate A) 6-[2-(Benzoyloxy)ethyl]-4-benzyl-6-(3,4-difluorophenyl)morpholin-3-one A mixture of 1.1 g of the compound obtained in Preparation 1.10 and 0.38 g of potassium tert-butylate in 50 ml of THF is stirred for 30 minutes at RT, 0.51 g of benzyl bromide is added and the reaction mixture is refluxed for 2 hours. It is concentrated under vacuum, the residue is extracted with ether, the organic phase is washed with water and with a buffer solution of pH 2 and dried over $Na_2SO_4$ and the solvent is evaporated off under vacuum. The residue is chromatographed on silica H using DCM and then a DCM/MeOH mixture (100/2; v/v) as the eluent to give 0.6 g of the expected product.

Proton NMR spectrum at 200 MHz in DMSO-$d_6$

| | |
|---|---|
| δ: | 2.3 ppm : mt : 2H |
| | 3.75 ppm : AB system : 2H |
| | 3.9 to 4.4 ppm : u : 4H |
| | 4.5 ppm : s : 2H |
| | 7.0 to 8.0 ppm : u : 13H |

B) 4-Benzyl-6-(3,4-difluorophenyl)-6-(2-hydroxyethyl)morpholin-3-one

A mixture of 0.6 g of the compound obtained in the previous step and 0.5 ml of concentrated NaOH solution in 10 ml of MeOH is stirred for 30 minutes at RT. The reaction mixture is concentrated under vacuum, the residue is extracted with AcOEt, the organic phase is washed with water and dried over $Na_2SO_4$ and the solvent is evaporated off under vacuum to give 0.42 g of the expected product, which is used as such.

C) 4-Benzyl-6-(3,4-difluorophenyl)-6-[2-(methanesulfonyloxy)ethyl]morpholin-3-one 0.137 g of methanesulfonyl chloride is added at RT to a solution of 0.42 g of the compound obtained in the previous step and 0.146 g of triethylamine in 20 ml of DCM and the mixture is stirred for 30 minutes at RT. It is concentrated under vacuum, the residue is extracted with ether, the organic phase is washed with water and dried over $Na_2SO_4$ and the solvent is evaporated off under vacuum to give 0.49 g of the expected product, which is used as such.

D) 6-[2-(4-Acetamido-4-phenylpiperid-1-yl)ethyl]-4-benzyl-6-(3,4-difluorophenyl)morpholin-3-one hydrochloride hemihydrate A mixture of 0.49 g of the compound obtained in the previous step, 0.94 g of 4-acetamido-4-phenylpiperidine p-toluenesulfonate and 0.48 g of $K_2CO_3$ in 1 ml of DMF is heated at 80° C. for 2 hours. After cooling to RT, the reaction mixture is poured into water and extracted with AcOEt, the organic phase is washed with water and dried over $Na_2SO_3$ and the solvent is evaporated off under vacuum. The residue is chromatographed on silica H using a DCM/MeOH mixture (100/3; v/v) as the eluent. The product obtained is dissolved in the minimum amount of DCM and acidified to pH 1 by the addition of a saturated solution of gaseous HCl in ether and the precipitate formed is wrung to give 0.5 g of the expected product. M.p.=273°–275° C.

EXAMPLE 26

6-(3,4-Difluorophenyl)-6-[2-[4-phenyl-1-azoniabicyclo[2.2.2]oct-1-yl]ethyl]-4-[3,5-bis(trifluoromethyl)benzyl]morpholin-3-one chloride dihydrate A) 6-[2-(Benzoyloxy)ethyl]-6-(3,4-difluorophenyl)-4-[3,5-bis(trifluoromethyl)benzyl]morpholin-3-one A mixture of 1 g of the compound obtained in Preparation 1.10 and 0.32 g of potassium tert-butylate in 20 ml of THF is stirred for 1 hour at RT, 0.735 g of 3,5-bis(trifluoromethyl)benzyl chloride is then added and the reaction mixture is refluxed for 5 hours. It is concentrated under vacuum, the residue is extracted with ether, the organic phase is washed with water and dried over $MgSO_4$ and the solvent is evaporated off under vacuum to give the expected product, which is used as such.

B) 6-(3,4-Difluorophenyl)-6-(2-hydroxyethyl)-4-[3,5-bis(trifluoromethyl)benzyl]morpholin-3-one The product obtained in the previous step is dissolved in 15 ml of MeOH, 0.235 g of lithium hydroxide monohydrate is added and the reaction mixture is stirred for 30 minutes at RT. It is concentrated under vacuum, the residue is extracted with ether, the organic phase is washed with water and dried over $MgSO_4$ and the solvent is evaporated off under vacuum. The residue is chromatographed on silica H using a DCM/MeOH mixture (100/1; v/v) as the eluent to give 0.84 g of the expected product.

Proton NMR spectrum at 200 MHz in DMSO-$d_6$

| | |
|---|---|
| δ: | 1.95 ppm : t : 2H |
| | 2.95 to 3.5 ppm : mt : 2H |
| | 3.95 ppm : AB system : 2H |

-continued

| |
|---|
| 4.25 ppm : AB system : 2H |
| 4.5 ppm : t : 1H |
| 4.7 ppm : AB system : 2H |
| 7.0 to 8.2 ppm : u : 6H |

C) 6-(3,4-Difluorophenyl)-6-[2-(methanesulfonyloxy)ethyl]-4-[3,5-bis(trifluoromethyl)benzyl]morpholin-3-one 0.22 g of methanesulfonyl chloride is added at RT to a solution of 0.8 g of the compound obtained in the previous step and 0.2 g of triethylamine in 15 ml of DCM and the reaction mixture is stirred for minutes at RT. It is concentrated under vacuum, the residue is extracted with AcOEt, the organic phase is washed with water and dried over $MgSO_4$ and the solvent is evaporated off under vacuum to give 0.9 g of the expected product, which is used as such.

D) 6-(3,4-Difluorophenyl)-6-[2-[4-phenyl-1-azoniabicyclo[2.2.2]oct-1-yl]ethyl]-4-[3,5-bis(trifluoromethyl)benzyl]morpholin-3-one chloride dihydrate A mixture of 0.9 g of the compound obtained in the previous step and 0.38 g of 4-phenyl-1-azabicyclo[2.2.2]octane in 2 ml of DMF is heated at 80° C. for hours. After cooling to RT, the reaction mixture poured into water and extracted with AcOEt, the organic phase is washed with 2N HCl solution, with water, with saturated NaCl solution and with water and dried over $Na_2SO_4$ and the solvent is evaporated off under vacuum to give 0.41 g of the expected product.

Proton NMR spectrum at 200 MHz in DMSO-$d_6$

| | |
|---|---|
| δ: | 2.0 to 2.6 ppm : u : 8H |
| | 2.7 to 3.7 ppm : u : 8H |
| | 3.9 ppm : AB system : 2H |
| | 4.1 to 5.1 ppm : u : 4H |
| | 7.0 to 8.2 ppm : u : 11H |

EXAMPLE 27

2-[2-(4-Acetamido-4-phenylpiperid-1-yl)ethyl]-4-benzoyl-2-(3,4-difluorophenyl)morpholine hydrochloride monohydrate A) 4-Benzoyl-2-(3,4-difluorophenyl)-2-(2-hydroxyethyl)morpholine A solution of 0.9 g of benzoyl chloride in 20 ml of DCM is added dropwise at RT to a solution of 0.77 g of the compound obtained in Preparation 1.11 and 0.7 g of triethylamine in 30 ml of DCM and the reaction mixture is stirred for 1 hour at RT. It is concentrated under vacuum, the residue is extracted with ether, the organic phase is washed with water and the solvent is evaporated off under vacuum. The residue is dissolved in MeOH, 0.53 g of lithium hydroxide monohydrate is added and the reaction mixture is stirred for 30 minutes at RT. It is concentrated under vacuum, the residue is extracted with DCM, the organic phase is washed with water and dried over $MgSO_4$ and the solvent is evaporated off under vacuum. The residue is chromatographed on silica H using a DCM/MeOH mixture (100/0.5; v/v) as the eluent to give 0.5 g of the expected product.

Proton NMR spectrum at 200 MHz in DMSO-$d_6$

| | |
|---|---|
| δ: | 1.95 ppm : mt : 2H |
| | 2.8 to 4.9 ppm : u : 9H |
| | 6.8 to 7.8 ppm : u : 8H |

B) 4-Benzoyl-2-(3,4-difluorophenyl)-2-[2-(methanesulfonyloxy)ethyl]morpholine

A solution of 0.19 g of methanesulfonyl chloride in 5 ml of DCM is added dropwise at RT to a solution of 0.5 g of the compound obtained in the previous step and 0.17 g of triethylamine in 20 ml of DCM and the reaction mixture is stirred for 1 hour at RT. It is concentrated under vacuum, the residue is extracted with AcOEt, the organic phase is washed with water and dried over $Na_2SO_4$ and the solvent is evaporated off under vacuum to give 0.56 g of the expected product, which is used as such.

C) 2-[2-(4-Acetamido-4-phenylpiperid-1-yl)ethyl]-4-benzoyl-2-(3,4-difluorophenyl)morpholine hydrochloride monohydrate A mixture of 0.56 g of the compound obtained in the previous step, 1 g of 4-acetamido-4-phenylpiperidine p-toluenesulfonate and 0.7 g of $K_2CO_3$ in 2 ml of DMF is heated at 80° C. for 3 hours. The reaction mixture is poured into water and extracted with AcOEt, the organic phase is washed with water and dried over $Na_2SO_4$ and the solvent is evaporated off under vacuum. The residue is chromatographed on silica H using a DCM/MeOH mixture (100/3; v/v) as the eluent. The product obtained is dissolved in the minimum amount of DCM, acidified to pH 1 by the addition of a saturated solution of gaseous HCl in ether and concentrated under vacuum to give 0.4 g of the expected product after crystallization from an EtOH/ether mixture. M.p.=179°–182° C.

EXAMPLE 28

5-(3,4-Difluorophenyl)-5-[2-[4-phenyl-1-azoniabicyclo[2.2.2]oct-1-yl]ethyl]-3-[3,5-bis(trifluoromethyl)benzyl]oxazolidin-2-one chloride 1.5 hydrate A) 5-(3,4-Difluorophenyl)-5-(2-hydroxyethyl)-3-[3,5-bis(trifluoromethyl)benzyl]oxazolidin-2-one A mixture of 1.5 g of the compound obtained in Preparation 1.12 and 0.48 g of potassium tert-butylate in 15 ml of THF is stirred for 1 hour at RT, 1.1 g of 3,5-bis(trifluoromethyl)benzyl chloride are added and the mixture is refluxed for 5 hours. It is concentrated under vacuum, the residue is taken up with a buffer solution of pH 2 and extracted with ether, the organic phase is washed with water and dried over $MgSO_4$ and the solvent is evaporated off under vacuum. The product obtained is taken up with 20 ml of MeOH, 0.2 g of lithium hydroxide monohydrate is added and the mixture is stirred for 30 minutes at RT. It is concentrated under vacuum, the residue is extracted with DCM, the organic phase is washed with water and dried over $MgSO_4$ and the solvent is evaporated off under vacuum. The residue is chromatographed on silica H using a DCM/MeOH mixture (100/1; v/v) as the eluent to give 1.3 g of the expected product.

Proton NMR spectrum at 200 MHz in DMSO-$d_6$

| | |
|---|---|
| δ: | 2.2 ppm : mt : 2H |
| | 3.0 to 3.55 ppm : mt : 2H |
| | 3.75 ppm : AB system : 2H |
| | 4.4 to 4.6 ppm : u : 3H |
| | 7.1 to 8.2 ppm : u : 6H |

B) 5-(3,4-Difluorophenyl)-5-[2-(methanesulfonyloxy)ethyl]-3-[3,5-bis(trifluoromethyl)benzyl]oxazolidin-2-one 0.34 g of methanesulfonyl chloride is added at RT to a solution of 1.3 g of the compound obtained in the previous step and 0.3 g of triethylamine in 20 ml of DCM and the reaction mixture is stirred for 30 minutes at RT. It is concentrated under vacuum, the residue is extracted with AcOEt, the organic phase is washed with water and dried over $Na_2SO_4$ and the solvent is evaporated off under vacuum to give 1.1 g of the expected product, which is used as such.

C) 5-(3,4-Difluorophenyl)-5-[2-[4-phenyl-1-azoniabicyclo[2.2.2]oct-1-yl]ethyl]-3-[3,5-bis(trifluoromethyl)benzyl]oxazolidin-2-one chloride 1.5 hydrate A mixture of 0.46 g of 4-phenyl-1-azabicyclo[2.2.2]octane and 1.1 g of the compound obtained in the previous step in 2 ml of DMF is heated at 60° C. for 5 hours. After cooling to RT, the reaction mixture is poured into water and extracted with DCM, the organic phase is washed with water, with saturated NaCl solution, with 2N HCl solution and with water and dried over $MgSO_4$ and the solvent is evaporated off under vacuum to give 0.6 g of the expected product.

Proton NMR spectrum at 200 MHz in DMSO-$d_6$

| | |
|---|---|
| δ: | 2.1 ppm : mt : 6H |
| | 2.7 ppm : t : 2H |
| | 2.85 to 4.0 ppm : u : 10H |
| | 4.6 ppm : AB system : 2H |
| | 7.1 to 8.2 ppm : u : 11H |

EXAMPLE 29

4-[2-(4-Acetamido-4-phenylpiperid-1-yl)ethyl]-1-benzyl-4-(3,4-dichlorophenyl)-3-methylimidazolidin-2-one hydrochloride A) 1-Benzyl-4-(3,4-dichlorophenyl)-3-methyl-4-[2-(tetrahydropyran-2-yloxy)ethyl]imidazolidin-2-one 0.5 g of potassium tert-butylate is added to a solution of 1.45 g of the compound obtained in Preparation 1.13 in 20 ml of THF and the mixture is stirred for 1 hour at RT. 0.48 ml of benzyl bromide is then added and the reaction mixture is stirred for 30 minutes at RT. It is concentrated under vacuum, the residue is extracted with ether, the organic phase is washed with water and dried over $MgSO_4$ and the solvent is concentrated under vacuum. The residue is chromatographed on silica using heptane and then a heptane/AcOEt mixture (40/60; v/v) as the eluent to give 1.5 g of the expected product, which is used as such.

B) 1-Benzyl-4-(3,4-dichlorophenyl)-4-(2-hydroxyethyl)-3-methylimidazolidin-2-one A saturated solution of gaseous HCl in ether is added to a solution of 1.5 g of the compound obtained in the previous step in 20 ml of MeOH until the pH is 1, and the reaction mixture is stirred for 30 minutes at RT. It is concentrated under vacuum, the residue is taken up with MeOH and the solvent is evaporated off under vacuum to give 1.05 g of the expected product after crystallization from iso ether. M.p.=118° C.

C) 1-Benzyl-4-(3,4-dichlorophenyl)-4-[2-(methanesulfonyloxy)ethyl]-3-methylimidazolidin-2-one A solution of 0.5 g of the compound obtained in the previous step and 0.34 ml of triethylamine in 10 ml of DCM is cooled to 0° C., 0.17 ml of methanesulfonyl chloride is added and the reaction mixture is stirred for 15 minutes. It is washed with water, the organic phase is dried over $MgSO_4$ and the solvent is evaporated off under vacuum to give the expected product, which is used as such.

D) 4-[2-(4-Acetamido-4-phenylpiperid-1-yl)ethyl]-1-benzyl-4-(3,4-dichlorophenyl)-3-methylimidazolidin-2-one hydrochloride A mixture of the compound obtained in the previous step, 0.8 g of 4-acetamido-4-phenylpiperidine p-toluenesulfonate and 0.8 g of $K_2CO_3$ in 5 ml of DMF is heated at 80° C. for 3 hours. After cooling to RT, the reaction mixture is poured into water and extracted with AcOEt, the organic phase is washed with 1N NaOH solution and with saturated NaCl solution and dried over $MgSO_4$ and the solvent is evaporated off under vacuum. The residue is chromatographed on silica H using DCM and then a DCM/MeOH mixture (95/5; v/v) as the eluent. The product obtained is dissolved in the minimum amount of DCM, acidified to pH 1 by the addition of a saturated solution of gaseous HCl in ether and concentrated under vacuum to give 0.3 g of the expected product after crystallization from iso ether.

M.p.=206° C.

EXAMPLE 30

4-(3,4-Dichlorophenyl)-4-[2-[4-phenyl-1-azoniabicyclo[2.2.2]oct-1-yl]ethyl]-3-methyl-1-[3,5-bis(trifluoromethyl)benzyl]imidazolidin-2-one chloride A) 4-(3,4-Dichlorophenyl)-3-methyl-4-[2-(tetrahydropyran-2-yloxy)ethyl]-1-[3,5-bis(trifluoromethyl)benzyl]imidazolidin-2-one A mixture of 1.45 g of the compound obtained in Preparation 1.13 and 0.5 g of potassium tert-butylate in 20 ml of THF is stirred for 1 hour at RT, 1.04 g of 3,5-bis(trifluoromethyl)benzyl chloride are then added and the reaction mixture is stirred for 2 hours at RT. It is concentrated under vacuum, the residue is extracted with ether, the organic phase is washed with water and with saturated NaCl solution and dried over $MgSO_4$ and the solvent is evaporated off under vacuum. The residue is chromatographed on silica using heptane and then a heptane/AcOEt mixture (50/50; v/v) as the eluent to give 2.1 g of the expected product, which is used as such.

B) 4-(3,4-Dichlorophenyl)-4-(2-hydroxyethyl)-3-methyl-1-[3,5-bis(trifluoromethyl)benzyl]imidazolidin-2-one 1 ml of a saturated solution of gaseous HCl in ether is added to a solution of 2.1 g of the compound obtained in the previous step in 20 ml of MeOH and the mixture is stirred for 30 minutes at RT. It is concentrated under vacuum, the residue is taken up with MeOH and the solvent is evaporated off under vacuum to give 1.7 g of the expected product after crystallization from an iso ether/pentane mixture. M.p.=96° C.

C) 4-(3,4-Dichlorophenyl)-4-[2-(methanesulfonyloxy)ethyl]-3-methyl-1-[3,5-bis(trifluoromethyl)benzyl]imidazolidin-2-one A solution of 0.56 g of the compound obtained in the previous step and 0.3 ml of triethylamine in 10 ml of DCM is cooled to 0° C., 0.15 ml of methanesulfonyl chloride is added and the reaction mixture is stirred for 15 minutes. It is washed with water, the organic phase is dried over $MgSO_4$ and the solvent is evaporated off under vacuum to give the expected product, which is used as such.

D) 4-(3,4-Dichlorophenyl)-4-[2-[4-phenyl-1-azoniabicyclo[2.2.2]oct-1-yl]ethyl]-3-methyl-1-[3,5-bis(trifluoromethyl)benzyl]imidazolidin-2-one chloride A mixture of the compound obtained in the previous step and 0.35 g of 4-phenyl-1-azabicyclo[2.2.2]octane in 1 ml of DMF is heated at 80° C. for 3 hours. After cooling to RT, the reaction mixture is poured into a mixture of 50 ml of water, 50 ml of DCM and 3 ml of concentrated HCl and stirred for 5 minutes. The precipitate formed is wrung, washed with water with DCM and then with ether and dried to give 0.3 g of the expected product. M.p.=290° C.

EXAMPLE 31

6-[3-(4-Acetamido-4-phenylpiperid-1-yl)propyl]-4-benzyl-6-(3,4-dichlorophenyl)morpholin-3-one hydrochloride A) 4-Benzyl-6-[3-(benzoyloxy)propyl]-6-(3,4-dichlorophenyl)morpholin-3-one 0.369 g of potassium tert-butylate is added to a solution of 1.34 g of the compound obtained in Preparation 1.14 in 20 ml of THF and the mixture is stirred for 1 hour at RT. 0.564 g of benzyl bromide is then added and the reaction mixture is refluxed for 2 hours. It is concentrated under vacuum, the residue is taken up with a buffer solution of pH 2 and extracted with ether, the organic phase is washed with water and dried over $MgSO_4$and the solvent is evaporated off under vacuum to give the expected product, which is used as such.

B) 4-Benzyl-6-(3,4-dichlorophenyl)-6-(3-hydroxypropyl) morpholin-3-one 0.277 g of lithium hydroxide monohydrate is added to a solution of the compound obtained in the previous step in 20 ml of MeOH and the mixture is stirred for 1 hour at RT. It is concentrated under vacuum, the residue is extracted with ether, the organic phase is washed with water and dried over $MgSO_4$ and the solvent is evaporated off under vacuum to give 0.9 g of the expected product, which is used as such.

Proton NMR spectrum at 200 MHz in DMSO-$d_6$

| | |
|---|---|
| δ: | 0.9 to 2.1 ppm : u : 4H |
| | 3.3 ppm : q : 2H |
| | 3.7 ppm : AB system : 2H |
| | 4.15 ppm : AB system : 2H |
| | 4.4 ppm : t : 1H |
| | 4.5 ppm : AB system : 2H |
| | 7.1 to 7.8 ppm : u : 8H |

C) 4-Benzyl-6-(3,4-dichlorophenyl)-6-[3-(methanesulfonyloxy)propyl]morpholin-3-one 0.316 g of methanesulfonyl chloride is added at RT to a solution of 0.9 g of the compound obtained in the previous step and 0.288 g of triethylamine in 50 ml of DCM and the mixture is stirred for 30 minutes at RT. It is concentrated under vacuum, the residue is extracted with AcOEt, the organic phase is washed with water and dried over $MgSO_4$ and the solvent is evaporated off under vacuum to give 1.08 g of the expected product, which is used as such.

D) 6-[3-(4-Acetamido-4-phenylpiperid-1-yl)propyl]-4-benzyl-6-(3,4-dichlorophenyl)morpholin-3-one hydrochloride A mixture of 1.08 g of the compound obtained in the previous step, 1.4 g of 4-acetamido-4-phenylpiperidine p-toluenesulfonate and 1.3 g of $K_2CO_3$ in 5 ml of DMF is heated at 80° C. for 3 hours. After cooling, the reaction mixture is poured into water and extracted with AcOEt, the organic phase is washed with water and dried over $MgSO_4$ and the solvent is evaporated off under vacuum. The residue is chromatographed on silica H using a DCM/MeOH mixture (100/3; v/v) as the eluent. The product obtained is dissolved in DCM, a saturated solution of gaseous HCl in ether is added until the pH is 1, and the solvent is evaporated off under vacuum to give 0.6 g of the expected product after crystallization from an EtOH/ether mixture. M.p.=151°–153° C.

EXAMPLE 32

4-(3,4-Dichlorophenyl)-3-methyl-4-[2-(4-phenylpiperid-1-yl)ethyl]-1-[3,5-bis(trifluoromethyl) benzyl]-imidazolidin-2-one hydrochloride A mixture of 0.55 g of the compound obtained in step C of EXAMPLE 30, 0.47 g of 4-phenylpiperidine and 0.5 g of $K_2CO_3$ in 4 ml of DMF is heated at 80° C. for 5 hours. After cooling, the reaction mixture is poured into iced water and extracted with AcOEt, the organic phase is washed with 1N NaOH solution and with water and dried over $MgSO_4$ and the solvent is evaporated off under vacuum. The residue is chromatographed on silica H using DCM and then a DCM/MeOH mixture (98/2; v/v) as the eluent. The product obtained is dissolved in ether, a saturated solution of gaseous HCl in ether is added until the pH is 1, and the precipitate formed is wrung to give 0.25 g of the expected product.

M.p.=208° C.

EXAMPLE 33

4-Benzyl-6-(3,4-dichlorophenyl)-6-[2-[4-phenyl-4-(pyrrolidin-1-ylcarbonyl)piperid-1-yl]ethyl] morpholin-3-one hydrochloride monohydrate A mixture of 0.98 g of the compound obtained in step B of EXAMPLE 14, 0.645 g of 4-phenyl-4-(pyrrolidin-1-ylcarbonyl)piperidine and 0.69 g of $K_2CO_3$ in 3 ml of DMF is heated at 80° C. for 2 hours. After cooling to RT, the reaction mixture is poured into water and extracted with an AcOEt/ether mixture, the organic phase is washed with water and dried over $MgSO_4$ and the solvent is evaporated off under vacuum. The residue is chromatographed on silica H using a DCM/MeOH mixture (100/2; v/v) as the eluent. The product obtained is dissolved in the minimum amount of DCM and acidified to pH 1 by the addition of a saturated solution of gaseous HCl in ether and the precipitate formed is wrung to give 0.42 g of the expected product. M.p.=155°–178° C.

EXAMPLE 34

6-[2-[4-(Acetyl-N-methylamino)-4-phenylpiperid-1-yl]ethyl]-4-benzyl-6-(3,4-dichlorophenyl)morpholin-3-one hydrochloride monohydrate A mixture of 1.1 g of the compound obtained in step B of EXAMPLE 14, 1.85 g of 4-(acetyl-N-methylamino)-4-phenylpiperidine p-toluenesulfonate and 1.3 g of $K_2CO_3$ in 3 ml of DMF is heated at 80°–100° C. for 2 hours. After cooling to RT, the reaction mixture is poured into water and extracted with ether, the organic phase is washed with water and dried over $MgSO_4$ and the solvent is evaporated off under vacuum. The residue is chromatographed on silica H using a DCM/MeOH mixture (from 100/1; v/v to 100/4; v/v) as the eluent. The product obtained is dissolved in DCM, a saturated solution of hydrochloric acid in ether is added until the pH is 1, and the precipitate formed is wrung to give 0.62 g of the expected product. M.p.=148°–150° C.

EXAMPLE 35

4-Benzyl-6-[2-[4-(ethoxycarbonylamino)-4-phenylpiperid-1-yl]ethyl]-6-(3,4-dichlorophenyl) morpholin-3-one hydrochloride monohydrate A mixture of 1.1 g of the compound obtained in step B of EXAMPLE 14, 1 g of 4-(ethoxycarbonylamino)-4-phenylpiperidine trifluoroacetate and 0.7 g of $K_2CO_4$ in 3 ml of DMF is heated at 80°–100° C. for 2 hours. After cooling to RT, the reaction mixture is poured into water and stirred for 30 minutes and the precipitate formed is wrung, washed with water and dried under vacuum at 60° C. The precipitate is chromatographed on silica H using a DCM/MeOH mixture (from 100/1; v/v to 100/4.5; v/v) as the eluent. The product obtained is dissolved in DCM, a saturated solution of hydrochloric acid in ether is added until the pH is 1, and the precipitate formed is wrung to give 0.52 g of the expected product. M.p.=148°–150° C.

EXAMPLE 36

4-Benzoyl-2-(3,4-difluorophenyl)-2-[2-[4-(N',N'-dimethylureido)-4-phenylpiperid-1-yl]ethyl] morpholine hydrochloride monohydrate, (−) isomer A) 4-Benzoyl-2-[2-(benzoyloxy)ethyl]-2-(3,4-difluorophenyl)morpholine, (−) isomer A solution of 8.9 g of the compound obtained in Preparation 1.17 ((−) isomer) and 3 g of triethylamine in 100 ml of DCM is cooled to 0° C., a solution of 3.59 g of benzoyl chloride in 20 ml of DCM is added dropwise and the reaction mixture is stirred for 30 minutes. It is concentrated under vacuum, the residue is extracted with ether, the organic phase is washed with water and dried over $MgSO_4$ and the solvent is evaporated off under vacuum. The residue is chromatographed on silica H using a DCM/MeOH mixture (100/0.5; v/v) as the eluent to give 9.3 g of the expected product.

$[\alpha]_D^{20}=-4.7°$ (c=1; MeOH)

B) 4-Benzoyl-2-(3,4-difluorophenyl)-2-(2-hydroxyethyl) morpholine, (−) isomer 6.6 g of 30 % aqueous NaOH solution are added dropwise at RT to a solution of 11.5 g of the compound obtained in the previous step in 60 ml of MeOH and the reaction mixture is stirred for 1 hour. It is concentrated under vacuum, the residue is taken up with water and extracted with ether, the organic phase is washed with water and dried over $MgSO_4$ and the solvent is evaporated off under vacuum. The residue is chromatographed on silica H using a DCM/MeOH mixture (from 100/1; v/v to 100/5; v/v) as the eluent to give 8.4 g of the expected product after crystallization from iso ether. M.p.=80° C.

$[\alpha]_D^{20}=56.1°$ (c=1; MeOH)

C) 4-Benzoyl-2-(3,4-difluorophenyl)-2-[2-(methanesulfonyloxy)ethyl]morpholine, (−) isomer A solution of 0.36 g of methanesulfonyl chloride in 3 ml of DCM is added dropwise at RT to a solution of 1 g of the compound obtained in the previous step and 0.3 g of triethylamine in 25 ml of DCM and the reaction mixture is stirred for 30 minutes at RT. It is concentrated under vacuum, the residue is extracted with ether, the organic phase is washed with water, with saturated $NaHCO_3$ solution and with water and dried over $MgSO_4$ and the solvent is evaporated off under vacuum to give 1.05 g of the expected product.

$[\alpha]_D^{20}=-36.1°$ (c=1; MeOH)

D) 4-Benzoyl-2-(3,4-difluorophenyl)-2-[2-[4-(N',N'-dimethylureido)-4-phenylpiperid-1-yl]ethyl]morpholine hydrochloride monohydrate, (−) isomer 2 g of the compound obtained in Preparation 2.2 are dissolved in water, rendered alkaline by the addition of concentrated NaOH solution and extracted with DCM, the organic phase is dried over $MgSO_4$ and the solvent is evaporated off under vacuum to give 1.08 g of the free base. The product obtained is taken up with 3 ml of DMF, 0.95 g of the compound obtained in the previous step is added and the reaction mixture is heated at 80° C. for 3 hours. After cooling, it is poured into water and the precipitate formed is wrung and washed with water. The precipitate is dissolved in DCM, the organic phase is washed with 10% NaOH solution and dried over $MgSO_4$ and the solvent is evaporated off under vacuum. The residue is chromatographed on silica H using a DCM/MeOH mixture (from 100/1; v/v to 100/7.5; v/v) as the eluent. The product obtained is dissolved in DCM, a saturated solution of hydrochloric acid in ether is added until the pH is 1, and the solvents are evaporated off under vacuum to give 0.3 g of the expected product after crystallization from a DCM/pentane mixture. M.p.=168°–172° C.

$[\alpha]_D^{20}=22.2°$ (c=1; MeOH)

EXAMPLE 37

4-Benzoyl-2-(3,4-difluorophenyl)-2-[2-[4-(N',N'-dimethylureido)-4-phenylpiperid-1-yl]ethyl] morpholine hydrochloride hemihydrate, (+) isomer A) 4-Benzoyl-2-[2-(benzoyloxy)ethyl]-2-(3,4-difluorophenyl)morpholine, (+) isomer A solution of 20 g of the compound obtained in Preparation 1.18 ((+) isomer) and 8 ml of triethylamine in 200 ml of DCM is cooled to 0° C., 6 ml of benzoyl chloride are added dropwise and the reaction mixture is stirred for 15 minutes. It is concentrated under vacuum, the residue is extracted with ether, the organic phase is washed with water, with 1N HCl solution and with 10% $Na_2CO_3$ solution and dried over $MgSO_4$ and the solvent is evaporated off under vacuum to give 22 g of the expected product in the form of an oil.

$[\alpha]_D^{20}=+4.7°$ (c=1; MeOH)

B) 4-Benzoyl-2-(3,4-difluorophenyl)-2-(2-hydroxyethyl) morpholine, (+) isomer

A mixture of 22 g of the compound obtained in the previous step, 9 ml of 30 % aqueous NaOH solution and 200 ml of 95° EtOH is stirred for 1 hour at RT. The reaction mixture is concentrated under vacuum, the residue is extracted with ether, the organic phase is washed three times with water and dried over $MgSO_4$ and the solvent is evaporated off under vacuum to give 13.7 g of the expected product after crystallization from an ether/iso ether mixture. M.p.=80° C.

$[\alpha]_D^{20}=+59.5°$ (c=1; MeOH)

C) 4-Benzoyl-2-(3,4-difluorophenyl)-2-[2-(methanesulfonyloxy)ethyl]morpholine, (+) isomer A solution of 1 g of the compound obtained in the previous step and 0.45 ml of triethylamine in 10 ml of DCM is cooled to 0° C., 0.25 ml of methanesulfonyl chloride is added and the reaction mixture is stirred for 15 minutes. It is washed with water and with 10% $NaHCO_3$ solution, the organic phase is dried over $MgSO_4$ and the solvent is evaporated off under vacuum to give 1.2 g of the expected product in the form of an oil.

D) 4-Benzoyl-2-(3,4-difluorophenyl)-2-[2-[4-(N',N'-dimethylureido)-4-phenylpiperid-1-yl]ethyl]morpholine hydrochloride hemihydrate, (+) isomer A mixture of 1.2 g of the compound obtained in the previous step, 3 g of the compound obtained in Preparation 2.2 and 2 g of $K_2CO_3$ in 10 ml of DMF is heated at 80° C. for 3 hours. The reaction mixture is poured into iced water and extracted with AcOEt, the organic phase is washed with 1N NaOH solution and with saturated NaCl solution and dried over $MgSO_4$ and the solvent is evaporated off under vacuum. The residue is chromatographed on silica H using DCM and then a DCM/MeOH mixture (96/4; v/v) as the eluent. The product obtained is dissolved in DCM, a saturated solution of gaseous HCl in ether is added until the pH is 1, and the solvent is evaporated off under vacuum to give 0.66 g of the expected product after crystallization from iso ether.

$[\alpha]_D^{20}=+22.2°$ (c=1; MeOH)

EXAMPLE 38

5-(3,4-Dichlorophenyl)-5-[2-(4-phenylpiperid-1-yl) ethyl]-3-[3,5-bis(trifluoromethyl)benzyl]oxazolidin-2-one hydrochloride A mixture of 1.5 g of the compound obtained in step B of EXAMPLE 21 and 1.03 g of 4-phenylpiperidine in 3 ml of DMF is heated at 80° C. for 3 hours. After cooling, the reaction mixture is poured into water and extracted with AcOEt, the organic phase is washed with water and dried over $MgSO_4$ and the solvent is evaporated off under vacuum. The residue is chromatographed on silica H using a DCM/MeOH mixture (100/1; v/v) as the eluent. The product obtained is dissolved in DCM, a saturated solution of gaseous HCl in ether is added until the pH is 1, and the solvent is evaporated off under vacuum to give 0.7 g of the expected product after crystallization from a DCM/pentane mixture.

M.p.=112°–114° C.

EXAMPLE 39

5-[2-(4-Acetamido-4-phenylpiperid-1-yl)ethyl]-5-(3,4-dichlorophenyl)-3-[3,5-bis(trifluoromethyl)benzyl]oxazolidin-2-one hydrochloride monohydrate A mixture of 1.5 g of the compound obtained in step B of EXAMPLE 21, 1.5 g of 4-acetamido-4-phenylpiperidine p-toluenesulfonate and 1.6 g of $K_2CO_3$ in 4 ml of DMF is heated at 80° C. for 3 hours. After cooling, the reaction mixture is poured into water and extracted with an AcOEt/ether mixture (50/50; v/v), the organic phase is washed with water and dried over $MgSO_4$ and the solvent is evaporated off under vacuum. The residue is chromatographed on silica H using a DCM/MeOH mixture (100/3; v/v) as the eluent. The product obtained is dissolved in DCM, a saturated solution of gaseous HCl in ether is added until the pH is 1, and the solvent is evaporated off under vacuum to give 0.66 g of the expected product after crystallization from a DCM/pentane mixture. M.p.=165°–170° C.

EXAMPLE 40

5-[2-[4-Benzyl-1-azoniabicyclo[2.2.2]oct-1-yl]ethyl]-5-(3,4-dichlorophenyl)-3-[3,5-bis(trifluoromethyl)benzyl]oxazolidin-2-one chloride monohydrate A mixture of 1.4 g of the compound obtained in step B of EXAMPLE 21 and 0.6 g of 4-benzylquinuclidine in 3 ml of DMF is heated at 80° C. for 2 hours. After cooling to RT, the reaction mixture is poured into water and extracted with AcOEt, the organic phase is washed with water, with 300 ml of 10% HCl solution and with 300 ml of saturated NaCl solution and dried over $MgSO_4$ and the solvent is evaporated off under vacuum to give 1.35 g of the expected product after crystallization from AcOEt. M.p.=172°–175° C.

EXAMPLE 41

4-Benzyl-6-(3,4-dichlorophenyl)-6-[2-[4-phenyl-4-(pyrrolidin-1-ylcarbonylamino)piperid-1-yl]ethyl]-morpholin-3-one hydrochloride monohydrate A mixture of 1.1g of the compound obtained in step B of EXAMPLE 14, 1.2 g of 4-phenyl-4-(pyrrolidin-1-ylcarbonylamino)piperidine benzenesulfonate and 0.95 g of $K_2CO_3$ in 3 ml of DMF is heated at 80°–100° C. for 3 hours. After cooling to RT, the reaction mixture is poured into water and the precipitate formed wrung, washed with water and dried under vacuum The precipitate is chromatographed on silica H using a DCM/MeOH mixture (from 100/2; v/v to 100/3; v/v) as the eluent. The product obtained is dissolved in the minimum amount of DCM and acidified to pH 1 by the addition of a saturated solution of gaseous HCl in ether and the precipitate formed is wrung to give 0.54 g of the expected product. M.p.=158°–160° C.

EXAMPLE 42

4-Benzyl-6-(3,4-dichlorophenyl)-6-[2-[4-(2-dimethylaminothiazol-4-yl)-4-phenylpiperid-1-yl]ethyl]morpholin-3-one dihydrochloride This compound is prepared by the procedure described in EXAMPLE 41 from 1.1 g of the compound obtained in step B of EXAMPLE 14, 1.3 g of 4-[2-(dimethylamino)thiazol-4-yl]-4-phenylpiperidine p-toluenesulfonate, 0.97 g of $K_2CO_3$ and 4 ml of DMF to give 0.76 g of the expected product. M.p.=155°–160° C.

EXAMPLE 43

4-Benzoyl-2-(3,4-dichlorophenyl)-2-[2-[4-(morpholin-4-ylcarbonylamino)-4-phenylpiperid-1-yl]ethyl]morpholine hydrochloride monohydrate A) 4-Benzoyl-2-[2-(benzoyloxy)ethyl]-2-(3,4-dichlorophenyl)morpholine 2.03 g of benzoyl chloride are added dropwise at RT to a solution of 5 g of the compound obtained in Preparation 1.19 and 1.4 g of triethylamine in 100 ml of DCM and the reaction mixture is stirred for 30 minutes at RT. It is concentrated under vacuum, the residue is extracted with ether, the organic phase is washed with water and dried over $MgSO_4$ and the solvent is evaporated off under vacuum. The residue is chromatographed on silica H using a DCM/MeOH mixture (100/1; v/v) as the eluent to give 4 g of the expected product.

B) 4-Benzoyl-2-(3,4-dichlorophenyl)-2-(2-hydroxyethyl)morpholine

A mixture of 4 g of the compound obtained in the previous step and 0.7 g of lithium hydroxide monohydrate in 50 ml of MeOH is stirred for 30 minutes at RT. The reaction mixture is concentrated under vacuum, the residue is extracted with ether, the organic phase is washed with water and dried over $MgSO_4$ and the solvent is evaporated off under vacuum to give 3.1 g of the expected product.

This compound is also prepared by the procedure described in step A of EXAMPLE 17.

C) 4-Benzoyl-2-(3,4-dichlorophenyl)-2-[2-(methanesulfonyloxy)ethyl]morpholine 1.07 g of methanesulfonyl chloride are added dropwise at RT to a solution of 3.1 g of the compound obtained in the previous step and 0.95 g of triethylamine in 50 ml of DCM and the reaction mixture is stirred for 1 hour at RT. It is concentrated under vacuum, the residue is extracted with an AcOEt/ether mixture (50/50; v/v), the organic phase is washed with water and dried over $MgSO_4$ and the solvent is evaporated off under vacuum to give 3.7 g of the expected product, which is used as such.

This compound is also prepared by the procedure described in step B of EXAMPLE 17.

D) 4-Benzoyl-2-(3,4-dichlorophenyl)-2-[2-[4-(morpholin-4-ylcarbonylamino)-4-phenylpiperid-1-yl]ethyl]morpholine hydrochloride monohydrate A mixture of 1.3 g of the compound obtained in the previous step, 1.5 g of 4-(morpholin-4-ylcarbonylamino)-4-phenylpiperidine p-toluenesulfonate and 1.2 g of $K_2CO_3$ in 3 ml of DMF is heated at 100° C. for 3 hours. After cooling to RT, the reaction mixture is poured into water and the precipitate formed is wrung and dried under vacuum. The precipitate is chromatographed on silica H using a DCM/MeOH mixture (from 100/2; v/v to 100/3; v/v) as the eluent. The product obtained is dissolved in the minimum amount of DCM, acidified to pH 1 by the addition of a saturated solution of gaseous HCl in ether and concentrated under vacuum to give 0.13 g of the expected product after crystallization from iso ether.

Proton NMR spectrum at 200 MHz in DMSO-$d_6$

| | |
|---|---|
| δ: | 1.8 to 4.0 ppm : u : 26H |
| | 6.5 ppm : s : 1H |
| | 6.9 to 7.8 ppm : u : 13H |
| | 10.65 ppm : s : 1H |

EXAMPLE 44

4-Benzoyl-2-(3,4-dichlorophenyl)-2-[2-[4-phenyl-4-(pyrrolidin-1-ylaminocarbonyl)piperid-1-yl]ethyl] morpholine dihydrochloride dihydrate A mixture of 1.3 g of the compound obtained in step C of EXAMPLE 43, 1.46 g of 4-phenyl-4-(pyrrolidin-1-ylaminocarbonyl)piperidine benzenesulfonate and 1.17 g of $K_2CO_3$ in 5 ml of acetonitrile and 5 ml of DMF is heated at 100° C. for 4 hours. After cooling to RT, the reaction mixture is poured into water and extracted with AcOEt, the organic phase is washed twice with water and with saturated NaCl solution and dried over $MgSO_4$ and the solvent is evaporated off under vacuum. The residue is chromatographed on silica H using DCM and then a DCM/MeOH mixture (97/3; v/v) as the eluent. The product obtained is dissolved in acetone, a saturated solution of hydrochloric acid in ether is added until the pH is 1, and the precipitate formed is wrung to give 1.01 g of the expected product.

M.p.=170°–174° C.

EXAMPLE 45

4-Benzoyl-2-(3,4-difluorophenyl)-2-[2-[4-(methoxycarbonylamino)-4-phenylpiperid-1-yl] ethyl]morpholine hydrochloride monohydrate, (+) isomer A mixture of 1.2 g of the compound obtained in step C of EXAMPLE 37, 1.3 g of 4-(methoxycarbonylamino)-4-phenylpiperidine p-toluenesulfonate and 1.2 g of $K_2CO_3$ in 3 ml of DMF is heated at 80°–100° C. for 2 hours. After cooling to RT, the reaction mixture is poured into water and the precipitate formed is wrung and dried under vacuum. The precipitate is chromatographed on silica H using a DCM/MeOH mixture (from 100/1.5; v/v to 100/3; v/v) as the eluent. The product obtained is dissolved in DCM, a saturated solution of hydrochloric acid in ether is added until the pH is 1, and the precipitate formed is wrung to give 0.8 g of the expected product. M.p.=170° C.

$[\alpha]_D^{20}$=+26.7° (c=1; MeOH)

EXAMPLE 46

4-Benzoyl-2-(3,4-difluorophenyl)-2-[2-[4-phenyl-4-(pyrrolidin-1-ylcarbonylamino)piperid-1-yl]ethyl] morpholine hydrochloride monohydrate, (+) isomer This compound is prepared by the procedure described in EXAMPLE 45 from 1.2 g of the compound obtained in step C of EXAMPLE 37, 1.4 g of 4-phenyl-4-(pyrrolidin-1-ylcarbonylamino)piperidine benzenesulfonate, 1.2 g of $K_2CO_3$ and 2 ml of DMF to give 0.3 g of the expected product. M.p.=163°–168° C.

$[\alpha]_D^{20}$=+22.8° (c=1; MeOH)

EXAMPLE 47

4-Benzoyl-2-[2-[4-benzyl-4-(pyrrolidin-1-yl-carbonylamino)piperid-1-yl]ethyl]-2-(3,4-difluorophenyl)morpholine hydrochloride 1.5 hydrate, (+) isomer This compound is prepared by the procedure described in EXAMPLE 45 from 1.2 g of the compound obtained in step C of EXAMPLE 37, 1.5 g of 4-benzyl-4-(pyrrolidin-1-ylcarbonylamino)piperidine p-toluenesulfonate, 1.2 g of $K_2CO_3$ and 3 ml of DMF to give 0.83 g of the expected product. M.p.=140° C.

$[\alpha]_D^{20}$=+28.4° (c=1; MeOH)

EXAMPLE 48

4-Benzoyl-2-(3,4-difluorophenyl)-2-[2-[4-[2-(dimethylamino)thiazol-4-yl]-4-phenylpiperid-1-yl] ethyl]morpholine dihydrochloride hemihydrate, (+) isomer This compound is prepared by the procedure described in EXAMPLE 45 from 1.2 g of the compound obtained in step C of EXAMPLE 37, 1.55 g of 4-[2-(dimethylamino)thiazol-4-yl]-4-phenylpiperidine p-toluenesulfonate, 1.2 g of $K_2CO_3$ and 3 ml of DMF to give 0.7 g of the expected product. M.p.=147° C.

$[\alpha]_D^{20}$=+20.3° (c=1; MeOH)

EXAMPLE 49

2-[2-[4-(2-Amino-1,3,4-oxadiazol-5-yl)-4-phenylpiperid-1-yl]ethyl]-4-benzoyl-2-(3,4-difluorophenyl)morpholine dihydrochloride, (+) isomer This compound is prepared by the procedure described in EXAMPLE 45 from 1.2 g of the compound obtained in step C of EXAMPLE 37, 1.4 g of 4-(2-amino-1,3,4-oxadiazol-5-yl)-4-phenylpiperidine p-toluenesulfonate, 1.2 g of $K_2CO_3$ and 3 ml of DMF to give 0.6 g of the expected product. M.p.=153° C.

$[\alpha]_D^{20}$=+27.2° (c=1; MeOH)

EXAMPLE 50

5-(3,4-Difluorophenyl)-5-[2-[4-phenyl-1-azoniabicyclo[2.2.2]oct-1-yl]ethyl]-3-[3,5-bis (trifluoromethyl)benzyl]oxazolidin-2-one chloride monohydrate, (–) isomer A) 5-[2-(Benzoyloxy)ethyl]-5-(3,4-difluorophenyl)-3-[3,5-bis(trifluoromethyl)benzyl]oxazolidin-2-one, (–) isomer 1.2 g of potassium tert-butylate are added at RT to a solution of 3.5 g of the compound obtained in Preparation 1.20 ((–) isomer) in a mixture of 50 ml of THF and 10 ml of DMF and the mixture is stirred for 30 minutes at RT. 2.7 g of 3,5-bis(trifluoromethyl)benzyl chloride are then added and the reaction mixture is heated at 60° C. for 6 hours. It is poured into 200 ml of a buffer of pH 2 and extracted with ether, the organic phase is washed with water and dried over $MgSO_4$ and the solvent is evaporated off under vacuum. The residue is chromatographed on silica H using DCM as the eluent to give 3.6 g of the expected product.

B) 5-(3,4-Difluorophenyl)-5-(2-hydroxyethyl)-3-[3,5-bis (trifluoromethyl)benzyl]oxazolidin-2-one, (–) isomer A mixture of 3.6 g of the compound obtained in the previous step and 0.32 g of lithium hydroxide monohydrate in 50 ml of MeOH and 5 ml of water is stirred for 2 hours at RT. The reaction mixture is concentrated under vacuum, the residue is taken up with water and extracted with ether, the organic phase is washed twice with water and dried over $MgSO_4$ and the solvent is evaporated off under vacuum. The residue is chromatographed on silica H using DCM and then a DCM/MeOH mixture (98/2; v/v) as the eluent to give 2.6 g of the expected product.

C) 5-(3,4-Difluorophenyl)-5-[2-(methanesulfonyloxy)ethyl]-3-[3,5-bis(trifluoromethyl)benzyl]oxazolidin-2-one, (–) isomer A solution of 2.6 g of the compound obtained in the previous step in 50 ml of DCM is cooled to 0° C., 1.14 ml of triethylamine and then 0.62 ml of methanesulfonyl chloride are added and the reaction mixture is stirred for 10 minutes. It is concentrated under vacuum, the residue is extracted with ether, the organic phase is washed twice with water and dried over $MgSO_4$ and the solvent is evaporated off under vacuum to give 3 g of the expected product, which is used as such.

D) 5-(3,4-Difluorophenyl)-5-[2-[4-phenyl-1-azoniabicyclo[2.2.2]oct-1-yl]ethyl]-3-[3,5-bis(trifluoromethyl)benzyl]oxazolidin-2-one chloride monohydrate, (–) isomer A mixture of 2 g of the compound obtained in the previous step and 1 g of 4-phenyl-1-azabicyclo[2.2.2]octane in 1 ml of DMF is heated at 90° C. for 2 hours. After cooling to RT, the reaction mixture is poured into 1N HCl solution and extracted with DCM, the organic phase is washed with 1N HCl solution and with saturated NaCl solution and dried over $MgSO_4$ and the solvent is evaporated off under vacuum. The residue is chromatographed on silica H using DCM and then a DCM/MeOH mixture (90/10; v/v) as the eluent to give 1.45 g of the expected product after crystallization from iso ether. M.p.=130° C. (dec.).

$[\alpha]_D^{20}$=–36.2° (c=1; MeOH)

EXAMPLE 51

4-Benzoyl-2-(3,4-difluorophenyl)-2-[2-[4-(N',N'-dimethylureido)-4-phenylpiperid-1-yl]ethyl]morpholine fumarate A) 4-Benzoyl-2-(3,4-difluorophenyl)-2-(formylmethyl)morpholine A solution of 0.32 ml of oxalyl chloride in 7.3 ml of DCM is cooled to –78° C. under a nitrogen atmosphere and a solution of 0.51 ml of DMSO in 3.5 ml of DCM is added dropwise, followed by a solution of 1 g of the compound obtained in step A of EXAMPLE 27 in 7.5 ml of DCM and 0.7 ml of DMSO. The reaction mixture is stirred for 30 minutes at –60° C., 2 ml of triethylamine are then added and the reaction mixture is stirred while the temperature is allowed to rise to RT. It is washed with 1N HCl solution, with saturated $Na_2CO_3$ solution and with water, the organic phase is dried over $MgSO_4$ and the solvent is evaporated off under vacuum to give 1.03 g of the expected product in the form of an oil.

Proton NMR spectrum at 200 MHz in DMSO-$d_6$

| | |
|---|---|
| δ: | 2.7 to 4.8 ppm : u : 8H<br>7.0 to 8.0 ppm : u : 8H<br>9.6 ppm : s : 1H |

B) 4-Benzoyl-2-(3,4-difluorophenyl)-2-[2-[4-(N',N'-dimethylureido)-4-phenylpiperid-1-yl]ethyl]morpholine fumarate A solution of 1 g of the compound obtained in the previous step in 10 ml of MeOH is added at RT to a solution of 0.72 g of 4-(N',N'-dimethylureido)-4-phenylpiperidine (free base) and 0.16 ml of acetic acid in 10 ml of MeOH and the mixture is stirred for 5 minutes at RT. A solution of 0.19 g of sodium cyanoborohydride in 10 ml of MeOH is then added all at once and the reaction mixture is stirred for 4 hours at RT. It is neutralized by the addition of 10% $Na_2CO_3$ solution and extracted with DCM, the organic phase is dried over $MgSO_4$ and the solvent is evaporated off under vacuum. The residue is chromatographed on silica H using DCM and then a DCM/MeOH mixture (96/4; v/v) as the eluent. The product obtained (1.1 g) is dissolved in 20 ml of acetone, 0.24 g of fumaric acid is added and the mixture is stirred for 1 hour at RT. The crystalline product formed is wrung and washed with acetone and then with ether to give 1.35 g of the expected product. M.p.=204° C.

The compounds according to the invention which are collated in TABLE I below are prepared by the procedure described in EXAMPLE 34 from the compound obtained in step B of EXAMPLE 14 and the piperidines described in the Preparations.

TABLE I

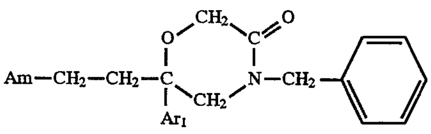

(I)

| Example | AM | $Ar_1$ | Salt, solvate; M.p. °C. or NMR; recrystallization solvent |
|---|---|---|---|
| 52 | 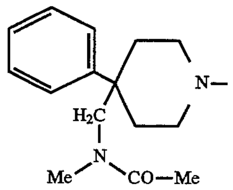 | 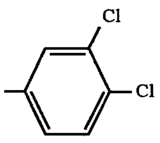 | HCl, $2.5H_2O$<br>138–140<br>pentane/ether |

TABLE I-continued
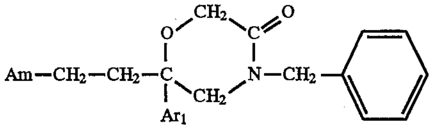
(I)
| Example | AM | $Ar_1$ | Salt, solvate; M.p. °C. or NMR; recrystallization solvent |
|---|---|---|---|
| 53 | 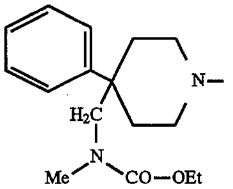 | 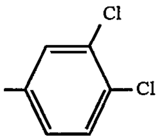 | HCl, $2H_2O$<br>128 (dec)<br>pentane/ether |
| 54 | 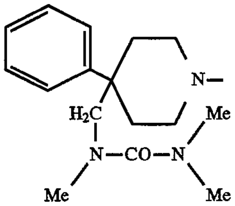 | 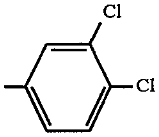 | HCl, $2.5H_2O$<br>138–140<br>pentane/ether |
| 55 | 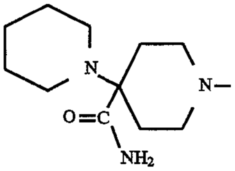 | 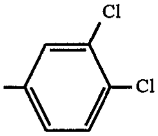 | 2HCl, $2H_2O$<br>198 (dec)<br>pentane/iso ether |
| 56 | 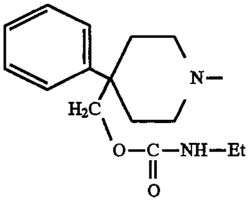 | 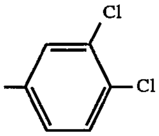 | HCl, $1H_2O$<br>130–134<br>pentane |
| 57 | 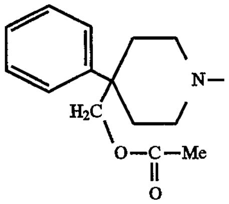 | 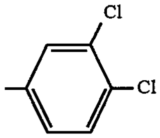 | HCl, $1H_2O$<br>NMR<br>pentane/ether |
| 58 | 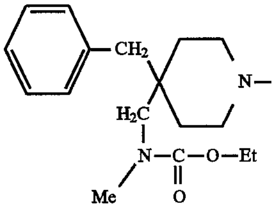 | 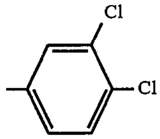 | HCl, $0.5H_2O$<br>NMR<br>DCM/ether |

TABLE I-continued

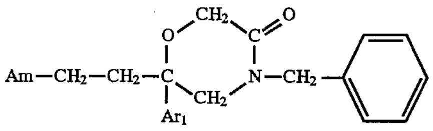

(I)

| Example | AM | $Ar_1$ | Salt, solvate; M.p. °C. or NMR; recrystallization solvent |
|---|---|---|---|
| 59 | 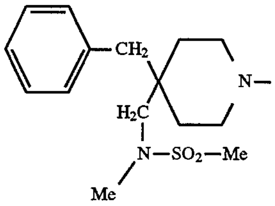 | 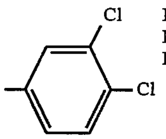 | HCl, $1H_2O$ NMR DCM/ether |
| 60 | 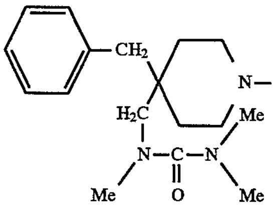 | 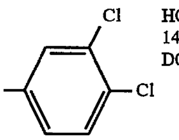 | HCl, $1H_2O$ 148 DCM/pentane |
| 61 | 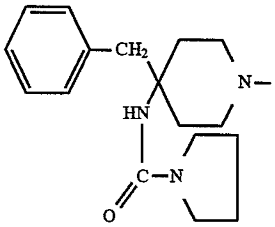 | 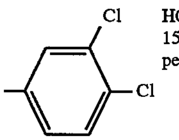 | HCl, $1.5H_2O$ 158 pentane/ether |
| 62 | 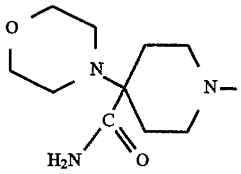 | 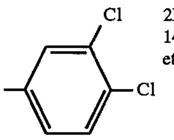 | 2HCl, $1.5H_2O$ 140–145 ether |

Proton NMR spectrum of EXAMPLE 57 at 200 MHz in DMSO-$d_6$

| | |
|---|---|
| δ: | 1.6 to 3.7 ppm : u : 17H |
| | 3.75 to 4.8 ppm : u : 6H |
| | 7.0 to 7.6 ppm : u : 13H |
| | 10.2 to 11 ppm : 2s : 1H |

Proton NMR spectrum of EXAMPLE 58 at 200 MHz in DMSO-$d_6$

| | |
|---|---|
| δ: | 0.8 to 4.9 ppm : u : 30H |
| | 7.0 to 7.8 ppm : u : 13H |
| | 10.0 ppm : s : 1H |

Proton NMR spectrum of EXAMPLE 59 at 200 MHz in DMSO-$d_6$

| | |
|---|---|
| δ: | 1.1 to 3.8 ppm : u : 24H |
| | 3.9 to 4.75 ppm : u : 4H |
| | 6.9 to 7.7 ppm : u : 13H |
| | 9.7 ppm : s : 1H |

EXAMPLE 63

6-[2-[4-Benzyl-1-azoniabicyclo[2.2.2]oct-1-yl]ethyl]-6-(3,4-difluorophenyl)-4-[3,5-bis(trifluoromethyl)benzyl]morpholin-3-one chloride dihydrate A mixture of 0.86 g of the compound obtained in step C of EXAMPLE 26 and 0.47 g of 4-benzyl-1-azabicyclo[2.2.2]octane (or 4-benzylquinuclidine) in 1 ml of DMF is heated at 90° C. for 9 hours. After cooling to RT, the reaction mixture is poured into water and extracted with DCM, the organic phase is washed twice with 2N HCl solution and twice with saturated NaCl solution and dried over $Na_2SO_4$ and the solvent is evaporated off under vacuum. The residue is chromatographed on silica H using DCM and then a DCM/MeOH mixture (90/10; v/v) as the eluent to give 0.4 g of the expected product after crystallization from ether.

M.p.=135° C. (dec.).

EXAMPLE 64

6-(3,4-Difluorophenyl)-4-[3,5-bis(trifluoromethyl)benzyl]-6-[2-[4-(piperid-1-yl)piperid-1-yl]ethyl]morpholin-3-one dihydrochloride hemihydrate A mixture of 0.86 g of the compound obtained in step C of EXAMPLE 26 and 0.7 g of 4-(piperid-1-yl)piperidine in 3 ml of DMF is heated at 70° C. for 4 hours 30 minutes. After cooling to RT, the reaction mixture is poured into water and extracted with AcOEt, the organic phase is washed with 1N NaOH solution and with saturated NaCl solution and dried over $Na_2SO_4$ and the solvent is evaporated off under vacuum. The residue is chromatographed on silica H using DCM and then a DCM/MeOH mixture (90/10; v/v) as the eluent. The product obtained is taken up with a saturated solution of hydrochloric acid in ether and the precipitate formed is wrung to give 0.49 g of the expected product.

M.p.=260° C. (dec.).

The compounds according to the invention which are collated in TABLE II below are prepared by the procedures described in the preceding EXAMPLES.

TABLE II

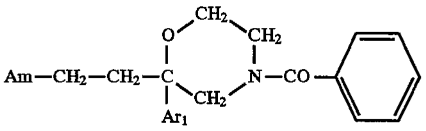

(I)

| Example | Am | $Ar_1$ | Salt, solvate; M.p. °C. or NMR; recrystallization solvent |
|---|---|---|---|
| 65 (a) | 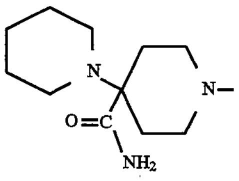 | 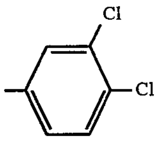 | 2HCl, $1H_2O$ NMR |
| 66 (b) | 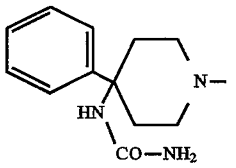 | 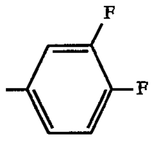 | HCl, $1.5H_2O$ 192–195 DCM/ether |
| 67 (c) | 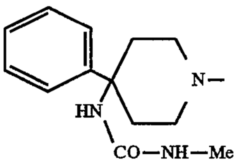 | 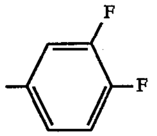 | HCl, $1H_2O$ NMR ether |

(a) This compound is prepared by the procedure described in EXAMPLE 44 from the compound obtained in step C of EXAMPLE 43 and the compound obtained in Preparation 2.16, in the form of the free base.

(b) This compound is prepared by the procedure described in step B of EXAMPLE 51 from the compound obtained in step A of EXAMPLE 51 and the compound obtained in Preparation 2.17 (free base). After chromatography, the product obtained is dissolved in DCM, a saturated solution of hydrochloric acid in ether is added until the pH is 1, and the expected hydrochloride is wrung.

(c) This compound is prepared by the procedure described in step B of EXAMPLE 51 from the compound obtained in step A of EXAMPLE 51 and the compound obtained in Preparation 2.18 (free base). After chromatography, the product obtained is taken up with a saturated solution of hydrochloric acid in ether and the expected hydrochloride is wrung.

Proton NMR spectrum of EXAMPLE 65 at 200 MHz in DMSO-$d_6$

δ: 0.8 to 4.2 ppm: u: 28H; 7.0 to 7.8 ppm: u: 8H; 7.9 to 8.6 ppm: 2s : 2H; 10.4 to 11.6 ppm: u: 2H.

Proton NMR spectrum of EXAMPLE 67 at 200 MHz in DMSO-$d_6$

| | |
|---|---|
| δ: | 2.0 to 4.2 ppm : u : 21H |
| | 5.9 ppm : mt : 1H |
| | 6.75 ppm : s : 1H |
| | 7.0 to 7.8 ppm : u : 8H |
| | 10.95 ppm : s : 1H. |

EXAMPLE 68

4-Benzoyl-2-(3,4-difluorophenyl)-2-[2-(4-phenyl-4-ureidopiperid-1-yl)ethyl]morpholine hydrochloride dihydrate, (+) isomer A) 4-Benzoyl-2-(3,4-difluorophenyl)-2-(formylmethyl) morpholine, (+) isomer A solution of 2.6 ml of oxalyl chloride in 59 ml of DCM is cooled to −78° C. under a nitrogen atmosphere and a solution of 4.6 ml of DMSO in 29.5 ml of DCM is added dropwise, followed by a solution of 8.2 g of the compound obtained in step B of EXAMPLE 37 in 59 ml of DCM and 5.7 ml of DMSO. The reaction mixture is stirred for 30 minutes at −60° C., 16 ml of triethylamine are then added and the reaction mixture is stirred while the temperature is allowed to rise to RT. It is washed with 1N HCl solution, with water, with saturated $NaHCO_3$ solution and with water, the organic phase is dried over $MgSO_4$ and the solvent is evaporated off under vacuum to give 7.5 g of the expected product in the form of an oil.

B) 4-Benzoyl-2-(3,4-difluorophenyl)-2-[2-(4-phenyl-4-ureidopiperid-1-yl)ethyl]morpholine hydrochloride dihydrate, (+) isomer A solution of 2.5 g of the compound obtained in the previous step in 26 ml of MeOH is added at RT to a solution of 1.6 g of 4-phenyl-4-ureidopiperidine (free base) and 0.4 ml of acetic acid in 26 ml of MeOH and the mixture is stirred for 5 minutes at RT. A solution of 0.5 g of sodium cyanoborohydride in 26 ml of MeOH is then added all at once and the reaction mixture is stirred for 4 hours at RT. It is poured into 200 ml of 10% $Na_2CO_3$ solution and extracted with AcOEt, the organic phase is washed with water and dried over $MgSO_4$ and the solvent is evaporated off under vacuum. The residue is chromatographed on silica H using a gradient of a DCM/MeOH mixture (from 100/5; v/v to 100/7.5; v/v) as the eluent. The product obtained is dissolved in DCM, a saturated solution of hydrochloric acid in ether is added until the pH is 1, and the precipitate formed is wrung to give 1.6 g of the expected product.

M.p.=187°–190° C.

$[\alpha]_D^{20}$=+22.5° (c=1; MeOH)

EXAMPLE 69

4-Benzoyl-2-(3,4-difluorophenyl)-2-[2-[4-(N'-methylureido)-4-phenylpiperid-1-yl]ethyl] morpholine hydrochloride monohydrate, (+) isomer This compound is prepared by the procedure described in step B of EXAMPLE 68 from 1.85 g of 4-(N'-methylureido)-4-phenylpiperidine (free base), 0.44 ml of acetic acid and 26 ml of MeOH, and then 2.75 g of the compound obtained in step A of EXAMPLE 68 in 26 ml of MeOH and 0.55 g of sodium cyanoborohydride in 26 ml of MeOH. This gives 2 g of the expected product.

M.p.=170°–173° C.

$[\alpha]_D^{20}$=+23.4° (c=1; MeOH)

EXAMPLE 70

4-Benzoyl-2-(3,4-difluorophenyl)-2-[2-[4-(3,3-dimethylcarbazoyl)-4-phenylpiperid-1-yl]ethyl] morpholine dihydrochloride 1.5 hydrate, (+) isomer This compound is prepared by the procedure described in step B of EXAMPLE 68 from 1.55 g of 4-(3,3-dimethylcarbazoyl)-4-phenylpiperidine (free base) and 0.38 ml of acetic acid in 26 ml of MeOH, and then 2.4 g of the compound obtained in step A of EXAMPLE 68 in 26 ml of MeOH and 0.47 g of sodium cyanoborohydride in 26 ml of MeOH. This gives 1.82 g of the expected product.

$[\alpha]_D^{20}$=+22.5° (c=1; MeOH)

EXAMPLE 71

2-(3,4-Difluorophenyl)-4-[2-(3-isopropoxyphenyl) acetyl]-2-[2-[4-phenyl-1-azoniabicyclo[2.2.2]oct-1-yl]ethyl]morpholine chloride monohydrate A) 2-[2-(Benzoyloxy)ethyl]-2-(3,4-difluorophenyl)-4-[2-(3-isopropoxyphenyl)acetyl]morpholine 3.2 g of BOP are added at RT to a solution of 2.1 g of the compound obtained in Preparation 1.21, 1.2 g of 2-(3-isopropoxyphenyl)acetic acid and 2.2 ml of triethylamine in 50 ml of DCM and the reaction mixture is stirred for 15 minutes at RT. It is concentrated under vacuum, the residue is extracted with ether, the organic phase is washed with 1N HCl solution, with water and with 10% $Na_2CO_3$ solution and dried over $MgSO_4$ and the solvent is evaporated off under vacuum to give 3.2 g of the expected product in the form of an oil.

B) 2-(3,4-Difluorophenyl)-2-(2-hydroxyethyl)-4-[2-(3-isopropoxyphenyl)acetyl]morpholine A mixture of 3.2 g of the compound obtained in the previous step, 2 ml of concentrated NaOH solution and 50 ml of MeOH is stirred for 2 hours at RT. It is concentrated under vacuum, the residue is extracted with ether, the organic phase is washed twice with water and dried over $MgSO_4$ and the solvent is evaporated off under vacuum to give 2.3 g of the expected product in the form of an oil.

C) 2-(3,4-Difluorophenyl)-4-[2-(3-isopropoxyphenyl) acetyl]-2-[2-(methanesulfonyloxy)ethyl]morpholine 0.93 ml of triethylamine and then 0.51 ml of methanesulfonyl chloride are added to a solution of 2.3 g of the compound obtained in the previous step in 50 ml of DCM and the mixture is stirred for 15 minutes at RT. It is concentrated under vacuum, the residue is extracted with ether, the organic phase is washed with water and with 10% $Na_2CO_3$ solution and dried over $MgSO_4$ and the solvent is evaporated off under vacuum to give 2.7 g of the expected product in the form of an oil.

D) 2-(3,4-Difluorophenyl)-4-[2-(3-isopropoxyphenyl) acetyl]-2-[2-[4-phenyl-1-azoniabicyclo[2.2.2]oct-1-yl] ethyl]morpholine chloride monohydrate A mixture of 1.3 g of the compound obtained in the previous step and 0.72 g of 4-phenyl-1-azabicyclo[2.2.2] octane in 1.5 ml of DMF is heated at 90° C. for 5 hours. After cooling to RT, the reaction mixture is poured into 1N HCl solution and extracted with DCM, the organic phase is washed with 1N HCl solution and with saturated NaCl solution and dried over $MgSO_4$ and the solvent is evaporated off under vacuum. The residue is chromatographed on silica H using DCM and then a DCM/MeOH mixture (90/10; v/v) as the eluent to give 0.38 g of the expected product after crystallization from iso ether. M.p.=136° C. (dec.).

EXAMPLE 72

2-(3,4-Difluorophenyl)-4-[2-(3-isopropoxyphenyl) acetyl]-2-[2-[4-(piperid-1-yl)piperid-1-yl]ethyl] morpholine dihydrochloride hemihydrate A mixture of 1.3 g of the compound obtained in step C of EXAMPLE 71 and 1.1 g of 4-(piperid-1-yl)piperidine in 4 ml of DMF is heated at 70° C. for 4 hours. After cooling to RT, the reaction mixture is poured into iced water and extracted with AcOEt, the organic phase is washed with 1N NaOH solution and with saturated NaCl solution and dried over $Na_2SO_4$ and the solvent is evaporated off under vacuum. The residue is chromatographed on silica H using DCM and then a DCM/MeOH mixture (90/10; v/v) as the eluent. The product obtained is taken up with a saturated solution of hydrochloric acid in ether and the precipitate formed is wrung to give 0.49 g of the expected product.

M.p.=270° C. (dec.).

EXAMPLE 73

2-(3,4-Difluorophenyl)-2-[2-[4-phenyl-1-azoniabicyclo[2.2.2]oct-1-yl]ethyl]-4-[3,5-bis (trifluoromethyl)benzoyl]morpholine chloride 1.5 hydrate A) 2-[2-(Benzoyloxy)ethyl]-2-(3,4-difluorophenyl)-4-[3,5-bis(trifluoromethyl)benzoyl]morpholine A solution of 2.1 g of the compound obtained in Preparation 1.21 and 1 ml of triethylamine in 50 ml of DCM is cooled to 0° C., 1.24 ml of 3,5-bis(trifluoromethyl)benzoyl chloride are added dropwise and the reaction mixture is stirred for 5 minutes. It is washed twice with water, the organic phase is dried over $MgSO_4$ and the solvent is evaporated off under vacuum to give 3.5 g of the expected product in the form of an oil.

B) 2-(3,4-Difluorophenyl)-2-(2-hydroxyethyl)-4-[3,5-bis (trifluoromethyl)benzoyl]morpholine A mixture of 3.5 g of the compound obtained in the previous step, 2 ml of concentrated NaOH solution and 50 ml of MeOH is stirred for 2 hours at RT. It is concentrated under vacuum, the residue is extracted with ether, the organic phase is washed twice with water and dried over $MgSO_4$ and the solvent is evaporated off under vacuum to give 0.84 g of the expected product after crystallization from an iso ether/pentane mixture. M.p.=101° C.

C) 2-(3,4-Difluorophenyl)-2-[2-(methanesulfonyloxy)ethyl] -4-[3,5-bis(trifluoromethyl)benzoyl]morpholine 0.5 ml of triethylamine is added to a solution of 0.84 g of the compound obtained in the previous step in 10 ml of DCM, the mixture is cooled to 0° C., 0.26 ml of methanesulfonyl chloride is then added and the reaction mixture is stirred for 5 minutes at RT. It is washed twice with water, the organic phase is dried over $MgSO_4$ and the solvent is evaporated off under vacuum to give 0.98 g of the expected product.

D) 2-(3,4-Difluorophenyl)-2-[2-[4-phenyl-1-azoniabicyclo [2.2.2]oct-1-yl]ethyl]-4-[3,5-bis(trifluoromethyl)benzoyl] morpholine chloride 1.5 hydrate A mixture of 0.98 g of the compound obtained in the previous step and 0.65 g of 4-phenyl-1-azabicyclo[2.2.2] octane in 1 ml of DMF is heated at 100° C. for 3 hours. After cooling to RT, the reaction mixture is poured into 1N HCl solution and extracted with DCM, the organic phase is washed with 1N HCl solution and with saturated NaCl solution and dried over $MgSO_4$ and the solvent is evaporated off under vacuum. The residue is chromatographed on silica H using DCM and then a DCM/MeOH mixture (90/10; v/v) as the eluent to give 0.42 g of the expected product after crystallization from iso ether. M.p.=170° C. (dec.).

EXAMPLE 74

5-[2-(4-Acetamido-4-phenylpiperid-1-yl)ethyl]3-benzoyl-5-(3,4-dichlorophenyl)oxazolidine hydrochloride monohydrate A) 3-Benzoyl-5-(3,4-dichlorophenyl)-5-(2-hydroxyethyl) oxazolidine A solution of 1.23 g of benzoyl chloride in 10 ml of DCM is added dropwise at RT to a solution of 3.2 g of the compound obtained in Preparation 1.22 and 1 g of triethylamine in 50 ml of DCM and the mixture is stirred for 1 hour at RT. A further 1.76 g of triethylamine and then 2.46 g of benzoyl chloride are added and the mixture is stirred for 1 hour at RT. It is concentrated under vacuum, the residue is taken up with water and extracted with AcOEt, the organic phase is washed with a buffer solution of pH 2 and with saturated NaCl solution and dried over $Na_2SO_4$ and the solvent is evaporated off under vacuum. The residue is taken up with 30 ml of MeOH, 2 ml of 30% NaOH solution are added and the mixture is stirred for 30 minutes at RT. It is concentrated under vacuum, the residue is extracted with ether, the organic phase is washed with water and dried over $Na_2SO_4$ and the solvent is evaporated off under vacuum. The residue is chromatographed on silica H using a DCM/MeOH mixture (100/1.5; v/v) a the eluent to give 1.6 g of the expected product.

B) 3-Benzoyl-5-(3,4-dichlorophenyl)-5-[2-(methanesulfonyloxy)ethyl]oxazolidine

A solution of 0.55 g of methanesulfonyl chloride in 5 ml of DCM is added dropwise at RT to a solution of 1.6 g of the compound obtained in the previous step and 0.485 g of triethylamine in 50 ml of DCM and the mixture is stirred for 30 minutes at RT. It concentrated under vacuum, the residue is extracted with AcOEt, the organic phase is washed with water and dried over $Na_2SO_4$ and the solvent is evaporated off under vacuum to give 1.9 g of the expected product.

C) 5-[2-(4-Acetamido-4-phenylpiperid-1-yl)ethyl]-3-benzoyl-5-(3,4-dichlorophenyl)oxazolidine hydrochloride monohydrate A mixture of 1.8 g of the compound obtained in the previous step, 1.7 g of 4-acetamido-4-phenylpiperidine p-toluenesulfonate and 1.7 g of $K_2CO_3$ in 4 ml of DMF is heated at 80°–100° C. for 2 hours. After cooling to RT, the reaction mixture is poured into water and the precipitate formed is wrung and dried under vacuum. The precipitate is chromatographed on silica H using a DCM/MeOH mixture (100/3; v/v) as the eluent. The product is dissolved in DCM, a saturated solution of hydrochloric acid in ether is added until the pH is 1, and the precipitate formed is wrung to give 1 g of the expected product. M.p.=165°–170° C.

EXAMPLE 75

5-(3,4-Difluorophenyl)-5-[2-[4-phenyl-1-azoniabicyclo[2.2.2]oct-1-yl]ethyl]-3-[3,5-bis (trifluoromethyl)benzyl]oxazolidin-2-one chloride monohydrate, (+) isomer A) 5-[2-(Benzoyloxy)ethyl]-5-(3,4-difluorophenyl)-3-[3,5-bis(trifluoromethyl)benzyl]oxazolidin-2-one, (+) isomer This compound is prepared by the procedure described in step A of EXAMPLE 50 from the compound obtained in Preparation 1.23 ((+) isomer).

B) 5-(3,4-Difluorophenyl)-5-(2-hydroxyethyl)-3-[3,5-bis(trifluoromethyl)benzyl]oxazolidin-2-one, (+) isomer This compound is prepared by the procedure described in step B of EXAMPLE 50 from the compound obtained in the previous step.

C) 5-(3,4-Difluorophenyl)-5-[2-(methanesulfonyloxy)ethyl]-3-[3,5-bis(trifluoromethyl)benzyl]oxazolidin-2-one, (+) isomer This compound is prepared by the procedure described in step C of EXAMPLE 50 from the compound obtained in the previous step.

D) 5-(3,4-Difluorophenyl)-5-[2-[4-phenyl-1-azoniabicyclo[2.2.2]oct-1-yl]ethyl]-3-[3,5-bis(trifluoromethyl)benzyl]oxazolidin-2-one chloride monohydrate (+) isomer This compound is prepared by the procedure described in step D of EXAMPLE 50 from the compound obtained in the previous step and 4-phenyl-1-azabicyclo[2.2.2]octane.

$[\alpha]_D^{20}=+36.2°$ (c=1; MeOH)

EXAMPLE 76

4-Benzoyl-2-[3-[4-carbamoyl-4-(piperid-1-yl)piperid-1-yl]propyl]-2-(3,4-dichlorophenyl)morpholine dihydrochloride This compound is prepared by the procedure described in step C of EXAMPLE 19 from the compound obtained in step B of EXAMPLE 19 and the compound obtained in Preparation 2.16.

EXAMPLE 77

2-(3,4-Dichlorophenyl)-4-[2-(3-chlorophenyl)acetyl]-2-[2-[4-phenyl-1-azoniabicyclo[2.2.2]oct-1-yl]ethyl]morpholine chloride A) 2-[2-(Benzoyloxy)ethyl]-2-(3,4-dichlorophenyl)-4-[2-(3-chlorophenyl)acetyl]morpholine This compound is prepared by the procedure described in step A of EXAMPLE 71 from the compound obtained in Preparation 1.19 and 2-(3-chlorophenyl)acetic acid.

B) 2-(3,4-Dichlorophenyl)-4-[2-(3-chlorophenyl)acetyl]-2-(2-hydroxyethyl)morpholine This compound is prepared by the procedure described in step B of EXAMPLE 71 from the compound obtained in the previous step.

C) 2-(3,4-Dichlorophenyl]-4-[2-(3-chlorophenyl]acetyl]-2-[2-(methanesulfonyloxy)ethyl]morpholine This compound is prepared by the procedure described in step C of EXAMPLE 71 from the compound obtained in the previous step and methanesulfonyl chloride.

D) 2-(3,4-Dichlorophenyl)-4-[2-(3-chlorophenyl)acetyl]-2-[2-[4-phenyl-1-azoniabicyclo[2.2.2]oct-1-yl]ethyl]morpholine chloride This compound is prepared by the procedure described in step D of EXAMPLE 71 from the compound obtained in the previous step and 4-phenyl-1-azabicyclo[2.2.2]octane.

Proton NMR spectrum at 200 MHz in DMSO-$d_6$ δ: 2.0 to 2.5 ppm: u: 8H ; 2.55 to 4.6 ppm: u: 16H; 7.0 to 8.0 ppm: u: 12H.

EXAMPLE 78

2-(3,4-Dichlorophenyl)-4-[2-(3-chlorophenyl)acetyl]-2-[4-benzyl-1-azoniabicyclo[2.2.2]oct-1-yl]ethyl]morpholine chloride This compound is prepared by the procedure described in step D of EXAMPLE 71 from the compound obtained in step C of EXAMPLE 77 and 4-benzyl-1-azabicyclo[2.2.2]octane.

What is claimed is:

1. A compound of the formula

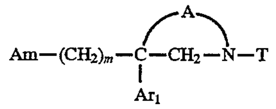

(I)

in which:

A is a divalent radical selected from:

$A_1$) —O—CO—

$A_2$) —$CH_2$—O—CO—

$A_3$) —O—$CH_2$—CO—

$A_4$) —O—$CH_2$—$CH_2$—

$A_5$) —N($R_1$)—CO—

$A_6$) —N($R_1$)—CO—CO—

$A_7$) —N($R_1$)—$CH_2$—$CH_2$—

$A_8$) —O—$CH_2$— in which $R_1$ is a hydrogen or a ($C_1$–$C_4$)-alkyl;

m is 2 or 3;

$Ar_1$ is a phenyl which is unsubstituted or monosubstituted or polysubstituted by a substituent selected from a halogen atom, a hydroxyl, a ($C_1$–$C_4$)-alkoxy, a ($C_1$–$C_4$)-alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a ($C_1$–$C_4$)-alkyl or a benzyl; an imidazolyl which is unsubstituted or substituted by a halogen atom; a pyridyl which is unsubstituted or substituted by a halogen atom; or a biphenyl;

T is a group selected from $CH_2$—Z, —CH($C_6H_5$)$_2$ and —C($C_6H_5$)$_3$; T can also be the group —CO—B—Z if A is a divalent radical selected from —O—$CH_2$—$CH_2$—, —N($R_1$)—$CH_2$—$CH_2$— and —O—$CH_2$—;

B is a direct bond or a methylene;

Z is an optionally substituted mono-, di- or tricyclic aromatic or heteroaromatic group; and Am is:

i—either a group $Am_1$ of the formula

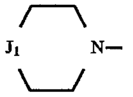

in which $J_1$ is:

$i_1$—either a group

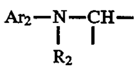

in which:

$Ar_2$ is a pyridyl; a phenyl which is unsubstituted or monosubstituted or polysubstituted by a substituent selected from a halogen atom, a hydroxyl, a ($C_1$–$C_4$)-alkoxy, a ($C_1$–$C_4$)-alkyl, a trifluoromethyl, a nitro and a methylenedioxy, said substituents being identical or different; a thienyl; a pyrimidyl; or an imidazolyl which is unsubstituted or substituted by a ($C_1$–$C_4$)-alkyl; and $R_2$ is a hydrogen; a ($C_1$–$C_7$)-alkyl; a benzyl; a formyl; or a ($C_1$–$C_7$)-alkylcarbonyl;

$i_2$—or a group

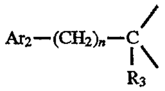

in which:

$Ar_2$ is as defined above;

n is 0 or 1; and $R_3$ is a group selected from:

(1) hydrogen;
(2) $(C_1-C_7)$-alkyl;
(3) formyl;
(4) $(C_1-C_7)$-alkylcarbonyl;
(5) cyano;
(6) $-(CH_2)_q-OH$;
(7) $-(CH_2)_q-O-(C_1-C_7)$-alkyl;
(8) $-(CH_2)_q-OCHO$;
(9) $-(CH_2)_q-OCOR_{17}$;
(10) $-(CH_2)_q-OCONH-(C_1-C_7)$-alkyl;
(11) $-NR_4R_5$;
(12) $-(CH_2)_q-NR_6C(=W_1)R_7$;
(13) $-(CH_2)_q-NR_6COOR_8$;
(14) $-(CH_2)_q-NR_6SO_2R_9$;
(15) $-(CH_2)_q-NR_6C(=W_1)NR_{10}R_{11}$;
(16) $-CH_2-NR_{12}R_{13}$;
(17) $-CH_2-CH_2NR_{12}R_{13}$;
(18) $-COOH$;
(19) $(C_1-C_7)$-alkoxycarbonyl;
(20) $-C(=W_1)NR_{10}R_{11}$;
(21) $-CH_2-COOH$;
(22) $(C_1-C_7)$-alkoxycarbonylmethyl;
(23) $-CH_2-C(=W_1)NR_{10}R_{11}$;
(24) $-O-CH_2CH_2-OR_{18}$;
(25) $-NR_6COCOR_{19}$;
(26) $-CO-NR_{20}-NR_{21}R_{22}$;
(27)

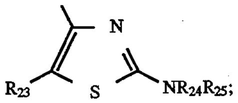

(28)

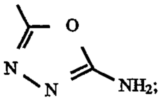

or $R_3$ constitutes a double bond between the carbon atom to which it is bonded and the adjacent carbon atom of the piperidine ring;

q is 0, 1 or 2;

$W_1$ is an oxygen atom or a sulfur atom;

$R_4$ and $R_5$ are each independently a hydrogen or a $(C_1-C_7)$-alkyl; $R_5$ can also be a $(C_3-C_7)$-cycloalkylmethyl, a benzyl or a phenyl; or $R_4$ and $R_5$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_6$ is a hydrogen or a $(C_1-C_7)$-alkyl;

$R_7$ is a hydrogen; a $(C_1-C_7)$-alkyl; a vinyl; a phenyl; a benzyl; a pyridyl; a $(C_3-C_7)$-cycloalkyl which is unsubstituted or substituted by one or more methyls; a furyl; a thienyl; a pyrrolyl; or an imidazolyl;

or $R_6$ and $R_7$ together are a group $-(CH_2)_p-$;

p is 3 or 4;

$R_8$ is a $(C_1-C_7)$-alkyl or a phenyl;

$R_9$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

$R_{10}$ and $R_{11}$ are each independently a hydrogen or a $(C_1C_7)$-alkyl; $R_{11}$ can also be a $(C_3-C_7)$-cycloalkyl, a $(C_3-C_7)$-cycloalkylmethyl, a hydroxyl, a $(C_1-C_4)$-alkoxy, a benzyl or a phenyl; or $R_{10}$ and $R_{11}$, together with the nitrogen atom to which they are bonded, form a heterocycle selected from azetidine, pyrrolidine, piperidine, morpholine, thiomorpholine and perhydroazepine;

$R_{12}$ and $R_{13}$ are each independently a hydrogen or a $(C_1-C_7)$-alkyl; $R_{13}$ can also be a $(C_3-C_7)$-cycloalkylmethyl or a benzyl;

$R_{17}$ is a $(C_1-C_7)$-alkyl; a $(C_3-C_7)$-cycloalkyl which is unsubstituted or substituted by one or more methyls; a phenyl; or a pyridyl;

$R_{18}$ is a hydrogen; a $(C_1-C_7)$-alkyl; a formyl; or a $(C_1-C_7)$-alkylcarbonyl;

$R_{19}$ is a $(C_1-C_4)$-alkoxy;

$R_{20}$ is a hydrogen or a $(C_1-C_7)$-alkyl;

$R_{21}$ and $R_{22}$ are each independently a hydrogen or a $(C_1-C_7)$-alkyl;

or alternatively $R_{21}$ and $R_{22}$, together with the nitrogen atom to which they are bonded, form a heterocycle selected from pyrrolidine, piperidine and morpholine;

$R_{23}$ is a hydrogen or a $(C_1-C_7)$-alkyl; and $R_{24}$ and $R_{25}$ are each independently a hydrogen or a $(C_1-C_7)$-alkyl; $R_{25}$ can also be a formyl or a $(C_1-C_7)$-alkylcarbonyl;

$i_3$—or a group

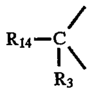

in which:

$R_3$ is as defined above;

$R_{14}$ is a $(C_1-C_7)$-alkyl or a $(C_3-C_7)$-cycloalkyl; $R_{14}$ can also be either a group $-CONR_{15}R_{16}$ if $R_3$ is hydrogen, or a group $-NR_{15}R_{16}$ if $R_3$ is hydrogen, a cyano, a carboxyl, a $(C_1-C_7)$-alkoxycarbonyl or a group $-C(=W_1)NR_{10}R_{11}$; and $R_{15}$ and $R_{16}$ are each independently a $(C_1-C_7)$-alkyl; or $R_{15}$ and $R_{16}$, together with the nitrogen atom to which they are bonded, form a heterocycle selected from azetidine, pyrrolidine, piperidine, morpholine, thiomorpholine and perhydroazepine;

ii—or a group $Am_2$ of the formula

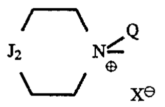

in which $J_2$ is:

$ii_1$—either a group

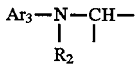

in which:

$Ar_3$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and $R_2$ is as defined above for $J_1$;

$ii_2$—or a group

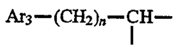

in which:

$Ar_3$ is as defined above;

n is 0 or 1;

Q is a $(C_1-C_6)$-alkyl or a benzyl, said substituent being either in the axial position or in the equatorial position; and $X^{\ominus}$ is an anion;

iii—or a group $Am_3$ of the formula

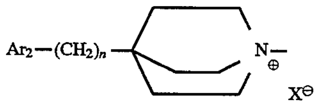

in which:

$Ar_2$ is as defined above;

n is 0 or 1; and $X^{\ominus}$ is an anion;

iv—or a group $Am_4$ of the formula

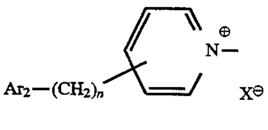

in which:

$Ar_2$ is as defined above;

n is 0 or 1; and $X^{\ominus}$ is an anion;

and the salts thereof with mineral or organic acids.

2. An optically pure compound according to claim 1 of the formula

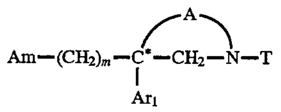

(I*)

in which:

"*" denotes that the carbon atom carrying this label has the determined (+) or (−) absolute configuration; and Am, m, $Ar_1$, A and T are as defined for the compounds of formula (I) in claim 1;

and the salts thereof with mineral or organic acids.

3. A compound according to claim 1 of formula (I) or (I*) in which:

Z is Z' and is:

a phenyl which is unsubstituted or monosubstituted or polysubstituted by a substituent selected from a halogen atom; a trifluoromethyl; a cyano; a hydroxyl; a nitro; a phenyl which is unsubstituted or monosubstituted or polysubstituted by a halogen, a trifluoromethyl, a $(C_1-C_4)$-alkyl, a hydroxyl or a $(C_1-C_4)$-alkoxy, said substituents being identical or different; an amino which is unsubstituted or monosubstituted or polysubstituted by a $(C_1-C_4)$-alkyl; a benzylamino; a carboxyl; a $(C_1-C_{10})$-alkyl; a $(C_3-C_8)$-cycloalkyl which is unsubstituted or monosubstituted or polysubstituted by a methyl; a $(C_1-C_{10})$-alkoxy; a $(C_3-C_8)$-cycloalkoxy which is unsubstituted or monosubstituted or polysubstituted by a methyl; a mercapto; a $(C_1-C_{10})$-alkylthio; a formyloxy; a $(C_1-C_6)$-alkylcarbonyloxy; a formylamino; a $(C_1-C_6)$-alkylcarbonylamino; a benzoylamino; a $(C_1-C_4)$-alkoxycarbonyl; a $(C_3-C_7)$-cycloalkoxycarbonyl; a $(C_3-C_7)$-cycloalkylcarbonyl; a carbamoyl which is unsubstituted or monosubstituted or disubstituted by a $(C_1-C_4)$-alkyl; a ureido which is unsubstituted or monosubstituted or disubstituted in the 3-position by a $(C_1-C_4)$-alkyl or a $(C_3-C_7)$-cycloalkyl; and a (pyrrolidin-1-yl)carbonylamino, said substituents being identical or different;

a naphthyl which is unsubstituted or monosubstituted or polysubstituted by a halogen, a trifluoromethyl, a $(C_1-C_4)$-alkyl, a hydroxyl or a $(C_1-C_4)$-alkoxy; or a pyridyl, a thienyl, an indolyl, a quinolyl, a benzothienyl or an imidazolyl; and Am, m, $Ar_1$, A and T are as defined for a compound of formula (I) in claim 1;

and the salts thereof with mineral or organic acids.

4. A compound according to one of claim 1 of the formula

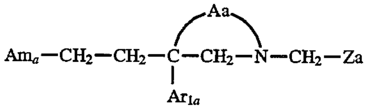

(Ia)

in which:

Aa is a divalent radical selected from —O—CO—; —$CH_2$—O—CO—; —O—$CH_2$—CO—; —$N(R_1)$—CO— and —$N(R_1)$—CO—CO—, in which $R_1$ is a hydrogen or a $(C_1-C_4)$-alkyl;

$Am_a$ is:

either a group $Am_{2a}$ of the formula

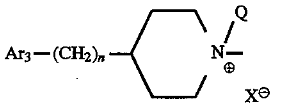

or a group $Am_3$ of the formula

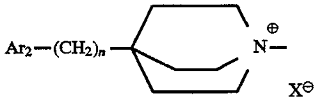

n is 0 or 1;

Q is as defined for a compound of formula (I) in claim 1 and is in the axial position;

$X^{\ominus}$ is a pharmaceutically acceptable anion;

$Ar_2$ and $Ar_3$ are as defined for a compound of formula (I) in claim 1;

$Ar_{1a}$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and Za is a phenyl which is unsubstituted or monosubstituted or polysubstituted by a substituent selected from a halogen atom, a trifluoromethyl, a $(C_1-C_{10})$-alkyl, a $(C_1-C_{10})$-alkoxy and a hydroxyl, said substituents being identical or different;

and the salts thereof with mineral or organic acids.

5. A compound according to one of claim 1 of the formula

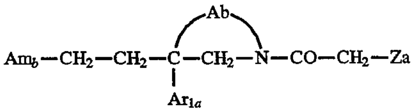

(Ib)

in which:

Ab is the divalent radical —O—$CH_2$—$CH_2$—, —N($R_1$)—$CH_2$—$CH_2$— or —O—$CH_2$—, in which $R_1$ is a hydrogen or a $(C_1-C_4)$-alkyl;

$Am_b$ is:

either a group $Am_{2a}$ of the formula

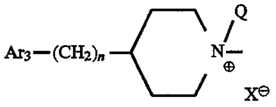

or a group $Am_3$ of the formula

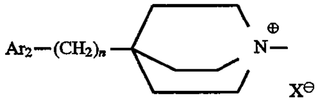

or a group $Am_{1a}$ of the formula

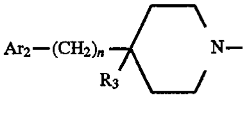

n is 0 or 1;

Q is as defined for a compound of formula (I) in claim 1 and is in the axial position;

$X^{\ominus}$ is a pharmaceutically acceptable anion;

$Ar_2$, $Ar_3$ and $R_3$ are as defined for a compound of formula (I) in claim 1;

$Ar_{1a}$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and Za is a phenyl which is unsubstituted or monosubstituted or polysubstituted by a substituent selected from a halogen atom, a trifluoromethyl, a $(C_1-C_{10})$-alkyl, a $(C_1-C_{10})$-alkoxy and a hydroxyl, said substituents being identical or different;

and the salts thereof with mineral or organic acids.

6. A compound according to one of claim 1 of the formula

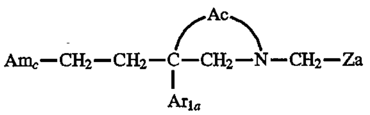

(Ic)

in which:

Ac is a divalent radical selected from —O—$CH_2$—CO—; —$CH_2$—O—CO— and —O—CO—;

$Am_c$ is a group $Am_{1a}$ of the formula

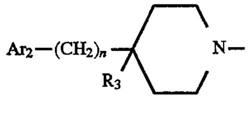

n is 0 or 1;

$Ar_2$ and $R_3$ are as defined for a compound of formula (I) in claim 1;

$Ar_{1a}$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and Za is a phenyl which is unsubstituted or monosubstituted or polysubstituted by a substituent selected from a halogen atom, a trifluoromethyl, a $(C_1-C_{10})$-alkyl, a $(C_1-C_{10})$-alkoxy and a hydroxyl, said substituents being identical or different;

and the salts thereof with mineral or organic acids.

7. A compound according to one of claim 1 of the formula

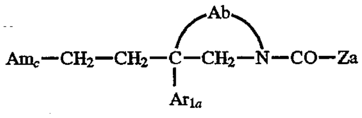

(Id)

in which:

Ab is the divalent radical —O—$CH_2$—$CH_2$—, —N($R_1$)—$CH_2$—$CH_2$— or —O—$CH_2$—;

$R_1$ is a hydrogen or a $(C_1-C_4)$-alkyl;

$Am_c$ is a group $Am_{1a}$ of the formula

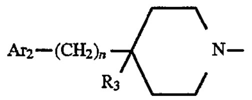

n is 0 or 1;

$Ar_2$ and $R_3$ are as defined for a compound of formula (I) in claim 1;

$Ar_{1a}$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and Za is a phenyl which is unsubstituted or monosubstituted or polysubstituted by a substituent selected from a halogen atom, a trifluoromethyl, a $(C_1-C_{10})$-alkyl, a $(C_1-C_{10})$-alkoxy and a hydroxyl, said substituents being identical or different;

and the salts thereof with mineral or organic acids.

8. A compound according to one of claim 1 of the formula:

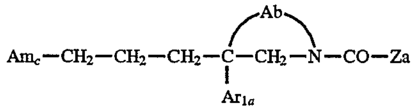

(Ie)

in which:

Ab is the divalent radical $—O—CH_2—CH_2—$, $—N(R_1)—CH_2—CH_2—$ or $—O—CH_2—$;

$R_1$ is a hydrogen or a $(C_1-C_4)$-alkyl;

$Am_c$ is a group $Am_{1a}$ of the formula

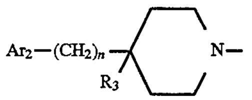

n is 0 or 1;

$Ar_2$ and $R_3$ are as defined for a compound of formula (I) in claim 1;

$Ar_{1a}$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and Za is a phenyl which is unsubstituted or monosubstituted or polysubstituted by a substituent selected from a halogen atom, a trifluoromethyl, a $(C_1-C_{10})$-alkyl, a $(C_1-C_{10})$-alkoxy and a hydroxyl, said substituents being identical or different;

and the salts thereof with mineral or organic acids.

9. A compound according to one of claim 1 of the formula:

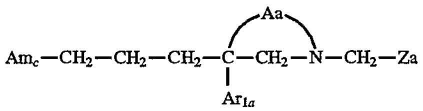

(If)

in which:

Aa is the divalent radical $—O—CO—$, $—CH_2—O—CO—$, $—O—CH_2—CO—$, $—N(R_1)—CO—$ or $—N(R_1)—CO—CO—$;

$R_1$ is a hydrogen or a $(C_1-C_4)$-alkyl;

$Am_c$ is a group $Am_{1a}$ of the formula

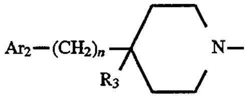

n is 0 or 1;

$Ar_2$ and $R_3$ are as defined for a compound of formula (i) in claim 1;

$Ar_{1a}$ is a phenyl which is unsubstituted or monosubstituted or polysubstituted by a substituent selected from a halogen atom, a hydroxyl, a $(C_1-C_4)$-alkoxy, a $(C_1-C_4)$-alkyl and a trifluoromethyl, said substituents being identical or different; and Za is a phenyl which is unsubstituted or monosubstituted or polysubstituted by a substituent selected from a halogen atom, a trifluoromethyl, a $(C_1-C_{10})$-alkyl, a $(C_1-C_{10})$-alkoxy and a hydroxyl, said substituents being identical or different;

and the salts thereof with mineral or organic acids.

10. 4-Benzoyl-2-(3,4-difluorophenyl)-2-[2-[4-(N',N'-dimethylureido)-4-phenylpiperid-1-yl]ethyl]morpholine, in the form of the (+) isomer, and the salts thereof with mineral or organic acids.

11. 5-(3,4-Difluorophenyl)-5-[2-[4-phenyl-1-azoniabicyclo[2.2.2]oct-1-yl]ethyl]-3-[3,5-bis(trifluoromethyl)benzyl]oxazolidin-2-one with a pharmaceutically acceptable anion, in optically pure form, preferably in the form of the (+) isomer.

12. A pharmaceutical composition in which a compound according to any one of claim 1, or a pharmaceutically acceptable salt thereof, is present as the active principle.

13. A pharmaceutical composition according to claim 12 in the form of a dosage unit in which the active principle is mixed with at least one pharmaceutical excipient.

14. A pharmaceutical composition according to claim 13 which contains 0.5 to 1000 mg of active principle.

15. A pharmaceutical composition according to claim 14 which contains 2.5 to 250 mg of active principle.

* * * * *